US010118957B2

(12) United States Patent
Gotthardt et al.

(10) Patent No.: US 10,118,957 B2
(45) Date of Patent: Nov. 6, 2018

(54) METHOD FOR TREATING HEART DISEASE BY INHIBITING THE COXSACKIEVIRUS-ADENOVIRUS RECEPTOR

(71) Applicant: Max-Delbrück-Centrum für Molekulare Medizin (MDC) Berlin-Buch, Berlin (DE)

(72) Inventors: Michael Gotthardt, Berlin (DE); Fabian Freiberg, Berlin (DE)

(73) Assignee: MAX-DELBRÜCK-CENTRUM FÜR MOLEKULARE MEDIZIN (MDC) BERLIN-BUCH, Berlin (DE)

( * ) Notice: Subject to any disclaimer, the term of this patent is extended or adjusted under 35 U.S.C. 154(b) by 0 days.

(21) Appl. No.: 14/419,413

(22) PCT Filed: Aug. 5, 2013

(86) PCT No.: PCT/EP2013/066426
§ 371 (c)(1),
(2) Date: Feb. 3, 2015

(87) PCT Pub. No.: WO2014/020184
PCT Pub. Date: Feb. 6, 2014

(65) Prior Publication Data

US 2015/0315261 A1 Nov. 5, 2015

(30) Foreign Application Priority Data

Aug. 3, 2012 (EP) .................................... 12179295
Apr. 17, 2013 (EP) .................................... 13164109

(51) Int. Cl.

| | |
|---|---|
| ***A61P 9/10*** | (2006.01) |
| ***A61K 39/395*** | (2006.01) |
| ***A61K 47/68*** | (2017.01) |
| ***A61K 38/17*** | (2006.01) |
| ***A61K 38/39*** | (2006.01) |
| ***C07K 14/705*** | (2006.01) |
| ***C07K 16/28*** | (2006.01) |
| ***A61K 45/06*** | (2006.01) |
| ***A61K 31/7088*** | (2006.01) |
| ***A61K 48/00*** | (2006.01) |
| ***C12N 15/113*** | (2010.01) |
| ***G01N 33/68*** | (2006.01) |
| *C07K 14/78* | (2006.01) |

(52) U.S. Cl.
CPC ........ *C07K 14/705* (2013.01); *A61K 31/7088* (2013.01); *A61K 38/17* (2013.01); *A61K 38/177* (2013.01); *A61K 38/39* (2013.01); *A61K 39/3955* (2013.01); *A61K 45/06* (2013.01); *A61K 47/68* (2017.08); *A61K 48/005* (2013.01); *A61P 9/10* (2018.01); *C07K 16/28* (2013.01); *C12N 15/1138* (2013.01); *G01N 33/6887* (2013.01); *C07K 14/78* (2013.01); *C07K 2319/30* (2013.01); *C12N 2310/11* (2013.01); *C12N 2310/14* (2013.01); *C12N 2310/3233* (2013.01); *C12N 2320/31* (2013.01); *G01N 2800/324* (2013.01)

(58) Field of Classification Search
None
See application file for complete search history.

(56) References Cited

U.S. PATENT DOCUMENTS

2008/0248502 A1 10/2008 Yamaguchi et al.
2011/0160236 A1 6/2011 Serebruany

FOREIGN PATENT DOCUMENTS

| | | | |
|---|---|---|---|
| DE | 102009019460 | A1 | 12/2010 |
| EP | 13164109 | | 6/2013 |
| WO | 03057195 | A1 | 7/2003 |
| WO | 2009053104 | A2 | 4/2009 |
| WO | 2011078712 | A1 | 6/2011 |
| WO | 2012064307 | A1 | 5/2012 |
| WO | PCT/EP2013/066426 | | 12/2013 |

OTHER PUBLICATIONS

Freiberg et al, 2014. Journal of Virology, 88(13): 7345-7356.*
B. Yanagawa et al., "Soluble Recombinant Coxsackievirus and Adenovirus Receptor Abrogates Coxsackievirus B3-Mediated Pancreatitis and Myocarditis in Mice," The Journal of Infectious Diseases (JID), Apr. 2004, pp. 1431-1439, vol. 189, No. 8.
S. Pinkert et al., "Prevention of Cardiac Dysfunction in Acute Coxsackievirus B3 Cardiomyopathy by Inducible Expression of a Soluble Coxsackievirus-Adenovirus Receptor," Circulation, Dec. 2009, pp. 2358-2366, vol. 120, No. 23.
L. Caruso et al., "Cardiomyocyte-Targeted Overexpression of the Coxsackie-Adenovirus Receptor Causes a Cardiomyopathy in Association with β-Catenin Signaling," Journal of Molecular and Cellular Cardiology, Jun. 2010, pp. 1194-1205, vol. 48, No. 6.
S. Yuen et al., "The Coxsackie-Adenovirus Receptor Induces an Inflammatory Cardiomyopathy Independent of Viral Infection," Journal of Molecular and Cellular Cardiology, Feb. 2011, pp. 826-840, vol. 50, No. 5.
Y. Shi et al., "Cardiac Deletion of the Coxsackievirus-Adenovirus Receptor Abolishes Coxsackievirus B3 Infection and Prevents Myocarditis in Vivo," Journal of the American College of Cardiology, Apr. 2009, pp. 1219-1226, vol. 53, No. 14.
Jadwiga Schreiber, "The cell adhesion molecule coxsackie virus and adenovirus receptor (CAR) modulates intracellular Ca2+ concentration and Cl—conductance in cultivated mouse cortical neurons," Department of Biology, Chemistry and Pharmacy, Freie Universität Berlin, 2009.

(Continued)

*Primary Examiner* — Zachary C Howard
(74) *Attorney, Agent, or Firm* — Ryan, Mason & Lewis, LLP

(57) ABSTRACT

The invention pertains to a means for downregulating or inhibiting or mislocalizing CAR in a cardiac cell for treating/curing a patient who has suffered or is predisposed to suffering a myocardial infarction (MI) or preventing myocardial infarction or complications thereof.

5 Claims, 4 Drawing Sheets

Specification includes a Sequence Listing.

(56) References Cited

OTHER PUBLICATIONS van Raaij et al., "Dimeric Structure of the Coxsackievirus and Adenovirus Receptor D1 Domain at 1.7 Å Resolution," Structure, vol. 8, Nov. 2000.
Salinas et al., "Disruption of the Coxsackievirus and Adenovirus Receptor-Homodimeric Interaction Triggers Lipid Microdomain- and Dynamin-dependent Endocytosis and Lysosomal Targeting," The Journal of Biological Chemistry, vol. 289, No. 2, (2014).
J. Bergelson et al., "Isolation of a Common Receptor for Coxsackie B Viruses and Adenoviruses 2 and 5," Science, Feb. 28, 1997, pp. 1320-1323, vol. 275.
M. Schmidtke et al., "Attachment of Coxsackievirus B3 Variants to Various Cell Lines: Mapping of Phenotypic Differences to Capsid Protein VP1," Virology, 2000, pp. 77-88, vol. 275.
P.W. Roelvink et al., "Identification of a Conserved Receptor-Binding Site on the Fiber Proteins of CAR—Recognizing Adenoviridae," Science, Nov. 19, 1999, pp. 1568-1571, vol. 286.
C.J. Cohen et al., "The Coxsackievirus and Adenovirus Receptor is a Transmembrane Component of the Tight Junction," Proceedings of the National Academy of Sciences of the United States of America, Dec. 18, 2001, pp. 15191-15196, vol. 98, No. 26.
C. Patzke et al., "The Coxsackievirus-Adenovirus Receptor Reveals Complex Homophilic and Heterophilic Interactions on Neural Cells" The Journal of Neuroscience, Feb. 24, 2010, pp. 2897-2910, vol. 30, No. 8.
C.B. Coyne et al., "The Coxsackievirus and Adenovirus Receptor Interacts with the Multi-PDZ Domain Protein-1 (MUPP-1) within the Tight Junction," The Journal of Biological Chemistry, Nov. 12, 2004, pp. 48079-48084, vol. 279, No. 46.
K.J.D.A. Excoffon et al., "A Role for the PDZ-Binding Domain of the Coxsackie B Virus and Adenovirus Receptor (CAR) in Cell Adhesion and Growth," Journal of Cell Science, 2004, pp. 4401-4409, vol. 117.
A.O. Kolawole et al., "The PDZ1 and PDZ3 Domains of MAGI-1 Regulate the Eight-Exon Isoform of the Coxsackievirus and Adenovirus Receptor," Journal of Virology, Sep. 2012, pp. 9244-9254, vol. 86, No. 17.
K. Sollerbrant et al., "The Coxsackievirus and Adenovirus Receptor (CAR) Forms a Complex with the PDZ Domain-Containing Protein Ligand-of-Numb Protein-X (LNX)," The Journal of Biological Chemistry, Feb. 28, 2003, pp. 7439-7444, vol. 278, No. 9.
P.T. Fok et al., "The Coxsackie and Adenovirus Receptor Binds Microtubules and Plays a Role in Cell Migration," The Journal of Biological Chemistry, Mar. 9, 2007, pp. 7512-7521, vol. 282, No. 10.
S.D. Carson et al., "Purification of the Putative Coxsackievirus B Receptor from HeLa Cells," Biochemical and Biophysical Research Communications, 1997, pp. 325-328, vol. 233.
C.A. Shaw et al., "Isoform-Specific Expression of the Coxsackie and Adenovirus Receptor (CAR) in Neuromuscular Junction and Cardiac Intercalated Discs," Nov. 8, 2004, 8 pages, vol. 5., No. 42.
P. Verdino et al., "The Molecular Interaction of CAR and JAML Recruits the Central Cell Signal Transducer PI3K," Science, Sep. 3, 2010, pp. 1210-1214, vol. 329.
B-K. Lim et al., "Coxsackievirus and Adenovirus Receptor (CAR) Mediates Atrioventricular-Node Function and Connexin 45 Localization in the Murine Heart," The Journal of Clinical Investigation, Aug. 2008, pp. 2758-2770, vol. 118, No. 8.
U. Lisewski, "The Tight Junction Protein Car Regulates Cardiac Conduction and Cell-Cell Communication," The Journal of Experimental Medicine, Sep. 15, 2008, pp. 2369-2379, vol. 205.
R. Fischer et al., "CAR-diology—A Virus Receptor in the Healthy and Diseased Heart," Journal of Molecular Medicine, 2009, pp. 879-884, vol. 87.
N.L. Kallewaard et al., "Tissue-Specific Deletion of the Coxsackievirus and Adenovirus Receptor Protects Mice from Virus-Induced Pancreatitis and Myocarditis," Cell Host & Microbe, Jul. 23, 2009, pp. 91-98, vol. 6.
R.W. Walters et al., "Adenovirus Fiber Disrupts CAR-Mediated Intercellular Adhesion Allowing Virus Escape," Cell, Sep. 20, 2002, pp. 789-799, vol. 110.

* cited by examiner

FIG. 3A
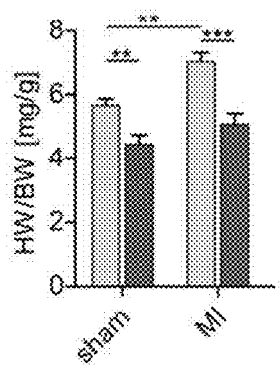
FIG. 3B
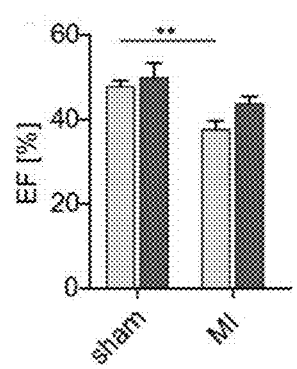
FIG. 3C
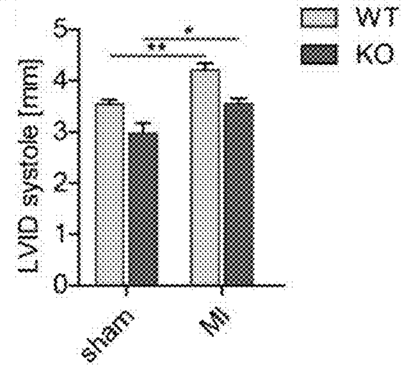
FIG. 4A
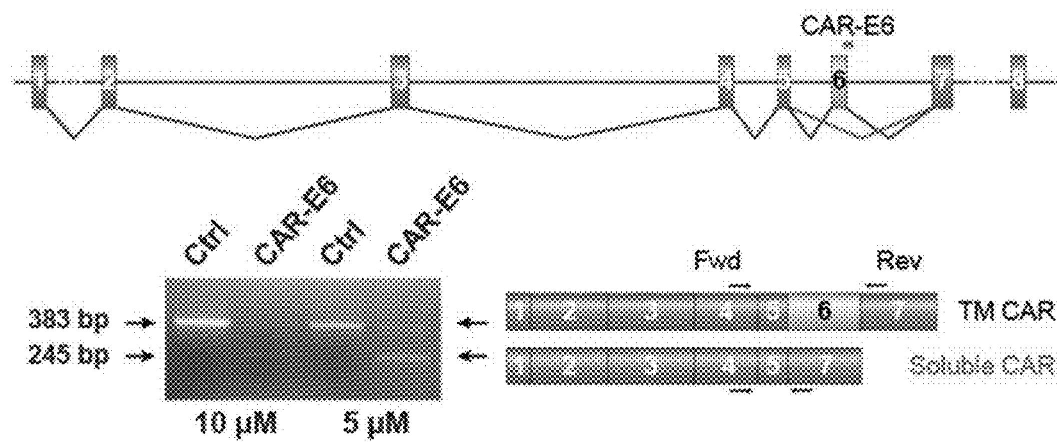
FIG. 4B

FIG. 5A
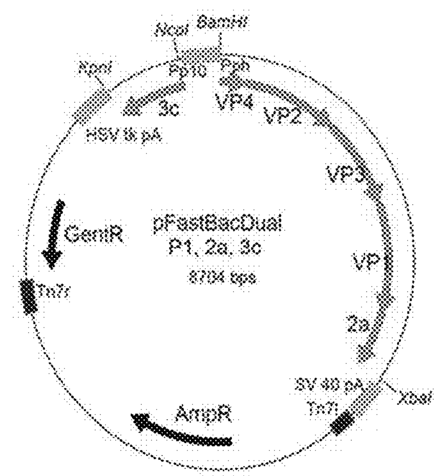
FIG. 5B
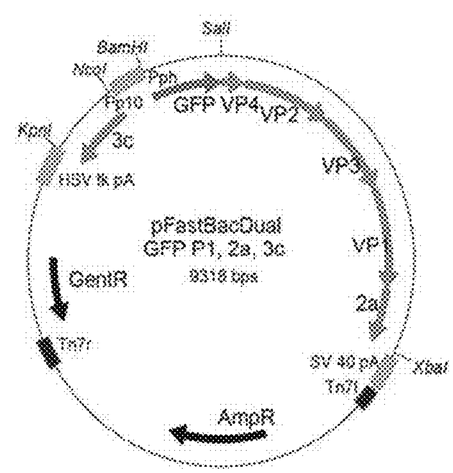
FIG. 5C
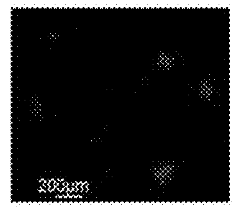
FIG. 5D
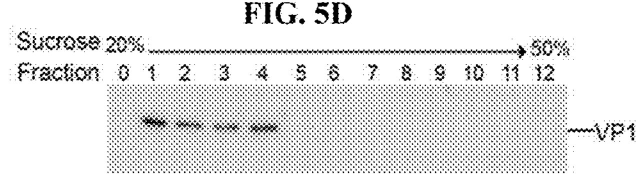
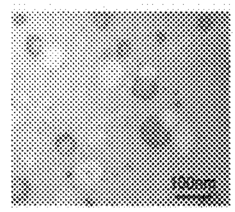
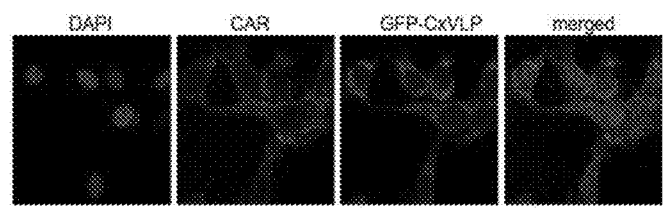
FIG. 5E
FIG. 5F

SEQUENCE LISTING

<160> NUMBER OF SEQ ID NOS: 22

<210> SEQ ID NO 1
<211> LENGTH: 1098
<212> TYPE: DNA
<213> ORGANISM: Homo sapiens

<400> SEQUENCE: 1
atggcgctcc tgctgtgctt cgtgctcctg tgcggagtag tggatttcgc cagaagtttg 60
agtatcacta ctcctgaaga gatgattgaa aaagccaaag gggaaactgc ctatctgcca 120
tgcaaattta cgcttagtcc cgaagaccag ggaccgctgg acatcgagtg gctgatatca 180
ccagctgata atcagaaggt ggatcaagtg attattttat attctggaga caaaatttat 240
gatgactact atccagatct gaaaggccga gtacatttta cgagtaatga tctcaaatct 300
ggtgatgcat caataaatgt aacgaattta caactgtcag atattggcac atatcagtgc 360
aaagtgaaaa aagctcctgg tgttgcaaat aagaagattc atctggtagt tcttgttaag 420
ccttcaggtg cgagatgtta cgttgatgga tctgaagaaa ttggaagtga ctttaagata 480
aaatgtgaac caaaagaagg ttcacttcca ttacagtatg agtggcaaaa attgtctgac 540
tcacagaaaa tgcccacttc atggttagca gaaatgactt catctgttat atctgtaaaa 600
aatgcctctt ctgagtactc tgggacatac agctgtacag tcagaaacag agtgggctct 660

```
gatcagtgcc tgttgcgtct aaacgttgtc cctccttcaa ataaagctgg actaattgca    720

ggagccatta taggaacttt gcttgctcta gcgctcattg gtcttatcat cttttgctgt    780

cgtaaaaagc gcagagaaga aaaatatgaa aaggaagttc atcacgatat cagggaagat    840

gtgccacctc caaagagccg tacgtccact gccagaagct acatcggcag taatcattca    900

tccctggggt ccatgtctcc ttccaacatg gaaggatatt ccaagactca gtataaccaa    960

gtaccaagtg aagactttga acgcactcct cagagtccga ctctcccacc tgctaaggta   1020

gctgccccta atctaagtcg aatgggtgcg attcctgtga tgattccagc acagagcaag   1080

gatgggtcta tagtatag                                                 1098


<210> SEQ ID NO 2
<211> LENGTH: 365
<212> TYPE: PRT
<213> ORGANISM: Homo sapiens

<400> SEQUENCE: 2

Met Ala Leu Leu Leu Cys Phe Val Leu Leu Cys Gly Val Val Asp Phe
1               5                   10                  15

Ala Arg Ser Leu Ser Ile Thr Thr Pro Glu Glu Met Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ala Asp Asn
    50                  55                  60

Gln Lys Val Asp Gln Val Ile Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Val Leu Val Lys Pro Ser Gly Ala
    130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
            180                 185                 190

Thr Ser Ser Val Ile Ser Val Lys Asn Ala Ser Ser Glu Tyr Ser Gly
        195                 200                 205

Thr Tyr Ser Cys Thr Val Arg Asn Arg Val Gly Ser Asp Gln Cys Leu
    210                 215                 220

Leu Arg Leu Asn Val Val Pro Pro Ser Asn Lys Ala Gly Leu Ile Ala
225                 230                 235                 240

Gly Ala Ile Ile Gly Thr Leu Leu Ala Leu Ala Leu Ile Gly Leu Ile
                245                 250                 255

Ile Phe Cys Cys Arg Lys Lys Arg Arg Glu Glu Lys Tyr Glu Lys Glu
            260                 265                 270

Val His His Asp Ile Arg Glu Asp Val Pro Pro Pro Lys Ser Arg Thr
        275                 280                 285

Ser Thr Ala Arg Ser Tyr Ile Gly Ser Asn His Ser Ser Leu Gly Ser
```

```
    290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Thr Pro Gln Ser Pro Thr Leu Pro
                325                 330                 335

Pro Ala Lys Val Ala Ala Pro Asn Leu Ser Arg Met Gly Ala Ile Pro
            340                 345                 350

Val Met Ile Pro Ala Gln Ser Lys Asp Gly Ser Ile Val
        355                 360                 365


<210> SEQ ID NO 3
<211> LENGTH: 1422
<212> TYPE: DNA
<213> ORGANISM: Homo sapiens

<400> SEQUENCE: 3

atggcgctcc tgctgtgctt cgtgctcctg tgcggagtag tggatttcgc cagaagtttg      60

agtatcacta ctcctgaaga gatgattgaa aaagccaaag gggaaactgc ctatctgcca     120

tgcaaattta cgcttagtcc cgaagaccag ggaccgctgg acatcgagtg gctgatatca     180

ccagctgata atcagaaggt ggatcaagtg attattttat attctggaga caaaatttat     240

gatgactact atccagatct gaaaggccga gtacatttta cgagtaatga tctcaaatct     300

ggtgatgcat caataaatgt aacgaattta caactgtcag atattggcac atatcagtgc     360

aaagtgaaaa aagctcctgg tgttgcaaat aagaagattc atctggtagt tcttgttaag     420

ccttcaggtg cgagatgtta cgttgatgga tctgaagaaa ttggaagtga ctttaagata     480

aaatgtgaac caaaagaagg ttcacttcca ttacagtatg agtggcaaaa attgtctgac     540

tcacagaaaa tgcccacttc atggttagca gaaatgactt catctgttat atctgtaaaa     600

aatgcctctt ctgagtactc tgggacatac agctgtacag tcagaaacag agtgggctct     660

gatcagtgcc tgttgcgtct aaacgttgtc cctccttcaa ataaagctgc caccggtgac     720

gtcgagtcca aatcttgtga caaaactcac acatgcccac cgtgcccagc acctgaactc     780

ctggggggac cgtcagtctt cctcttcccc ccaaaaccca aggacaccct catgatctcc     840

cggacccctg aggtcacatg cgtggtggtg gacgtgagcc acgaagaccc tgaggtcaag     900

ttcaactggt acgtggacgg cgtggaggtg cataatgcca agacaaagcc gcgggaggag     960

cagtacaaca gcacgtaccg tgtggtcagc gtcctcaccg tcctgcacca ggactggctg    1020

aatggcaagg agtacaagtg caaggtctcc aacaaagccc tcccagcccc catcgagaaa    1080

accatctcca aagccaaagg gcagccccga gagccacagg tgtacaccct gcccccatcc    1140

cgggatgagc tgaccaagaa ccaggtcagc ctgacctgcc tggtcaaagg cttctatccc    1200

agcgacatcg ccgtggagtg ggagagcaat gggcagccgg agaacaacta caagaccacg    1260

cctcccgtgc tggactccga cggctccttc ttcctctaca gcaagctcac cgtggacaag    1320

agcaggtggc agcaggggaa cgtcttctca tgctccgtga tgcatgaggc tctgcacaac    1380

cactacacgc agaagagcct ctccctgtct ccgggtaaat ga                       1422


<210> SEQ ID NO 4
<211> LENGTH: 472
<212> TYPE: PRT
<213> ORGANISM: Homo sapiens

<400> SEQUENCE: 4

Met Ala Leu Leu Leu Cys Phe Val Leu Leu Cys Gly Val Val Asp Phe
```

-continued

```
1               5                   10                  15

Ala Arg Ser Leu Ser Ile Thr Thr Pro Glu Glu Met Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ala Asp Asn
    50                  55                  60

Gln Lys Val Asp Gln Val Ile Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Val Leu Val Lys Pro Ser Gly Ala
    130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
            180                 185                 190

Thr Ser Ser Val Ile Ser Val Lys Asn Ala Ser Ser Glu Tyr Ser Gly
        195                 200                 205

Thr Tyr Ser Cys Thr Val Arg Asn Arg Val Gly Ser Asp Gln Cys Leu
    210                 215                 220

Leu Arg Leu Asn Val Val Pro Pro Ser Asn Lys Ala Thr Gly Asp Val
225                 230                 235                 240

Glu Ser Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430
```

```
Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470


<210> SEQ ID NO 5
<211> LENGTH: 1419
<212> TYPE: DNA
<213> ORGANISM: Mus musculus

<400> SEQUENCE: 5

atggcgcgcc tactgtgctt cgtgctcttg tgcgggatcg cggatttcac cagtggtttg      60

agcatcacta cacccgaaca gaggatcgaa aaagccaaag gggaaactgc gtatctacca     120

tgcaagttta ctctcagtcc cgaagaccag ggaccactgg acattgaatg gctgatatcc     180

ccgtctgata accagatagt ggatcaagtg atcattttgt attctggaga caaaatttat     240

gataactact atccggatct gaaaggacgg gtacatttta cgagtaacga tgtcaagtct     300

ggcgacgcat ctataaatgt gaccaacctg cagctgtcgg acattggcac ttaccagtgc     360

aaagtgaaga aagcccctgg ggttgcaaat aagaaattcc tgctgaccgt tcttgttaag     420

ccttcaggta caagatgctt cgtggatgga tcggaagaga ttggaaatga cttcaagcta     480

aaatgtgaac ccaaggaagg ctcccttcca ctacagtttg aatggcagaa actgtcggac     540

tcccagacaa tgcctacgcc atggctggca gaaatgacgt caccagttat atctgtgaag     600

aacgccagtt ctgagtattc tgggacatac agctgcacgg ttcaaaacag agtgggctct     660

gaccagtgta tgctgcgact agacgttgtc ccaccctcca accgagccac cggtgacgtc     720

gagtccaaat cttgtgacaa aactcacaca tgcccaccgt gcccagcacc tgaactcctg     780

gggggaccgt cagtcttcct cttcccccca aaacccaagg acaccctcat gatctcccgg     840

acccctgagg tcacatgcgt ggtggtggac gtgagccacg aagaccctga ggtcaagttc     900

aactggtacg tggacggcgt ggaggtgcat aatgccaaga caaagccgcg ggaggagcag     960

tacaacagca cgtaccgtgt ggtcagcgtc ctcaccgtcc tgcaccagga ctggctgaat    1020

ggcaaggagt acaagtgcaa ggtctccaac aaagccctcc cagcccccat cgagaaaacc    1080

atctccaaag ccaaagggca gccccgagag ccacaggtgt acaccctgcc cccatcccgg    1140

gatgagctga ccaagaacca ggtcagcctg acctgcctgg tcaaaggctt ctatcccagc    1200

gacatcgccg tggagtggga gagcaatggg cagccggaga acaactacaa gaccacgcct    1260

cccgtgctgg actccgacgg ctccttcttc ctctacagca agctcaccgt ggacaagagc    1320

aggtggcagc aggggaacgt cttctcatgc tccgtgatgc atgaggctct gcacaaccac    1380

tacacgcaga agagcctctc cctgtctccg ggtaaatga                           1419


<210> SEQ ID NO 6
<211> LENGTH: 472
<212> TYPE: PRT
<213> ORGANISM: Mus musculus

<400> SEQUENCE: 6

Met Ala Arg Leu Leu Cys Phe Val Leu Leu Cys Gly Ile Ala Asp Phe
1               5                   10                  15

Thr Ser Gly Leu Ser Ile Thr Thr Pro Glu Gln Arg Ile Glu Lys Ala
            20                  25                  30
```

```
Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ser Asp Asn
    50                  55                  60

Gln Ile Val Asp Gln Val Ile Ile Leu Tyr Ser Gly Asp Lys Ile Tyr
65                  70                  75                  80

Asp Asn Tyr Tyr Pro Asp Leu Lys Gly Arg Val His Phe Thr Ser Asn
                85                  90                  95

Asp Val Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Phe Leu Leu Thr Val Leu Val Lys Pro Ser Gly Thr
    130                 135                 140

Arg Cys Phe Val Asp Gly Ser Glu Glu Ile Gly Asn Asp Phe Lys Leu
145                 150                 155                 160

Lys Cys Glu Pro Lys Glu Gly Ser Leu Pro Leu Gln Phe Glu Trp Gln
                165                 170                 175

Lys Leu Ser Asp Ser Gln Thr Met Pro Thr Pro Trp Leu Ala Glu Met
            180                 185                 190

Thr Ser Pro Val Ile Ser Val Lys Asn Ala Ser Ser Glu Tyr Ser Gly
        195                 200                 205

Thr Tyr Ser Cys Thr Val Gln Asn Arg Val Gly Ser Asp Gln Cys Met
    210                 215                 220

Leu Arg Leu Asp Val Val Pro Pro Ser Asn Arg Ala Thr Gly Asp Val
225                 230                 235                 240

Glu Ser Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445
```

```
Ser Cys Ser Val Met His Glu Ala Leu His Asn His Tyr Thr Gln Lys
    450                 455                 460

Ser Leu Ser Leu Ser Pro Gly Lys
465                 470


<210> SEQ ID NO 7
<211> LENGTH: 25
<212> TYPE: DNA
<213> ORGANISM: artificial
<220> FEATURE:
<223> OTHER INFORMATION: morpholino

<400> SEQUENCE: 7

gtctagtttc actgaattac ctgat                                          25


<210> SEQ ID NO 8
<211> LENGTH: 25
<212> TYPE: DNA
<213> ORGANISM: artificial
<220> FEATURE:
<223> OTHER INFORMATION: morpholino

<400> SEQUENCE: 8

cctcttacct cagttacaat ttata                                          25


<210> SEQ ID NO 9
<211> LENGTH: 3000
<212> TYPE: DNA
<213> ORGANISM: Coxsackievirus B

<400> SEQUENCE: 9

atgggagctc aagtatcaac gcaaaagact ggggcacatg agaccgggct gaatgctagc     60

ggcaattcca tcattcacta cacaaatatt aattattaca aggatgccgc atccaactca    120

gccaatcggc aggatttcac tcaagacccg ggcaagttca cagaaccagt aaaagatatc    180

atgattaaat cactaccagc tctcaactcc cccacagtag aggagtgcgg atacagtgac    240

agggcgagat caatcacatt aggtaactcc accataacga ctcaggaatg cgccaacgtg    300

gtggtgggct atggagtatg gccagattat ctaaaggata gtgaggcaac agcagaggac    360

caaccgaccc aaccagacgt tgccacatgt aggttctata cccttgactc tgtgcaatgg    420

cagaaaacct caccaggatg gtggtggaag ctgcccgatg ctttgtcgaa cttaggactg    480

tttgggcaga acatgcagta ccactactta ggccgaactg ggtataccga tcatgtgcag    540

tgcaatgcat ctaagttcca ccaaggatgc ttgctagtag tgtgtgtacc ggaagctgag    600

atgggttgcg caacgctaga caacacccca tccagtgcag aattgctggg gggcgatacg    660

gcaaaagagt ttgcggacaa accggtcgca tccgggtcca acaagttggt acagagggtg    720

gtgtataatg caggcatggg ggtgggtgtt ggaaacctca ccattttccc ccaccaatgg    780

atcaacctac gcaccaataa tagtgctaca attgtgatgc catacaccaa cagtgtacct    840

atggataaca tgtttaggca taacaacgtc accctaatgg ttatcccatt tgtaccgcta    900

gattactgcc ctgggtccac cacgtacgtc ccaattacgg tcacgatagc cccaatgtgt    960

gccgagtaca atgggttacg tttagcaggg caccagggct taccaaccat gaatactccg   1020

gggagctgtc aatttctgac atcagacgac ttccaatcac catccgccat gccgcaatat   1080

gacgtcacac cagagatgag gatacctggt gaggtgaaaa acttgatgga aatagctgag   1140

gttgactcag ttgtcccagt ccaaaatgtt ggagagaagg tcaactctat ggaagcatac   1200

cagatacctg tgagatccaa tgaaggatct ggaacgcaag tattcggctt tccactgcaa   1260
```

```
ccagggtact cgagtgtttt tagtcggacg ctcctaggag agatcttgaa ctattataca   1320

cattggtcag gcagcataaa gcttacgttt atgttctgtg gttcggccat ggctactgga   1380

aaattccttt tggcatactc accactaggt gctggagctc ctacaaaaag ggttgatgcc   1440

atgcttggta ctcatgtagt ttgggacgtg gggctacaat caagttgcgt gctgtgtata   1500

ccctggataa gccaaacaca ctaccggtat gttgcttcag atgagtgtac cgcagggggt   1560

tttattacgt gctggtatca aacaaacata gtggtcccag cggatgccca aagctcctgt   1620

tacatcatgt gtttcgtgtc agcatgcaat gacttctctg tcaggctatt gaaggacact   1680

cctttcattt cgcaggaaaa ctttttccag ggcccagtgg aagacgcgat aacagccgct   1740

atagggagag ttgcggatac cgtgggtaca gggccaaaca actcagaagc tataccagca   1800

ctcactgctg ctgagacagg tcacacgtca caagtagtgc cgggtgacac catgcagaca   1860

cgccacgtta agaactacca ttcaaggtcc gagtcaacca tagagaactt cctatgtagg   1920

tcagcatgcg tgtactttac ggagtatgaa aactcaggtg ccaagcggta tgctgaatgg   1980

gtattaacac cacgacaagc agcacaactt aggagaaagc tagaattctt tacctacgtc   2040

cggttcgacc tggagctgac gtttgtcata acaagtactc aacagccctc aaccacacag   2100

aaccaagacg cacagatcct aacacaccaa attatgtatg taccaccagg tggacctgta   2160

ccagataaag ttgattcata cgtgtggcaa acatctacga atcccagtgt gttttggacc   2220

gagggaaacg ccccgccgcg catgtccata ccgtttttga gcattggcaa cgcctattca   2280

aatttctatg acggatggtc tgaattttcc aggaacggag tttacggcat caacacgcta   2340

aacaacatgg gcacgctata tgcaagacat gtcaacgctg gaagcacggg tccaataaaa   2400

agcaccatta gaatctactt caaaccgaag catgtcaaag cgtggatacc tagaccacct   2460

agactctgcc aatacgagaa ggcaaagaac gtgaacttcc aacccagcgg agttaccact   2520

actaggcaaa gcatcactac aatgacaaat acgggcgcaa tttggacaac aatcaggggc   2580

agtgtatgtg gggactacag ggtagtaaat agacactcag ctaccagtgc tgactggcaa   2640

aactgtgtgt gggaaagtta caacagagac ctcttagtga gcacgaccac agcacatgga   2700

tgtgatatta tagccagatg tcagtgcaca acgggagtgt acttttgtgc gtccaaaaac   2760

aagcactacc caatttcgtt tgaaggacca ggtctagtag aggtccaaga gagtgaatac   2820

taccccagga gataccaatc ccatgtgctt ttagcagctg gattttccga accaggtgac   2880

tgtggcggta tcctaaggtg tgagcatggt gtcattggca ttgtgaccat gggggtgaa   2940

ggcgtggtcg gctttgcaga catccgtgat ctcctgtggc tggaagatga tgcaatggaa   3000
```

```
<210> SEQ ID NO 10
<211> LENGTH: 1001
<212> TYPE: PRT
<213> ORGANISM: Coxsackievirus B

<400> SEQUENCE: 10

Met Gly Ala Gln Val Ser Thr Gln Lys Thr Gly Ala His Glu Thr Arg
1               5                   10                  15

Leu Asn Ala Ser Gly Asn Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Ile Met Ile Lys Ser
    50                  55                  60
```

```
Leu Pro Ala Leu Asn Ser Pro Thr Val Glu Glu Cys Gly Tyr Ser Asp
65                  70                  75                  80

Arg Ala Arg Ser Ile Thr Leu Gly Asn Ser Thr Ile Thr Thr Gln Glu
                85                  90                  95

Cys Ala Asn Val Val Val Gly Tyr Gly Val Trp Pro Asp Tyr Leu Lys
            100                 105                 110

Asp Ser Glu Ala Thr Ala Glu Asp Gln Pro Thr Gln Pro Asp Val Ala
        115                 120                 125

Thr Cys Arg Phe Tyr Thr Leu Asp Ser Val Gln Trp Gln Lys Thr Ser
    130                 135                 140

Pro Gly Trp Trp Trp Lys Leu Pro Asp Ala Leu Ser Asn Leu Gly Leu
145                 150                 155                 160

Phe Gly Gln Asn Met Gln Tyr His Tyr Leu Gly Arg Thr Gly Tyr Thr
                165                 170                 175

Val His Val Gln Cys Asn Ala Ser Lys Phe His Gln Gly Cys Leu Leu
            180                 185                 190

Val Val Cys Val Pro Glu Ala Glu Met Gly Cys Ala Thr Leu Asp Asn
        195                 200                 205

Thr Pro Ser Ser Ala Glu Leu Leu Gly Gly Asp Thr Ala Lys Glu Phe
    210                 215                 220

Ala Asp Lys Pro Val Ala Ser Gly Ser Asn Lys Leu Val Gln Arg Val
225                 230                 235                 240

Val Tyr Asn Ala Gly Met Gly Val Gly Val Gly Asn Leu Thr Ile Phe
                245                 250                 255

Pro His Gln Trp Ile Asn Leu Arg Thr Asn Asn Ser Ala Thr Ile Val
            260                 265                 270

Met Pro Tyr Thr Asn Ser Val Pro Met Asp Asn Met Phe Arg His Asn
        275                 280                 285

Asn Val Thr Leu Met Val Ile Pro Phe Val Pro Leu Asp Tyr Cys Pro
    290                 295                 300

Gly Ser Thr Thr Tyr Val Pro Ile Thr Val Thr Ile Ala Pro Met Cys
305                 310                 315                 320

Ala Glu Tyr Asn Gly Leu Arg Leu Ala Gly His Gln Gly Leu Pro Thr
                325                 330                 335

Met Asn Thr Pro Gly Ser Cys Gln Phe Leu Thr Ser Asp Asp Phe Gln
            340                 345                 350

Ser Pro Ser Ala Met Pro Gln Tyr Asp Val Thr Pro Glu Met Arg Ile
        355                 360                 365

Pro Gly Glu Val Lys Asn Leu Met Glu Ile Ala Glu Val Asp Ser Val
    370                 375                 380

Val Pro Val Gln Asn Val Gly Glu Lys Val Asn Ser Met Glu Ala Tyr
385                 390                 395                 400

Gln Ile Pro Val Arg Ser Asn Glu Gly Ser Gly Thr Gln Val Phe Gly
                405                 410                 415

Phe Pro Leu Gln Pro Gly Tyr Ser Ser Val Phe Ser Arg Thr Leu Leu
            420                 425                 430

Gly Glu Ile Leu Asn Tyr Tyr Thr His Trp Ser Gly Ser Ile Lys Leu
        435                 440                 445

Thr Phe Met Phe Cys Gly Ser Ala Met Ala Thr Gly Lys Phe Leu Leu
    450                 455                 460

Ala Tyr Ser Pro Pro Gly Ala Gly Ala Pro Thr Lys Arg Val Asp Ala
465                 470                 475                 480

Met Leu Gly Thr His Val Ile Trp Asp Val Gly Leu Gln Ser Ser Cys
```

```
                485                 490                 495

Val Leu Cys Ile Pro Trp Ile Ser Gln Thr His Tyr Arg Phe Val Ala
            500                 505                 510

Ser Asp Glu Tyr Thr Ala Gly Gly Phe Ile Thr Cys Trp Tyr Gln Thr
        515                 520                 525

Asn Ile Val Val Pro Ala Asp Ala Gln Ser Ser Cys Tyr Ile Met Cys
    530                 535                 540

Phe Val Ser Ala Cys Asn Asp Phe Ser Val Arg Leu Leu Lys Asp Thr
545                 550                 555                 560

Pro Phe Ile Ser Gln Gln Asn Phe Phe Gln Gly Pro Val Glu Asp Ala
                565                 570                 575

Ile Thr Ala Ala Ile Gly Arg Val Ala Asp Thr Val Gly Thr Gly Pro
            580                 585                 590

Thr Asn Ser Glu Ala Ile Pro Ala Leu Thr Ala Ala Glu Thr Gly His
        595                 600                 605

Thr Ser Gln Val Val Pro Gly Asp Thr Met Gln Thr Arg His Val Lys
    610                 615                 620

Asn Tyr His Ser Arg Ser Glu Ser Thr Ile Glu Asn Phe Leu Cys Arg
625                 630                 635                 640

Ser Ala Cys Val Tyr Phe Thr Glu Tyr Lys Asn Ser Gly Ala Lys Arg
                645                 650                 655

Tyr Ala Glu Trp Val Leu Thr Pro Arg Gln Ala Ala Gln Leu Arg Arg
            660                 665                 670

Lys Leu Glu Phe Phe Thr Tyr Val Arg Phe Asp Leu Glu Leu Thr Phe
        675                 680                 685

Val Ile Thr Ser Thr Gln Gln Pro Ser Thr Thr Gln Asn Gln Asp Ala
    690                 695                 700

Gln Ile Leu Thr His Gln Ile Met Tyr Val Pro Pro Gly Gly Pro Val
705                 710                 715                 720

Pro Asp Lys Val Asp Ser Tyr Val Trp Gln Thr Ser Thr Asn Pro Ser
                725                 730                 735

Val Phe Trp Thr Glu Gly Asn Ala Pro Pro Arg Met Ser Ile Pro Phe
            740                 745                 750

Leu Ser Ile Gly Asn Ala Tyr Ser Asn Phe Tyr Asp Gly Trp Ser Glu
        755                 760                 765

Phe Ser Arg Asn Gly Val Tyr Gly Ile Asn Thr Leu Asn Asn Met Gly
    770                 775                 780

Thr Leu Tyr Ala Arg His Val Asn Ala Gly Ser Thr Gly Pro Ile Lys
785                 790                 795                 800

Ser Thr Ile Arg Ile Tyr Phe Lys Pro Lys His Val Lys Ala Trp Ile
                805                 810                 815

Pro Arg Pro Pro Arg Leu Cys Gln Tyr Glu Lys Ala Lys Asn Val Asn
            820                 825                 830

Phe Gln Pro Ser Gly Val Thr Thr Thr Arg Gln Ser Ile Thr Thr Met
        835                 840                 845

Thr Asn Thr Gly Ala Phe Gly Gln Gln Ser Gly Ala Val Tyr Val Gly
    850                 855                 860

Asn Tyr Arg Val Val Asn Arg His Leu Ala Thr Ser Ala Asp Trp Gln
865                 870                 875                 880

Asn Cys Val Trp Glu Ser Tyr Asn Arg Asp Leu Leu Val Ser Thr Thr
                885                 890                 895

Thr Ala His Gly Cys Asp Ile Ile Ala Arg Cys Gln Cys Thr Thr Gly
            900                 905                 910
```

```
Val Tyr Phe Cys Ala Ser Lys Asn Lys His Tyr Pro Ile Ser Phe Glu
        915                 920                 925

Gly Pro Gly Leu Val Glu Val Gln Glu Ser Glu Tyr Tyr Pro Arg Arg
    930                 935                 940

Tyr Gln Ser His Val Leu Leu Ala Ala Gly Phe Ser Glu Pro Gly Asp
945                 950                 955                 960

Cys Gly Gly Ile Leu Arg Cys Glu His Gly Val Ile Gly Ile Val Thr
                965                 970                 975

Met Gly Gly Glu Gly Val Val Gly Phe Ala Asp Ile Arg Asp Leu Leu
            980                 985                 990

Trp Leu Glu Asp Asp Ala Met Glu  Gln
        995                 1000
```

```
<210> SEQ ID NO 11
<211> LENGTH: 549
<212> TYPE: DNA
<213> ORGANISM: Coxsackievirus B

<400> SEQUENCE: 11

ggccctgcct ttgagttcgc cgtcgcaatg atgaaaagga actcaagcac ggtgaaaact      60

gaatatggcg agtttaccat gctgggcatc tatgacaggt gggccgtttt gccacgccac     120

gccaaacctg ggccaaccat cttgatgaat gatcaagagg ttggtgtgct agatgccaag     180

gagctagtag acaaggatgg caccaactta gaactgacac tactcgaatt gaaccggaat     240

gagaagttcg gagacatcgg aggcttcgta gccaaggagg aagtggaggt taatgaggca     300

gtgctagcaa ttaacaccag caagtttccc aacatgtaca ttccagtagg acaggtcaca     360

gaatacggct tcctaaacct aggtggcaca cccaccaaga gaatgcttat gtacaacttc     420

cccacaagag caggccagtg tggtggagtg ctcatgtcca ccggcaaggt actgggtatc     480

catgttggtg gaaatggcca tcagggcttc tcagcagcac tcctcaaaca caacttcaat     540

gatgagcaa                                                             549
```

```
<210> SEQ ID NO 12
<211> LENGTH: 180
<212> TYPE: PRT
<213> ORGANISM: Coxsackievirus B

<400> SEQUENCE: 12

Gly Pro Ala Phe Glu Phe Ala Val Ala Met Met Lys Arg Asn Ser Ser
1               5                   10                  15

Thr Val Lys Thr Glu Tyr Gly Glu Phe Thr Met Leu Gly Ile Tyr Asp
            20                  25                  30

Arg Trp Ala Val Leu Pro Arg His Ala Lys Pro Gly Pro Thr Ile Leu
        35                  40                  45

Met Asn Asp Gln Glu Val Gly Val Leu Asp Ala Lys Glu Leu Val Asp
    50                  55                  60

Lys Asp Gly Thr Asn Leu Glu Leu Thr Leu Leu Lys Leu Asn Arg Asn
65                  70                  75                  80

Glu Lys Phe Arg Asp Ile Arg Gly Phe Leu Ala Lys Glu Glu Val Glu
                85                  90                  95

Val Asn Glu Ala Val Leu Ala Ile Asn Thr Ser Lys Phe Pro Asn Met
            100                 105                 110

Tyr Ile Pro Val Gly Gln Val Thr Glu Tyr Gly Phe Leu Asn Leu Gly
        115                 120                 125
```

```
Gly Thr Pro Thr Lys Arg Met Leu Met Tyr Asn Phe Pro Thr Arg Ala
    130                 135                 140

Gly Gln Cys Gly Gly Val Leu Met Ser Thr Gly Lys Val Leu Gly Ile
145                 150                 155                 160

His Val Gly Gly Asn Gly His Gln Gly Phe Ser Ala Ala Leu Leu Lys
                165                 170                 175

His Tyr Phe Asn
            180


<210> SEQ ID NO 13
<211> LENGTH: 3717
<212> TYPE: DNA
<213> ORGANISM: artificial
<220> FEATURE:
<223> OTHER INFORMATION:
      GFP, CVB3 P1, 2a fusion protein cDNA sequence

<400> SEQUENCE: 13

atggtgagca agggcgagga gctgttcacc ggggtggtgc ccatcctggt cgagctggac      60

ggcgacgtaa acggccacaa gttcagcgtg tccggcgagg gcgagggcga tgccacctac     120

ggcaagctga ccctgaagtt catctgcacc accggcaagc tgcccgtgcc ctggcccacc     180

ctcgtgacca ccctgaccta cggcgtgcag tgcttcagcc gctaccccga ccacatgaag     240

cagcacgact tcttcaagtc cgccatgccc gaaggctacg tccaggagcg caccatcttc     300

ttcaaggacg acggcaacta caagacccgc gccgaggtga agttcgaggg cgacaccctg     360

gtgaaccgca tcgagctgaa gggcatcgac ttcaaggagg acggcaacat cctggggcac     420

aagctggagt acaactacaa cagccacaac gtctatatca tggccgacaa gcagaagaac     480

ggcatcaagg tgaacttcaa gatccgccac aacatcgagg acggcagcgt gcagctcgcc     540

gaccactacc agcagaacac ccccatcggc gacggccccg tgctgctgcc cgacaaccac     600

tacctgagca cccagtccgc cctgagcaaa gaccccaacg agaagcgcga tcacatggtc     660

ctgctggagt tcgtgaccgc cgccgggatc actctcggca tggacgagct gtacaagatg     720

ggagctcaag tatcaacgca aaagactggg gcacatgaga ccgggctgaa tgctagcggc     780

aattccatca ttcactacac aaatattaat tattacaagg atgccgcatc caactcagcc     840

aatcggcagg atttcactca agacccgggc aagttcacag aaccagtaaa agatatcatg     900

attaaatcac taccagctct caactccccc acagtagagg agtgcggata cagtgacagg     960

gcgagatcaa tcacattagg taactccacc ataacgactc aggaatgcgc caacgtggtg    1020

gtgggctatg gagtatggcc agattatcta aaggatagtg aggcaacagc agaggaccaa    1080

ccgacccaac cagacgttgc cacatgtagg ttctataccc ttgactctgt gcaatggcag    1140

aaaacctcac caggatggtg gtggaagctg cccgatgctt tgtcgaactt aggactgttt    1200

gggcagaaca tgcagtacca ctacttaggc cgaactgggt ataccgatca tgtgcagtgc    1260

aatgcatcta agttccacca aggatgcttg ctagtagtgt gtgtaccgga agctgagatg    1320

ggttgcgcaa cgctagacaa caccccatcc agtgcagaat tgctgggggg cgatacggca    1380

aaagagtttg cggacaaacc ggtcgcatcc gggtccaaca agttggtaca gagggtggtg    1440

tataatgcag gcatgggggt gggtgttgga aacctcacca ttttccccca ccaatggatc    1500

aacctacgca ccaataatag tgctacaatt gtgatgccat acaccaacag tgtacctatg    1560

gataacatgt ttaggcataa caacgtcacc ctaatggtta tcccatttgt accgctagat    1620

tactgccctg ggtccaccac gtacgtccca attacggtca cgatagcccc aatgtgtgcc    1680
```

```
gagtacaatg ggttacgttt agcagggcac cagggcttac caaccatgaa tactccgggg   1740
agctgtcaat ttctgacatc agacgacttc caatcaccat ccgccatgcc gcaatatgac   1800
gtcacaccag agatgaggat acctggtgag gtgaaaaact tgatggaaat agctgaggtt   1860
gactcagttg tcccagtcca aaatgttgga gagaaggtca actctatgga agcataccag   1920
atacctgtga gatccaatga aggatctgga acgcaagtat tcggctttcc actgcaacca   1980
gggtactcga gtgtttttag tcggacgctc ctaggagaga tcttgaacta ttatacacat   2040
tggtcaggca gcataaagct tacgtttatg ttctgtggtt cggccatggc tactggaaaa   2100
ttcctttttgg catactcacc actaggtgct ggagctccta caaaaagggt tgatgccatg   2160
cttggtactc atgtagtttg ggacgtgggg ctacaatcaa gttgcgtgct gtgtataccc   2220
tggataagcc aaacacacta ccggtatgtt gcttcagatg agtgtaccgc agggggtttt   2280
attacgtgct ggtatcaaac aaacatagtg gtcccagcgg atgcccaaag ctcctgttac   2340
atcatgtgtt tcgtgtcagc atgcaatgac ttctctgtca ggctattgaa ggacactcct   2400
ttcatttcgc aggaaaactt tttccagggc ccagtggaag acgcgataac agccgctata   2460
gggagagttg cggataccgt gggtacaggg ccaaacaact cagaagctat accagcactc   2520
actgctgctg agacaggtca cacgtcacaa gtagtgccgg gtgacaccat gcagacacgc   2580
cacgttaaga actaccattc aaggtccgag tcaaccatag agaacttcct atgtaggtca   2640
gcatgcgtgt actttacgga gtatgaaaac tcaggtgcca agcggtatgc tgaatgggta   2700
ttaacaccac gacaagcagc acaacttagg agaaagctag aattctttac ctacgtccgg   2760
ttcgacctgg agctgacgtt tgtcataaca agtactcaac agccctcaac cacacagaac   2820
caagacgcac agatcctaac acaccaaatt atgtatgtac caccaggtgg acctgtacca   2880
gataaagttg attcatacgt gtggcaaaca tctacgaatc ccagtgtgtt ttggaccgag   2940
ggaaacgccc cgccgcgcat gtccataccg tttttgagca ttggcaacgc ctattcaaat   3000
ttctatgacg gatggtctga attttccagg aacggagttt acggcatcaa cacgctaaac   3060
aacatgggca cgctatatgc aagacatgtc aacgctggaa gcacgggtcc aataaaaagc   3120
accattagaa tctacttcaa accgaagcat gtcaaagcgt ggatacctag accacctaga   3180
ctctgccaat acgagaaggc aaagaacgtg aacttccaac ccagcggagt taccactact   3240
aggcaaagca tcactacaat gacaaatacg ggcgcaattt ggacaacaat caggggcagt   3300
gtatgtgggg actacagggt agtaaataga cactcagcta ccagtgctga ctggcaaaac   3360
tgtgtgtggg aaagttacaa cagagacctc ttagtgagca cgaccacagc acatggatgt   3420
gatattatag ccagatgtca gtgcacaacg ggagtgtact tttgtgcgtc caaaaacaag   3480
cactacccaa tttcgtttga aggaccaggt ctagtagagg tccaagagag tgaatactac   3540
cccaggagat accaatccca tgtgctttta gcagctggat tttccgaacc aggtgactgt   3600
ggcggtatcc taaggtgtga gcatggtgtc attggcattg tgaccatggg gggtgaaggc   3660
gtggtcggct ttgcagacat ccgtgatctc ctgtggctgg aagatgatgc aatggaa      3717
```

```
<210> SEQ ID NO 14
<211> LENGTH: 1240
<212> TYPE: PRT
<213> ORGANISM: artificial
<220> FEATURE:
<223> OTHER INFORMATION: GFP CVB3 P1 2A fusion protein aa sequence

<400> SEQUENCE: 14

Met Val Ser Lys Gly Glu Glu Leu Phe Thr Gly Val Val Pro Ile Leu
```

```
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Met
225                 230                 235                 240

Gly Ala Gln Val Ser Thr Gln Lys Thr Gly Ala His Glu Thr Arg Leu
                245                 250                 255

Asn Ala Ser Gly Asn Ser Ile Ile His Tyr Thr Asn Ile Asn Tyr Tyr
            260                 265                 270

Lys Asp Ala Ala Ser Asn Ser Ala Asn Arg Gln Asp Phe Thr Gln Asp
        275                 280                 285

Pro Gly Lys Phe Thr Glu Pro Val Lys Asp Ile Met Ile Lys Ser Leu
    290                 295                 300

Pro Ala Leu Asn Ser Pro Thr Val Glu Glu Cys Gly Tyr Ser Asp Arg
305                 310                 315                 320

Ala Arg Ser Ile Thr Leu Gly Asn Ser Thr Ile Thr Thr Gln Glu Cys
                325                 330                 335

Ala Asn Val Val Val Gly Tyr Gly Val Trp Pro Asp Tyr Leu Lys Asp
            340                 345                 350

Ser Glu Ala Thr Ala Glu Asp Gln Pro Thr Gln Pro Asp Val Ala Thr
        355                 360                 365

Cys Arg Phe Tyr Thr Leu Asp Ser Val Gln Trp Gln Lys Thr Ser Pro
    370                 375                 380

Gly Trp Trp Trp Lys Leu Pro Asp Ala Leu Ser Asn Leu Gly Leu Phe
385                 390                 395                 400

Gly Gln Asn Met Gln Tyr His Tyr Leu Gly Arg Thr Gly Tyr Thr Val
                405                 410                 415

His Val Gln Cys Asn Ala Ser Lys Phe His Gln Gly Cys Leu Leu Val
            420                 425                 430
```

-continued

```
Val Cys Val Pro Glu Ala Glu Met Gly Cys Ala Thr Leu Asp Asn Thr
        435                 440                 445

Pro Ser Ser Ala Glu Leu Leu Gly Gly Asp Thr Ala Lys Glu Phe Ala
    450                 455                 460

Asp Lys Pro Val Ala Ser Gly Ser Asn Lys Leu Val Gln Arg Val Val
465                 470                 475                 480

Tyr Asn Ala Gly Met Gly Val Gly Val Gly Asn Leu Thr Ile Phe Pro
                485                 490                 495

His Gln Trp Ile Asn Leu Arg Thr Asn Asn Ser Ala Thr Ile Val Met
            500                 505                 510

Pro Tyr Thr Asn Ser Val Pro Met Asp Asn Met Phe Arg His Asn Asn
        515                 520                 525

Val Thr Leu Met Val Ile Pro Phe Val Pro Leu Asp Tyr Cys Pro Gly
    530                 535                 540

Ser Thr Thr Tyr Val Pro Ile Thr Val Thr Ile Ala Pro Met Cys Ala
545                 550                 555                 560

Glu Tyr Asn Gly Leu Arg Leu Ala Gly His Gln Gly Leu Pro Thr Met
                565                 570                 575

Asn Thr Pro Gly Ser Cys Gln Phe Leu Thr Ser Asp Asp Phe Gln Ser
            580                 585                 590

Pro Ser Ala Met Pro Gln Tyr Asp Val Thr Pro Glu Met Arg Ile Pro
        595                 600                 605

Gly Glu Val Lys Asn Leu Met Glu Ile Ala Glu Val Asp Ser Val Val
    610                 615                 620

Pro Val Gln Asn Val Gly Glu Lys Val Asn Ser Met Glu Ala Tyr Gln
625                 630                 635                 640

Ile Pro Val Arg Ser Asn Glu Gly Ser Gly Thr Gln Val Phe Gly Phe
                645                 650                 655

Pro Leu Gln Pro Gly Tyr Ser Ser Val Phe Ser Arg Thr Leu Leu Gly
            660                 665                 670

Glu Ile Leu Asn Tyr Tyr Thr His Trp Ser Gly Ser Ile Lys Leu Thr
        675                 680                 685

Phe Met Phe Cys Gly Ser Ala Met Ala Thr Gly Lys Phe Leu Leu Ala
    690                 695                 700

Tyr Ser Pro Pro Gly Ala Gly Ala Pro Thr Lys Arg Val Asp Ala Met
705                 710                 715                 720

Leu Gly Thr His Val Ile Trp Asp Val Gly Leu Gln Ser Ser Cys Val
                725                 730                 735

Leu Cys Ile Pro Trp Ile Ser Gln Thr His Tyr Arg Phe Val Ala Ser
            740                 745                 750

Asp Glu Tyr Thr Ala Gly Gly Phe Ile Thr Cys Trp Tyr Gln Thr Asn
        755                 760                 765

Ile Val Val Pro Ala Asp Ala Gln Ser Ser Cys Tyr Ile Met Cys Phe
    770                 775                 780

Val Ser Ala Cys Asn Asp Phe Ser Val Arg Leu Leu Lys Asp Thr Pro
785                 790                 795                 800

Phe Ile Ser Gln Gln Asn Phe Phe Gln Gly Pro Val Glu Asp Ala Ile
                805                 810                 815

Thr Ala Ala Ile Gly Arg Val Ala Asp Thr Val Gly Thr Gly Pro Thr
            820                 825                 830

Asn Ser Glu Ala Ile Pro Ala Leu Thr Ala Ala Glu Thr Gly His Thr
        835                 840                 845
```

```
Ser Gln Val Val Pro Gly Asp Thr Met Gln Thr Arg His Val Lys Asn
    850                 855                 860

Tyr His Ser Arg Ser Glu Ser Thr Ile Glu Asn Phe Leu Cys Arg Ser
865                 870                 875                 880

Ala Cys Val Tyr Phe Thr Glu Tyr Lys Asn Ser Gly Ala Lys Arg Tyr
                885                 890                 895

Ala Glu Trp Val Leu Thr Pro Arg Gln Ala Ala Gln Leu Arg Arg Lys
            900                 905                 910

Leu Glu Phe Phe Thr Tyr Val Arg Phe Asp Leu Glu Leu Thr Phe Val
        915                 920                 925

Ile Thr Ser Thr Gln Gln Pro Ser Thr Thr Gln Asn Gln Asp Ala Gln
    930                 935                 940

Ile Leu Thr His Gln Ile Met Tyr Val Pro Pro Gly Gly Pro Val Pro
945                 950                 955                 960

Asp Lys Val Asp Ser Tyr Val Trp Gln Thr Ser Thr Asn Pro Ser Val
                965                 970                 975

Phe Trp Thr Glu Gly Asn Ala Pro Pro Arg Met Ser Ile Pro Phe Leu
            980                 985                 990

Ser Ile Gly Asn Ala Tyr Ser Asn  Phe Tyr Asp Gly Trp  Ser Glu Phe
        995                 1000                1005

Ser Arg  Asn Gly Val Tyr Gly  Ile Asn Thr Leu Asn  Asn Met Gly
    1010                1015                1020

Thr Leu  Tyr Ala Arg His Val  Asn Ala Gly Ser Thr  Gly Pro Ile
    1025                1030                1035

Lys Ser  Thr Ile Arg Ile Tyr  Phe Lys Pro Lys His  Val Lys Ala
    1040                1045                1050

Trp Ile  Pro Arg Pro Pro Arg  Leu Cys Gln Tyr Glu  Lys Ala Lys
    1055                1060                1065

Asn Val  Asn Phe Gln Pro Ser  Gly Val Thr Thr Thr  Arg Gln Ser
    1070                1075                1080

Ile Thr  Thr Met Thr Asn Thr  Gly Ala Phe Gly Gln  Gln Ser Gly
    1085                1090                1095

Ala Val  Tyr Val Gly Asn Tyr  Arg Val Val Asn Arg  His Leu Ala
    1100                1105                1110

Thr Ser  Ala Asp Trp Gln Asn  Cys Val Trp Glu Ser  Tyr Asn Arg
    1115                1120                1125

Asp Leu  Leu Val Ser Thr Thr  Thr Ala His Gly Cys  Asp Ile Ile
    1130                1135                1140

Ala Arg  Cys Gln Cys Thr Thr  Gly Val Tyr Phe Cys  Ala Ser Lys
    1145                1150                1155

Asn Lys  His Tyr Pro Ile Ser  Phe Glu Gly Pro Gly  Leu Val Glu
    1160                1165                1170

Val Gln  Glu Ser Glu Tyr Tyr  Pro Arg Arg Tyr Gln  Ser His Val
    1175                1180                1185

Leu Leu  Ala Ala Gly Phe Ser  Glu Pro Gly Asp Cys  Gly Gly Ile
    1190                1195                1200

Leu Arg  Cys Glu His Gly Val  Ile Gly Ile Val Thr  Met Gly Gly
    1205                1210                1215

Glu Gly  Val Val Gly Phe Ala  Asp Ile Arg Asp Leu  Leu Trp Leu
    1220                1225                1230

Glu Asp  Asp Ala Met Glu Gln
    1235                1240
```

```
<210> SEQ ID NO 15
<211> LENGTH: 1799
<212> TYPE: DNA
<213> ORGANISM: Adenovirus

<400> SEQUENCE: 15

attcctcatg ttcttgtccc tccgcaccca ctatcttcat attgttgcag atgaaacgcg     60

ccagaccgtc tgaagacacc ttcaaccccg tgtatccata tgacacagaa accgggcctc    120

caactgtgcc ctttcttacc cctccatttg tttcacccaa tggtttccaa gaaagtcccc    180

ctggagttct ctctctacgc gtctccgaac ctttggacac ctcccacggc atgcttgcgc    240

ttaaaatggg cagcggtctt accctagaca aggccggaaa cctcacctcc caaaatgtaa    300

ccactgttac tcagccactt aaaaaaacaa agtcaaacat aagtttggac acctccgcac    360

cacttacaat tacctcaggc gccctaacag tggcaaccac cgctcctctg atagttacta    420

gcggcgctct tagcgtacag tcacaagccc cactgaccgt gcaagactcc aaactaagca    480

ttgctactaa agggcccatt acagtgtcag atggaaagct agccctgcaa acatcagccc    540

ccctctctgg cagtgacagc gacaccctta ctgtaactgc atcacccccg ctaactactg    600

ccacgggtag cttgggcatt aacatggaag atcctattta tgtaaataat ggaaaaatag    660

gaattaaaat aagcggtcct ttgcaagtag cacaaaactc cgatacacta acagtagtta    720

ctggaccagg tgtcaccgtt gaacaaaact cccttagaac caaagttgca ggagctattg    780

gttatgattc atcaaacaac atggaaatta aaacgggcgg tggcatgcgt ataaataaca    840

acttgttaat tctagatgtg gattacccat ttgatgctca aacaaaacta cgtcttaaac    900

tggggcaggg acccctgtat attaatgcat ctcataactt ggacataaac tataacagag    960

gcctatacct tttaatgca tcaaacaata ctaaaaaact ggaagttagc ataaaaaaat   1020

ccagtggact aaactttgat aatactgcca tagctataaa tgcaggaaag ggtctggagt   1080

ttgatacaaa cacatctgag tctccagata tcaacccaat aaaaactaaa attggctctg   1140

gcattgatta caatgaaaac ggtgccatga ttactaaact tggagcgggt ttaagctttg   1200

acaactcagg ggccattaca ataggaaaca aaaatgatga caaacttacc ctgtggacaa   1260

ccccagaccc atctcctaac tgcagaattc attcagataa tgactgcaaa tttactttgg   1320

ttcttacaaa atgtgggagt caagtactag ctactgtagc tgctttggct gtatctggag   1380

atctttcatc catgacaggc accgttgcaa gtgttagtat attccttaga tttgaccaaa   1440

acggtgttct aatggagaac tcctcactta aaaaacatta ctggaacttt agaaatggga   1500

actcaactaa tgcaaatcca tacacaaatg cagttggatt tatgcctaac cttctagcct   1560

atccaaaaac ccaaagtcaa actgctaaaa ataacattgt cagtcaagtt tacttgcatg   1620

gtgataaaac taaacctatg atacttacca ttacacttaa tggcactagt gaatccacag   1680

aaactagcga ggtaagcact tactctatgt cttttacatg gtcctgggaa agtggaaaat   1740

acaccactga aacttttgct accaactctt acaccttctc ctacattgcc caggaataa    1799


<210> SEQ ID NO 16
<211> LENGTH: 582
<212> TYPE: PRT
<213> ORGANISM: Adenovirus

<400> SEQUENCE: 16

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
```

```
            20                  25                  30

Phe Val Ser Pro Asn Gly Phe Gln Glu Ser Pro Pro Gly Val Leu Ser
        35                  40                  45

Leu Arg Val Ser Glu Pro Leu Asp Thr Ser His Gly Met Leu Ala Leu
    50                  55                  60

Lys Met Gly Ser Gly Leu Thr Leu Asp Lys Ala Gly Asn Leu Thr Ser
65                  70                  75                  80

Gln Asn Val Thr Thr Val Thr Gln Pro Leu Lys Lys Thr Lys Ser Asn
                85                  90                  95

Ile Ser Leu Asp Thr Ser Ala Pro Leu Thr Ile Thr Ser Gly Ala Leu
            100                 105                 110

Thr Val Ala Thr Thr Ala Pro Leu Ile Val Thr Ser Gly Ala Leu Ser
        115                 120                 125

Val Gln Ser Gln Ala Pro Leu Thr Val Gln Asp Ser Lys Leu Ser Ile
    130                 135                 140

Ala Thr Lys Gly Pro Ile Thr Val Ser Asp Gly Lys Leu Ala Leu Gln
145                 150                 155                 160

Thr Ser Ala Pro Leu Ser Gly Ser Asp Ser Asp Thr Leu Thr Val Thr
                165                 170                 175

Ala Ser Pro Pro Leu Thr Thr Ala Thr Gly Ser Leu Gly Ile Asn Met
            180                 185                 190

Glu Asp Pro Ile Tyr Val Asn Asn Gly Lys Ile Gly Ile Lys Ile Ser
        195                 200                 205

Gly Pro Leu Gln Val Ala Gln Asn Ser Asp Thr Leu Thr Val Val Thr
    210                 215                 220

Gly Pro Gly Val Thr Val Glu Gln Asn Ser Leu Arg Thr Lys Val Ala
225                 230                 235                 240

Gly Ala Ile Gly Tyr Asp Ser Ser Asn Asn Met Glu Ile Lys Thr Gly
                245                 250                 255

Gly Gly Met Arg Ile Asn Asn Asn Leu Leu Ile Leu Asp Val Asp Tyr
            260                 265                 270

Pro Phe Asp Ala Gln Thr Lys Leu Arg Leu Lys Leu Gly Gln Gly Pro
        275                 280                 285

Leu Tyr Ile Asn Ala Ser His Asn Leu Asp Ile Asn Tyr Asn Arg Gly
    290                 295                 300

Leu Tyr Leu Phe Asn Ala Ser Asn Asn Thr Lys Lys Leu Glu Val Ser
305                 310                 315                 320

Ile Lys Lys Ser Ser Gly Leu Asn Phe Asp Asn Thr Ala Ile Ala Ile
                325                 330                 335

Asn Ala Gly Lys Gly Leu Glu Phe Asp Thr Asn Thr Ser Glu Ser Pro
            340                 345                 350

Asp Ile Asn Pro Ile Lys Thr Lys Ile Gly Ser Gly Ile Asp Tyr Asn
        355                 360                 365

Glu Asn Gly Ala Met Ile Thr Lys Leu Gly Ala Gly Leu Ser Phe Asp
    370                 375                 380

Asn Ser Gly Ala Ile Thr Ile Gly Asn Lys Asn Asp Asp Lys Leu Thr
385                 390                 395                 400

Leu Trp Thr Thr Pro Asp Pro Ser Pro Asn Cys Arg Ile His Ser Asp
                405                 410                 415

Asn Asp Cys Lys Phe Thr Leu Val Leu Thr Lys Cys Gly Ser Gln Val
            420                 425                 430

Leu Ala Thr Val Ala Ala Leu Ala Val Ser Gly Asp Leu Ser Ser Met
        435                 440                 445
```

```
Thr Gly Thr Val Ala Ser Val Ser Ile Phe Leu Arg Phe Asp Gln Asn
    450                 455                 460

Gly Val Leu Met Glu Asn Ser Ser Leu Lys Lys His Tyr Trp Asn Phe
465                 470                 475                 480

Arg Asn Gly Asn Ser Thr Asn Ala Asn Pro Tyr Thr Asn Ala Val Gly
                485                 490                 495

Phe Met Pro Asn Leu Leu Ala Tyr Pro Lys Thr Gln Ser Gln Thr Ala
            500                 505                 510

Lys Asn Asn Ile Val Ser Gln Val Tyr Leu His Gly Asp Lys Thr Lys
        515                 520                 525

Pro Met Ile Leu Thr Ile Thr Leu Asn Gly Thr Ser Glu Ser Thr Glu
    530                 535                 540

Thr Ser Glu Val Ser Thr Tyr Ser Met Ser Phe Thr Trp Ser Trp Glu
545                 550                 555                 560

Ser Gly Lys Tyr Thr Thr Glu Thr Phe Ala Thr Asn Ser Tyr Thr Phe
                565                 570                 575

Ser Tyr Ile Ala Gln Glu
            580


<210> SEQ ID NO 17
<211> LENGTH: 5247
<212> TYPE: DNA
<213> ORGANISM: Homo sapiens

<400> SEQUENCE: 17

atgtccgcca gagctgcggc cgccaagagc acagcaatgg aggaaacagc tatatgggaa      60

caacatacag tgacgcttca cagggctcct ggatttggat ttggaattgc aatatctggt     120

ggacgagata atcctcattt tcagagtggg gaaacgtcaa tagtgatttc agatgtgctg     180

aaaggaggac cagctgaagg acagctacag gaaaatgacc gagttgcaat ggttaacgga     240

gtttcaatgg ataatgttga acatgctttt gctgttcagc aactaaggaa aagtgggaaa     300

aatgcaaaaa ttacaattag aaggaagaag aaagttcaaa taccagtaag tcgtcctgat     360

cctgaaccag tatctgataa tgaagaagat agttatgatg aggaaataca tgatccaaga     420

agtggccgga gtggtgtggt taacagaagg agtgagaaga tttggccgag ggatagaagt     480

gcaagtagag agaggagctt gtccccgcgg tcagacaggc ggtcagtggc ttccagccag     540

cctgctaaac ctactaaagt cacactggtg aaatcccgga aaaatgaaga atatggtctt     600

cgattggcaa gccatatatt tgttaaggaa atttcacaag atagtttggc agcaagagat     660

ggcaatattc aagaaggtga tgttgtattg aagataaatg gtactgtgac agaaaatatg     720

tcattgacag atgcaaagac attgatagaa aggtctaaag gcaaattaaa aatggtagtt     780

caaagagatg aacgggctac gctattgaat gtccctgatc tttctgacag catccactct     840

gctaatgcct ctgagagaga cgacatttca gaaattcagt cactggcatc agatcattct     900

ggtcgatcac acgataggcc tccccgccgc agccggtcac gatctcctga ccagcggtca     960

gagccttctg atcattccag gcactcgccg cagcagccaa gcaatggcag tctccggagt    1020

agagatgaag agagaatttc taaacctggg gctgtctcaa ctcctgtaaa gcatgctgat    1080

gatcacacac ctaaaacagt ggaagaagtt acagttgaaa gaaatgagaa acaaaacacct   1140

tctcttccag aaccaaagcc tgtgtatgcc caagttgggc aaccagatgt ggatttacct    1200

gtcagtccat ctgatggtgt cctacctaat tcaactcatg aagatgggat tcttcggccc    1260

agcatgaaat tggtaaaatt cagaaaagga gatagtgtgg gtttgcggct ggctggtgga    1320
```

```
aatgatgttg gaatatttgt agctggcgtt ctagaagata gccctgcagc caaggaaggc   1380
ttagaggaag gtgatcaaat tctcagggta aacaacgtag attttacaaa tatcataaga   1440
gaagaagccg tccttttcct gcttgacctc cctaaaggag aagaagtgac catattggct   1500
cagaagaaga aggatgttta tcgtcgcatt gtagaatcag atgtaggaga ttctttctat   1560
attagaaccc attttgaata tgaaaaggaa tctccctatg gacttagttt taacaaagga   1620
gaggtgttcc gtgttgtgga taccttgtac aatggaaaac tgggctcttg gcttgctatt   1680
cgaattggta aaaatcataa ggaggtagaa cgaggcatca tccctaataa gaacagagct   1740
gagcagctag ccagtgtaca gtatacactt ccaaaaacag caggcggaga ccgtgctgac   1800
ttctggagat tcagaggtct tcgcagctcc aagagaaatc ttcgaaaaag cagagaggat   1860
ttgtccgctc agcctgttca aacaaagttt ccagcttatg aaagagtggt tcttcgagaa   1920
gctggatttc tgaggcctgt aaccattttt ggaccaatag ctgatgttgc cagagaaaag   1980
ctggcaagag aagaaccaga tatttatcaa attgcaaaga gtgaaccacg agacgctgga   2040
actgaccaac gtagctctgg cattattcgc ctgcatacaa taaagcaaat catagatcaa   2100
gacaaacatg ctttattaga tgtaacacca aatgcagttg atcgtcttaa ctatgcccag   2160
tggtatccaa ttgttgtatt tcttaaccct gattctaagc aaggagtaaa aacaatgaga   2220
atgaggttat gtccagaatc tcggaaaagt gccaggaagt tatacgagcg atctcataaa   2280
cttcgtaaaa ataatcacca tctttttaca actacaatta acttaaattc aatgaatgat   2340
ggttggtatg gtgcgctgaa agaagcaatt caacaacagc aaaaccagct ggtatgggtt   2400
tccgagggaa aggcggatgg tgctacaagt gatgaccttg atttgcatga tgatcgtctg   2460
tcctacctgt cagctccagg tagtgaatac tcaatgtata gcacggacag tagacacact   2520
tctgactatg aagacacaga cacagaaggc ggggcctaca ctgatcaaga actagatgaa   2580
actcttaatg atgaggttgg gactccaccg gagtctgcca ttacacggtc ctctgagcct   2640
gtaagagagg actcctctgg aatgcatcat gaaaaccaaa catatcctcc ttactcacca   2700
caagcgcagc cacaaccaat tcatagaata gactcccctg gatttaagcc agcctctcaa   2760
cagaaagcag aagcttcatc tccagtccct tacctttcgc ctgaaacaaa cccagcatca   2820
tcaacctctg ctgttaatca taatgtaaat ttaactaatg tcagactgga ggagcccacc   2880
ccagctcctt ccacctctta ctcaccacaa gctgattctt taagaacacc aagtactgag   2940
gcagctcaca taatgctaag agatcaagaa ccatcattgt cgtcgcatgt agatccaaca   3000
aaggtgtata gaaaggatcc atatcccgag gaaatgatga ggcagaacca tgttttgaaa   3060
cagccagccg ttagtcaccc agggcacagg ccagacaaag agcctaatct gacctatgaa   3120
ccccaactcc catacgtaga gaaacaagcc agcagagacc tcgagcagcc cacatacaga   3180
tacgagtcct caagctatac ggaccagttt tctcgaaact atgaacatcg tctgcgatac   3240
gaagatcgcg tccccatgta tgaagaacag tggtcatatt atgatgacaa acagccctac   3300
ccatctcggc cacctttga taatcagcac tctcaagacc ttgactccag acagcatccc   3360
gaagagtcct cagaacgagg gtactttcca cgttttgaag agccagcccc tctgtcttac   3420
gacagcagac cacgttacga acaggcacct agagcatccg ccctgcggca cgaagagcag   3480
ccagctcctg ggtatgacac acatggtaga ctcagaccgg aagcccagcc ccacccttca   3540
gcagggccca agcctgcaga gtccaagcag tattttgagc aatattcacg cagttacgag   3600
caagtaccac cccaaggatt tacctctaga gcaggtcatt ttgagcctct ccatggtgct   3660
```

```
gcagctgtcc ctccgctgat accttcatct cagcataagc cagaagctct gccttcaaac   3720

accaaaccac tgcctccacc cccaactcaa accgaagaag aggaagatcc agcaatgaag   3780

ccacagtctg tactcaccag agttaagatg tttgaaaaca aaagatctgc atccttagag   3840

accaagaagg atgtaaatga cactggcagt tttaagcctc cagaagtagc atctaaacct   3900

tcaggtgctc ccatcattgg tcccaaaccc acttctcaga atcaattcag tgaacatgac   3960

aaaactctgt acaggatccc agaacctcaa aaacctcaac tgaagccacc tgaagatatt   4020

gttcggtcca atcattatga ccctgaagaa gatgaagaat attatcgaaa acagctgtca   4080

tactttgacc gaagaagttt tgagaataag cctcctgcac acattgccgc cagccatctc   4140

tccgagcctg caaagccagc gcattctcag aatcaatcaa atttttctag ttattcttca   4200

aagggaaagc ctcctgaagc tgatggtgtg gatagatcat ttggcgagaa acgctatgaa   4260

cccatccagg ccactccccc tcctcctcca ttgccctcgc agtatgccca gccatctcag   4320

cctgtcacca gcgcgtctct ccacatacat tctaagggag cacatggtga aggtaattca   4380

gtgtcattgg attttcagaa ttccttagtg tccaaaccag acccacctcc atctcagaat   4440

aagccagcaa ctttcagacc accaaaccga gaagatactg ctcaggcagc tttctatccc   4500

cagaaaagtt ttccagataa agccccagtt aatggaactg aacagactca gaaaacagtc   4560

actccagcat acaatcgatt cacaccaaaa ccatatacaa gttctgcccg accatttgaa   4620

cgcaagtttg aaagtcctaa attcaatcac aatcttctgc caagtgaaac tgcacataaa   4680

cctgacttgt cttcaaaaac tcccacttct ccaaaaactc ttgtgaaatc gcacagtttg   4740

gcacagcctc ctgagtttga cagtggagtt gaaactttct ctatccatgc agagaagcct   4800

aaatatcaaa taaataatat cagcacagtg cctaaagcta ttcctgtgag tccttcagct   4860

gtggaagagg atgaagatga agatggtcat actgtggtgg ccacagcccg aggcatattt   4920

aacagcaatg gggcgtgct gagttccata gaaactggtg ttagtataat tatccctcaa   4980

ggagccattc ccgaaggagt tgagcaggaa atctatttca aggtctgccg ggacaacagc   5040

atccttccac ctttagataa agagaaaggt gaaacactgc tgagtccttt ggtgatgtgt   5100

ggtccccatg gcctcaagtt cctgaagcct gtggagctgc gcttaccaca ctgtgatcct   5160

aaaacctggc aaaacaagtg tcttcccgga gatccaaatt atctcgttgg agcaaactgt   5220

gtttctgtcc ttattgacca cttttaa                                       5247
```

<210> SEQ ID NO 18
<211> LENGTH: 1748
<212> TYPE: PRT
<213> ORGANISM: Homo sapiens

<400> SEQUENCE: 18

```
Met Ser Ala Arg Ala Ala Ala Ala Lys Ser Thr Ala Met Glu Glu Thr
1               5                   10                  15

Ala Ile Trp Glu Gln His Thr Val Thr Leu His Arg Ala Pro Gly Phe
            20                  25                  30

Gly Phe Gly Ile Ala Ile Ser Gly Gly Arg Asp Asn Pro His Phe Gln
        35                  40                  45

Ser Gly Glu Thr Ser Ile Val Ile Ser Asp Val Leu Lys Gly Gly Pro
    50                  55                  60

Ala Glu Gly Gln Leu Gln Glu Asn Asp Arg Val Ala Met Val Asn Gly
65                  70                  75                  80

Val Ser Met Asp Asn Val Glu His Ala Phe Ala Val Gln Gln Leu Arg
                85                  90                  95
```

```
Lys Ser Gly Lys Asn Ala Lys Ile Thr Ile Arg Arg Lys Lys Lys Val
            100                 105                 110

Gln Ile Pro Val Ser Arg Pro Asp Pro Glu Pro Val Ser Asp Asn Glu
        115                 120                 125

Glu Asp Ser Tyr Asp Glu Glu Ile His Asp Pro Arg Ser Gly Arg Ser
    130                 135                 140

Gly Val Val Asn Arg Arg Ser Glu Lys Ile Trp Pro Arg Asp Arg Ser
145                 150                 155                 160

Ala Ser Arg Glu Arg Ser Leu Ser Pro Arg Ser Asp Arg Arg Ser Val
                165                 170                 175

Ala Ser Ser Gln Pro Ala Lys Pro Thr Lys Val Thr Leu Val Lys Ser
            180                 185                 190

Arg Lys Asn Glu Glu Tyr Gly Leu Arg Leu Ala Ser His Ile Phe Val
        195                 200                 205

Lys Glu Ile Ser Gln Asp Ser Leu Ala Ala Arg Asp Gly Asn Ile Gln
    210                 215                 220

Glu Gly Asp Val Val Leu Lys Ile Asn Gly Thr Val Thr Glu Asn Met
225                 230                 235                 240

Ser Leu Thr Asp Ala Lys Thr Leu Ile Glu Arg Ser Lys Gly Lys Leu
                245                 250                 255

Lys Met Val Val Gln Arg Asp Glu Arg Ala Thr Leu Leu Asn Val Pro
            260                 265                 270

Asp Leu Ser Asp Ser Ile His Ser Ala Asn Ala Ser Glu Arg Asp Asp
        275                 280                 285

Ile Ser Glu Ile Gln Ser Leu Ala Ser Asp His Ser Gly Arg Ser His
    290                 295                 300

Asp Arg Pro Pro Arg Arg Ser Arg Ser Arg Ser Pro Asp Gln Arg Ser
305                 310                 315                 320

Glu Pro Ser Asp His Ser Arg His Ser Pro Gln Gln Pro Ser Asn Gly
                325                 330                 335

Ser Leu Arg Ser Arg Asp Glu Glu Arg Ile Ser Lys Pro Gly Ala Val
            340                 345                 350

Ser Thr Pro Val Lys His Ala Asp Asp His Thr Pro Lys Thr Val Glu
        355                 360                 365

Glu Val Thr Val Glu Arg Asn Glu Lys Gln Thr Pro Ser Leu Pro Glu
    370                 375                 380

Pro Lys Pro Val Tyr Ala Gln Val Gly Gln Pro Asp Val Asp Leu Pro
385                 390                 395                 400

Val Ser Pro Ser Asp Gly Val Leu Pro Asn Ser Thr His Glu Asp Gly
                405                 410                 415

Ile Leu Arg Pro Ser Met Lys Leu Val Lys Phe Arg Lys Gly Asp Ser
            420                 425                 430

Val Gly Leu Arg Leu Ala Gly Gly Asn Asp Val Gly Ile Phe Val Ala
        435                 440                 445

Gly Val Leu Glu Asp Ser Pro Ala Ala Lys Glu Gly Leu Glu Glu Gly
    450                 455                 460

Asp Gln Ile Leu Arg Val Asn Asn Val Asp Phe Thr Asn Ile Ile Arg
465                 470                 475                 480

Glu Glu Ala Val Leu Phe Leu Leu Asp Leu Pro Lys Gly Glu Glu Val
                485                 490                 495

Thr Ile Leu Ala Gln Lys Lys Lys Asp Val Tyr Arg Arg Ile Val Glu
            500                 505                 510
```

```
Ser Asp Val Gly Asp Ser Phe Tyr Ile Arg Thr His Phe Glu Tyr Glu
        515                 520                 525

Lys Glu Ser Pro Tyr Gly Leu Ser Phe Asn Lys Gly Glu Val Phe Arg
    530                 535                 540

Val Val Asp Thr Leu Tyr Asn Gly Lys Leu Gly Ser Trp Leu Ala Ile
545                 550                 555                 560

Arg Ile Gly Lys Asn His Lys Glu Val Glu Arg Gly Ile Ile Pro Asn
                565                 570                 575

Lys Asn Arg Ala Glu Gln Leu Ala Ser Val Gln Tyr Thr Leu Pro Lys
            580                 585                 590

Thr Ala Gly Gly Asp Arg Ala Asp Phe Trp Arg Phe Arg Gly Leu Arg
        595                 600                 605

Ser Ser Lys Arg Asn Leu Arg Lys Ser Arg Glu Asp Leu Ser Ala Gln
    610                 615                 620

Pro Val Gln Thr Lys Phe Pro Ala Tyr Glu Arg Val Val Leu Arg Glu
625                 630                 635                 640

Ala Gly Phe Leu Arg Pro Val Thr Ile Phe Gly Pro Ile Ala Asp Val
                645                 650                 655

Ala Arg Glu Lys Leu Ala Arg Glu Glu Pro Asp Ile Tyr Gln Ile Ala
            660                 665                 670

Lys Ser Glu Pro Arg Asp Ala Gly Thr Asp Gln Arg Ser Ser Gly Ile
        675                 680                 685

Ile Arg Leu His Thr Ile Lys Gln Ile Ile Asp Gln Asp Lys His Ala
    690                 695                 700

Leu Leu Asp Val Thr Pro Asn Ala Val Asp Arg Leu Asn Tyr Ala Gln
705                 710                 715                 720

Trp Tyr Pro Ile Val Val Phe Leu Asn Pro Asp Ser Lys Gln Gly Val
                725                 730                 735

Lys Thr Met Arg Met Arg Leu Cys Pro Glu Ser Arg Lys Ser Ala Arg
            740                 745                 750

Lys Leu Tyr Glu Arg Ser His Lys Leu Arg Lys Asn Asn His His Leu
        755                 760                 765

Phe Thr Thr Thr Ile Asn Leu Asn Ser Met Asn Asp Gly Trp Tyr Gly
    770                 775                 780

Ala Leu Lys Glu Ala Ile Gln Gln Gln Gln Asn Gln Leu Val Trp Val
785                 790                 795                 800

Ser Glu Gly Lys Ala Asp Gly Ala Thr Ser Asp Asp Leu Asp Leu His
                805                 810                 815

Asp Asp Arg Leu Ser Tyr Leu Ser Ala Pro Gly Ser Glu Tyr Ser Met
            820                 825                 830

Tyr Ser Thr Asp Ser Arg His Thr Ser Asp Tyr Glu Asp Thr Asp Thr
        835                 840                 845

Glu Gly Gly Ala Tyr Thr Asp Gln Glu Leu Asp Glu Thr Leu Asn Asp
    850                 855                 860

Glu Val Gly Thr Pro Pro Glu Ser Ala Ile Thr Arg Ser Ser Glu Pro
865                 870                 875                 880

Val Arg Glu Asp Ser Ser Gly Met His His Glu Asn Gln Thr Tyr Pro
                885                 890                 895

Pro Tyr Ser Pro Gln Ala Gln Pro Gln Pro Ile His Arg Ile Asp Ser
            900                 905                 910

Pro Gly Phe Lys Pro Ala Ser Gln Gln Lys Ala Glu Ala Ser Ser Pro
        915                 920                 925

Val Pro Tyr Leu Ser Pro Glu Thr Asn Pro Ala Ser Ser Thr Ser Ala
```

```
    930                 935                 940

Val Asn His Asn Val Asn Leu Thr Asn Val Arg Leu Glu Glu Pro Thr
945                 950                 955                 960

Pro Ala Pro Ser Thr Ser Tyr Ser Pro Gln Ala Asp Ser Leu Arg Thr
                965                 970                 975

Pro Ser Thr Glu Ala Ala His Ile Met Leu Arg Asp Gln Glu Pro Ser
            980                 985                 990

Leu Ser Ser His Val Asp Pro Thr  Lys Val Tyr Arg Lys  Asp Pro Tyr
        995                 1000                1005

Pro Glu  Glu Met Met Arg Gln  Asn His Val Leu Lys  Gln Pro Ala
    1010                 1015                 1020

Val Ser  His Pro Gly His Arg  Pro Asp Lys Glu Pro  Asn Leu Thr
    1025                 1030                 1035

Tyr Glu  Pro Gln Leu Pro Tyr  Val Glu Lys Gln Ala  Ser Arg Asp
    1040                 1045                 1050

Leu Glu  Gln Pro Thr Tyr Arg  Tyr Glu Ser Ser Ser  Tyr Thr Asp
    1055                 1060                 1065

Gln Phe  Ser Arg Asn Tyr Glu  His Arg Leu Arg Tyr  Glu Asp Arg
    1070                 1075                 1080

Val Pro  Met Tyr Glu Glu Gln  Trp Ser Tyr Tyr Asp  Asp Lys Gln
    1085                 1090                 1095

Pro Tyr  Pro Ser Arg Pro Pro  Phe Asp Asn Gln His  Ser Gln Asp
    1100                 1105                 1110

Leu Asp  Ser Arg Gln His Pro  Glu Glu Ser Ser Glu  Arg Gly Tyr
    1115                 1120                 1125

Phe Pro  Arg Phe Glu Glu Pro  Ala Pro Leu Ser Tyr  Asp Ser Arg
    1130                 1135                 1140

Pro Arg  Tyr Glu Gln Ala Pro  Arg Ala Ser Ala Leu  Arg His Glu
    1145                 1150                 1155

Glu Gln  Pro Ala Pro Gly Tyr  Asp Thr His Gly Arg  Leu Arg Pro
    1160                 1165                 1170

Glu Ala  Gln Pro His Pro Ser  Ala Gly Pro Lys Pro  Ala Glu Ser
    1175                 1180                 1185

Lys Gln  Tyr Phe Glu Gln Tyr  Ser Arg Ser Tyr Glu  Gln Val Pro
    1190                 1195                 1200

Pro Gln  Gly Phe Thr Ser Arg  Ala Gly His Phe Glu  Pro Leu His
    1205                 1210                 1215

Gly Ala  Ala Ala Val Pro Pro  Leu Ile Pro Ser Ser  Gln His Lys
    1220                 1225                 1230

Pro Glu  Ala Leu Pro Ser Asn  Thr Lys Pro Leu Pro  Pro Pro Pro
    1235                 1240                 1245

Thr Gln  Thr Glu Glu Glu Glu  Asp Pro Ala Met Lys  Pro Gln Ser
    1250                 1255                 1260

Val Leu  Thr Arg Val Lys Met  Phe Glu Asn Lys Arg  Ser Ala Ser
    1265                 1270                 1275

Leu Glu  Thr Lys Lys Asp Val  Asn Asp Thr Gly Ser  Phe Lys Pro
    1280                 1285                 1290

Pro Glu  Val Ala Ser Lys Pro  Ser Gly Ala Pro Ile  Ile Gly Pro
    1295                 1300                 1305

Lys Pro  Thr Ser Gln Asn Gln  Phe Ser Glu His Asp  Lys Thr Leu
    1310                 1315                 1320

Tyr Arg  Ile Pro Glu Pro Gln  Lys Pro Gln Leu Lys  Pro Pro Glu
    1325                 1330                 1335
```

```
Asp Ile  Val Arg Ser Asn His  Tyr Asp Pro Glu Glu  Asp Glu Glu
    1340                 1345                 1350

Tyr Tyr  Arg Lys Gln Leu Ser  Tyr Phe Asp Arg Arg  Ser Phe Glu
    1355                 1360                 1365

Asn Lys  Pro Pro Ala His Ile  Ala Ala Ser His Leu  Ser Glu Pro
    1370                 1375                 1380

Ala Lys  Pro Ala His Ser Gln  Asn Gln Ser Asn Phe  Ser Ser Tyr
    1385                 1390                 1395

Ser Ser  Lys Gly Lys Pro Pro  Glu Ala Asp Gly Val  Asp Arg Ser
    1400                 1405                 1410

Phe Gly  Glu Lys Arg Tyr Glu  Pro Ile Gln Ala Thr  Pro Pro Pro
    1415                 1420                 1425

Pro Pro  Leu Pro Ser Gln Tyr  Ala Gln Pro Ser Gln  Pro Val Thr
    1430                 1435                 1440

Ser Ala  Ser Leu His Ile His  Ser Lys Gly Ala His  Gly Glu Gly
    1445                 1450                 1455

Asn Ser  Val Ser Leu Asp Phe  Gln Asn Ser Leu Val  Ser Lys Pro
    1460                 1465                 1470

Asp Pro  Pro Pro Ser Gln Asn  Lys Pro Ala Thr Phe  Arg Pro Pro
    1475                 1480                 1485

Asn Arg  Glu Asp Thr Ala Gln  Ala Ala Phe Tyr Pro  Gln Lys Ser
    1490                 1495                 1500

Phe Pro  Asp Lys Ala Pro Val  Asn Gly Thr Glu Gln  Thr Gln Lys
    1505                 1510                 1515

Thr Val  Thr Pro Ala Tyr Asn  Arg Phe Thr Pro Lys  Pro Tyr Thr
    1520                 1525                 1530

Ser Ser  Ala Arg Pro Phe Glu  Arg Lys Phe Glu Ser  Pro Lys Phe
    1535                 1540                 1545

Asn His  Asn Leu Leu Pro Ser  Glu Thr Ala His Lys  Pro Asp Leu
    1550                 1555                 1560

Ser Ser  Lys Thr Pro Thr Ser  Pro Lys Thr Leu Val  Lys Ser His
    1565                 1570                 1575

Ser Leu  Ala Gln Pro Pro Glu  Phe Asp Ser Gly Val  Glu Thr Phe
    1580                 1585                 1590

Ser Ile  His Ala Glu Lys Pro  Lys Tyr Gln Ile Asn  Asn Ile Ser
    1595                 1600                 1605

Thr Val  Pro Lys Ala Ile Pro  Val Ser Pro Ser Ala  Val Glu Glu
    1610                 1615                 1620

Asp Glu  Asp Glu Asp Gly His  Thr Val Val Ala Thr  Ala Arg Gly
    1625                 1630                 1635

Ile Phe  Asn Ser Asn Gly Gly  Val Leu Ser Ser Ile  Glu Thr Gly
    1640                 1645                 1650

Val Ser  Ile Ile Ile Pro Gln  Gly Ala Ile Pro Glu  Gly Val Glu
    1655                 1660                 1665

Gln Glu  Ile Tyr Phe Lys Val  Cys Arg Asp Asn Ser  Ile Leu Pro
    1670                 1675                 1680

Pro Leu  Asp Lys Glu Lys Gly  Glu Thr Leu Leu Ser  Pro Leu Val
    1685                 1690                 1695

Met Cys  Gly Pro His Gly Leu  Lys Phe Leu Lys Pro  Val Glu Leu
    1700                 1705                 1710

Arg Leu  Pro His Cys Asp Pro  Lys Thr Trp Gln Asn  Lys Cys Leu
    1715                 1720                 1725
```

```
Pro Gly  Asp Pro Asn Tyr Leu  Val Gly Ala Asn Cys  Val Ser Val
    1730                1735                1740

Leu Ile  Asp His Phe
    1745


<210> SEQ ID NO 19
<211> LENGTH: 6129
<212> TYPE: DNA
<213> ORGANISM: Homo sapiens

<400> SEQUENCE: 19

atgttggaag ccattgacaa aaatcgggcc ctgcatgcag cagagcgctt gcaaaccaag     60

ctgcgagaac gtggggatgt agcaaatgaa gacaaactga gccttctgaa gtcagtcctg    120

cagagccctc tcttcagtca gattctgagc cttcagactt ctgtacagca gctgaaagac    180

caggtaaata ttgcaacttc agcaacttca aatattgaat atgcccacgt tcctcatctc    240

agcccagctg tgattcctac tctgcaaaat gaatcgtttt tattatcccc aaacaatggg    300

aatctggaag cacttacagg acctggtatt ccacacatta atgggaaacc tgcttgtgat    360

gaatttgatc agcttatcaa aaatatggcc cagggtcgcc atgtagaagt tttgagctc     420

ctcaaacctc catctggagg ccttgggttt agtgttgtgg gactaagaag tgaaaacaga    480

ggagagctgg gaatatttgt tcaagagata caagagggca gtgtggccca tagagatgga    540

agattgaaag aaactgatca aattcttgct atcaatggac aggctcttga tcagacaatt    600

acacatcagc aggctatcag catcctgcag aaagccaaag atactgtcca gctagttatt    660

gccagaggct cattgcctca gcttgtcagc cccatagttt cccgttctcc atctgcagcc    720

agcacaattt cagctcactc taatccggtt cactggcaac acatggaaac gattgaattg    780

gtgaatgatg gatctggttt gggatttggc atcataggag gaaaagcaac tggtgtgata    840

gtaaaaacca ttctgcctgg aggagtagct gatcagcatg ggcgtttatg cagtggagac    900

cacattctaa agattggtga cacagatcta gcaggaatga gcagtgagca agtagcacaa    960

gtccttaggc aatgtggaaa tagagttaag ttgatgattg caagaggtgc catagaagaa   1020

cgtacagcac ccactgcttt gggcatcacc ctctcctcat ccccaacttc aacaccagag   1080

ttgcgggttg atgcttctac tcagaaaggt gaagaaagtg agacatttga tgtagaactc   1140

actaaaaatg tccaaggatt aggaattacc attgctggct acattggaga taaaaaattg   1200

gaaccttcag gaatctttgt aaagagcatt acaaaaagca gtgccgttga gcatgatgga   1260

agaatccaaa ttggagacca aattatagca gtagatggca caaaccttca gggttttact   1320

aatcagcaag cagtagaggt attgcgacat acaggacaaa ctgtgctcct gacactaatg   1380

aggagaggaa tgaagcagga agccgagctc atgtcaaggg aagacgtcac aaaagatgca   1440

gatttgtctc ctgttaatgc cagcataatc aaagaaaatt atgaaaaaga tgaagatttt   1500

ttatcttcga cgagaaacac caacatatta ccaactgaag aagaagggta tccattactg   1560

tcagctgaga tagaagaaat agaagatgca caaaaacaag aagctgctct gctgacaaaa   1620

tggcaaagga ttatgggaat taactatgaa atagtggtgg cccatgtgag caagtttagt   1680

gagaacagtg gattggggat aagcctggaa gcgacagtgg gacatcattt tatccgatct   1740

gttctaccag agggtcctgt tggacacagc gggaagctct tcagtggaga cgagctattg   1800

gaagtaaatg gcataacttt acttggggaa aatcaccaag atgtggtgaa tatcttaaaa   1860

gaactgccta tagaagtgac aatggtgtgc tgtcgtcgaa ctgtgccacc caccacccaa   1920

tcagaattgg atagcctgga cttatgtgat attgagctaa cagaaaagcc tcacgtagat   1980
```

-continued

```
ctaggtgagt tcatcgggtc atcagagaca gaggatccag tgctggcgat gactgatgcg   2040
ggtcagagta cagaagaggt tcaagcacct ttggccatgt gggaggctgg cattcagcac   2100
atagagctgg agaaagggag caaaggactt ggttttagca ttttagatta tcaggatcca   2160
attgatccag caagcactgt gattataatt cgttctttgg tgcctggcgg cattgctgaa   2220
aaggatggac gacttcttcc tggtgaccga ctcatgtttg taaacgatgt taacttggaa   2280
aacagcagtc ttgaggaagc tgtagaagca ctgaagggag caccgtcagg gactgtgaga   2340
ataggagttg ctaagccttt accccttca ccagaagaag gttatgtttc tgctaaggag   2400
gattcctttc tctacccacc acactcctgt gaggaagcag ggctggctga caaacccctc   2460
ttcagggctg acttggctct ggtgggcaca aatgatgctg acttagtaga tgaatccaca   2520
tttgagtctc catactctcc tgaaaatgac agcatctact ctactcaagc ctctatttta   2580
tctcttcatg gcagttcttg tggtgatggc ctgaactatg gttcttccct tccatcatct   2640
cctcctaagg atgttattga aaattcttgt gatccagtac ttgatctgca tatgtctctg   2700
gaggaactat atacccagaa tctcctgcaa agacaggatg agaatacacc ttcggtggac   2760
ataagtatgg ggcctgcttc tggctttact ataaatgact acacacctgc aaatgctatt   2820
gaacaacaat atgaatgtga aaacacaata gtgtggactg aatctcattt accaagtgaa   2880
gttatatcaa gtgcagaact tccttctgtg ctacccgatt cagctggaaa gggctctgag   2940
tacctgcttg aacagagctc cctggcctgt aatgctgagt gtgtcatgct tcaaaatgta   3000
tctaaagaat cttttgaaag gactattaat atagcaaaag gcaattctag cctaggaatg   3060
acagttagtg ctaataaaga tggcttgggg atgatcgttc gaagcattat tcatggaggt   3120
gccattagtc gagatggccg gattgccatt ggggactgca tcttgtccat taatgaagag   3180
tctaccatca gtgtaaccaa tgcccaggca cgagctatgt tgagaagaca ttctctcatt   3240
ggccctgaca taaaaattac ttatgtgcct gcagaacatt tggaagagtt caaaataagc   3300
ttgggacaac aatctggaag agtaatggca ctggatattt tttcttcata cactggcaga   3360
gacattccag aattaccaga gcgagaagag ggagagggtg aagaaagcga acttcaaaac   3420
acagcatata gcaattggaa tcagcccagg cgggtggaac tctggagaga accaagcaaa   3480
tccttaggca tcagcattgt tggtggacga gggatgggga gtcggctaag caatggagaa   3540
gtgatgaggg gcattttcat caaacatgtt ctggaagata gtccagctgg caaaaatgga   3600
accttgaaac ctggagatag aatcgtagag gtggatggaa tggacctcag agatgcaagc   3660
catgaacaag ctgtggaagc cattcggaaa gcaggcaacc ctgtagtctt tatggtacag   3720
agcattataa acagaccaag gaaatcccct ttgccttcct tgctgcacaa cctttaccct   3780
aagtacaact tcagcagcac taacccattt gctgactctc tacaaatcaa cgccgacaag   3840
gcacccagtc agtcagagtc agagccagag aaggctccat tgtgcagtgt gcccccaccc   3900
cctccttcag cctttgccga aatgggtagt gatcacacac agtcatctgc aagcaaaatc   3960
tcacaagatg tggacaaaga ggatgagttt ggttacagct ggaaaaatat cagagagcgt   4020
tatggaaccc taacaggcga gctgcatatg attgaactgg agaaaggtca tagtggtttg   4080
ggcctaagtc ttgctgggaa caaagaccga tccaggatga gtgtcttcat agtggggatt   4140
gatccaaatg gagctgcagg aaaagatggt cgattgcaaa ttgcagatga gcttctagag   4200
atcaatggtc agattttata tggaagaagt catcagaatg cctcatcaat cattaaatgt   4260
gccccttcta aagtgaaaat aatttttatc agaaataaag atgcagtgaa tcagatggcc   4320
```

-continued

```
gtatgtcctg gaaatgcagt agaacctttg ccttctaact cagaaaatct tcaaaataag   4380

gagacagagc caactgttac tacttctgat gcagctgtgg acctcagttc atttaaaaat   4440

gtgcaacatc tggagcttcc caaggatcag gggggtttgg gtattgctat cagcgaagaa   4500

gatacactca gtggagtcat cataaagagc ttaacagagc atggggtagc agccacggat   4560

ggacgactca aagtcggaga tcagatactg gctgtagatg atgaaattgt tgttggttac   4620

cctattgaaa agtttattag ccttctgaag acagcaaaga tgacagtaaa acttaccatc   4680

catgctgaga atccagattc ccaggctgtt ccttcagcag ctggtgcagc cagtggagaa   4740

aaaaagaaca gctcccagtc tctgatggtc ccacagtctg gctccccaga accggagtcc   4800

atccgaaata caagcagatc atcaacacca gcaatttttg cttctgatcc tgcaacctgc   4860

cccattatcc ctggctgcga aacaaccatc gagatttcca aagggcgaac agggctgggc   4920

ctgagcatcg ttggggggttc agacacgctg ctgggtgcca ttattatcca tgaagtttat   4980

gaagaaggag cagcatgtaa agatggaaga ctctgggctg gagatcagat cttagaggtg   5040

aatggaattg acttgagaaa ggccacacat gatgaagcaa tcaatgtcct gagacagacg   5100

ccacagagag tgcgcctgac actctacaga gatgaggccc catacaaaga ggaggaagtg   5160

tgtgacaccc tcactattga gctgcagaag aagccgggaa aaggcctagg attaagtatt   5220

gttggtaaaa gaaacgatac tggagtattt gtgtcagaca ttgtcaaagg aggaattgca   5280

gatgccgatg gaagactgat gcagggagac cagatattaa tggtgaatgg ggaagacgtt   5340

cgtaatgcca cccaagaagc ggttgccgct ttgctaaagt gttccctagg cacagtaacc   5400

ttggaagttg gaagaatcaa agctggatcc agtacatctg agtcactgga aagtagctca   5460

aagaagaatg cattggcatc tgaaatacag ggattaagaa cagtcgaaat gaaaaagggc   5520

cctactgact cactgggaat cagcatcgct ggaggagtag gcagcccact tggtgatgtg   5580

cctatattta ttgcaatgat gcacccaact ggagttgcag cacagaccca aaaactcaga   5640

gttggggata ggattgtcac catctgtggc acatccactg agggcatgac tcacacccaa   5700

gcagttaacc tactgaaaaa tgcatctggc tccattgaaa tgcaggtggt tgctggagga   5760

gacgtgagtg tggtcacagg tcatcagcag gagcctgcaa gttccagtct ttctttcact   5820

gggctgacgt caagcagtat atttcaggat gatttaggac ctcctcaatg taagtctatt   5880

acactagagc gaggaccaga tggcttaggc ttcagtatag ttggaggata tggcagccct   5940

catggagact tacccattta tgttaaaaca gtgtttgcaa agggagcagc ctctgaagac   6000

ggacgtctga aaggggcgga tcagatcatt gctgtcaatg ggcagagtct agaaggagtc   6060

acccatgaag aagctgttgc catccttaaa cggacaaaag gcactgtcac tttgatggtt   6120

ctctcttga                                                           6129
```

<210> SEQ ID NO 20
<211> LENGTH: 2042
<212> TYPE: PRT
<213> ORGANISM: Homo sapiens

<400> SEQUENCE: 20

```
Met Leu Glu Ala Ile Asp Lys Asn Arg Ala Leu His Ala Ala Glu Arg
1               5                   10                  15

Leu Gln Thr Lys Leu Arg Glu Arg Gly Asp Val Ala Asn Glu Asp Lys
            20                  25                  30

Leu Ser Leu Leu Lys Ser Val Leu Gln Ser Pro Leu Phe Ser Gln Ile
        35                  40                  45
```

```
Leu Ser Leu Gln Thr Ser Val Gln Gln Leu Lys Asp Gln Val Asn Ile
    50                  55                  60

Ala Thr Ser Ala Thr Ser Asn Ile Glu Tyr Ala His Val Pro His Leu
65                  70                  75                  80

Ser Pro Ala Val Ile Pro Thr Leu Gln Asn Glu Ser Phe Leu Leu Ser
                85                  90                  95

Pro Asn Asn Gly Asn Leu Glu Ala Leu Thr Gly Pro Gly Ile Pro His
            100                 105                 110

Ile Asn Gly Lys Pro Ala Cys Asp Glu Phe Asp Gln Leu Ile Lys Asn
        115                 120                 125

Met Ala Gln Gly Arg His Val Glu Val Phe Glu Leu Leu Lys Pro Pro
    130                 135                 140

Ser Gly Gly Leu Gly Phe Ser Val Val Gly Leu Arg Ser Glu Asn Arg
145                 150                 155                 160

Gly Glu Leu Gly Ile Phe Val Gln Glu Ile Gln Glu Gly Ser Val Ala
                165                 170                 175

His Arg Asp Gly Arg Leu Lys Glu Thr Asp Gln Ile Leu Ala Ile Asn
            180                 185                 190

Gly Gln Ala Leu Asp Gln Thr Ile Thr His Gln Gln Ala Ile Ser Ile
        195                 200                 205

Leu Gln Lys Ala Lys Asp Thr Val Gln Leu Val Ile Ala Arg Gly Ser
    210                 215                 220

Leu Pro Gln Leu Val Ser Pro Ile Val Ser Arg Ser Pro Ser Ala Ala
225                 230                 235                 240

Ser Thr Ile Ser Ala His Ser Asn Pro Val His Trp Gln His Met Glu
                245                 250                 255

Thr Ile Glu Leu Val Asn Asp Gly Ser Gly Leu Gly Phe Gly Ile Ile
            260                 265                 270

Gly Gly Lys Ala Thr Gly Val Ile Val Lys Thr Ile Leu Pro Gly Gly
        275                 280                 285

Val Ala Asp Gln His Gly Arg Leu Cys Ser Gly Asp His Ile Leu Lys
    290                 295                 300

Ile Gly Asp Thr Asp Leu Ala Gly Met Ser Ser Glu Gln Val Ala Gln
305                 310                 315                 320

Val Leu Arg Gln Cys Gly Asn Arg Val Lys Leu Met Ile Ala Arg Gly
                325                 330                 335

Ala Ile Glu Glu Arg Thr Ala Pro Thr Ala Leu Gly Ile Thr Leu Ser
            340                 345                 350

Ser Ser Pro Thr Ser Thr Pro Glu Leu Arg Val Asp Ala Ser Thr Gln
        355                 360                 365

Lys Gly Glu Glu Ser Glu Thr Phe Asp Val Glu Leu Thr Lys Asn Val
    370                 375                 380

Gln Gly Leu Gly Ile Thr Ile Ala Gly Tyr Ile Gly Asp Lys Lys Leu
385                 390                 395                 400

Glu Pro Ser Gly Ile Phe Val Lys Ser Ile Thr Lys Ser Ser Ala Val
                405                 410                 415

Glu His Asp Gly Arg Ile Gln Ile Gly Asp Gln Ile Ile Ala Val Asp
            420                 425                 430

Gly Thr Asn Leu Gln Gly Phe Thr Asn Gln Gln Ala Val Glu Val Leu
        435                 440                 445

Arg His Thr Gly Gln Thr Val Leu Leu Thr Leu Met Arg Arg Gly Met
    450                 455                 460

Lys Gln Glu Ala Glu Leu Met Ser Arg Glu Asp Val Thr Lys Asp Ala
```

-continued

```
465                 470                 475                 480

Asp Leu Ser Pro Val Asn Ala Ser Ile Ile Lys Glu Asn Tyr Glu Lys
                485                 490                 495

Asp Glu Asp Phe Leu Ser Ser Thr Arg Asn Thr Asn Ile Leu Pro Thr
            500                 505                 510

Glu Glu Glu Gly Tyr Pro Leu Leu Ser Ala Glu Ile Glu Glu Ile Glu
        515                 520                 525

Asp Ala Gln Lys Gln Glu Ala Ala Leu Leu Thr Lys Trp Gln Arg Ile
    530                 535                 540

Met Gly Ile Asn Tyr Glu Ile Val Val Ala His Val Ser Lys Phe Ser
545                 550                 555                 560

Glu Asn Ser Gly Leu Gly Ile Ser Leu Glu Ala Thr Val Gly His His
                565                 570                 575

Phe Ile Arg Ser Val Leu Pro Glu Gly Pro Val Gly His Ser Gly Lys
            580                 585                 590

Leu Phe Ser Gly Asp Glu Leu Leu Glu Val Asn Gly Ile Thr Leu Leu
        595                 600                 605

Gly Glu Asn His Gln Asp Val Val Asn Ile Leu Lys Glu Leu Pro Ile
    610                 615                 620

Glu Val Thr Met Val Cys Cys Arg Arg Thr Val Pro Pro Thr Thr Gln
625                 630                 635                 640

Ser Glu Leu Asp Ser Leu Asp Leu Cys Asp Ile Glu Leu Thr Glu Lys
                645                 650                 655

Pro His Val Asp Leu Gly Glu Phe Ile Gly Ser Ser Glu Thr Glu Asp
            660                 665                 670

Pro Val Leu Ala Met Thr Asp Ala Gly Gln Ser Thr Glu Glu Val Gln
        675                 680                 685

Ala Pro Leu Ala Met Trp Glu Ala Gly Ile Gln His Ile Glu Leu Glu
    690                 695                 700

Lys Gly Ser Lys Gly Leu Gly Phe Ser Ile Leu Asp Tyr Gln Asp Pro
705                 710                 715                 720

Ile Asp Pro Ala Ser Thr Val Ile Ile Ile Arg Ser Leu Val Pro Gly
                725                 730                 735

Gly Ile Ala Glu Lys Asp Gly Arg Leu Leu Pro Gly Asp Arg Leu Met
            740                 745                 750

Phe Val Asn Asp Val Asn Leu Glu Asn Ser Ser Leu Glu Glu Ala Val
        755                 760                 765

Glu Ala Leu Lys Gly Ala Pro Ser Gly Thr Val Arg Ile Gly Val Ala
    770                 775                 780

Lys Pro Leu Pro Leu Ser Pro Glu Glu Gly Tyr Val Ser Ala Lys Glu
785                 790                 795                 800

Asp Ser Phe Leu Tyr Pro Pro His Ser Cys Glu Glu Ala Gly Leu Ala
                805                 810                 815

Asp Lys Pro Leu Phe Arg Ala Asp Leu Ala Leu Val Gly Thr Asn Asp
            820                 825                 830

Ala Asp Leu Val Asp Glu Ser Thr Phe Glu Ser Pro Tyr Ser Pro Glu
        835                 840                 845

Asn Asp Ser Ile Tyr Ser Thr Gln Ala Ser Ile Leu Ser Leu His Gly
    850                 855                 860

Ser Ser Cys Gly Asp Gly Leu Asn Tyr Gly Ser Ser Leu Pro Ser Ser
865                 870                 875                 880

Pro Pro Lys Asp Val Ile Glu Asn Ser Cys Asp Pro Val Leu Asp Leu
                885                 890                 895
```

```
His Met Ser Leu Glu Glu Leu Tyr Thr Gln Asn Leu Leu Gln Arg Gln
            900                 905                 910

Asp Glu Asn Thr Pro Ser Val Asp Ile Ser Met Gly Pro Ala Ser Gly
        915                 920                 925

Phe Thr Ile Asn Asp Tyr Thr Pro Ala Asn Ala Ile Glu Gln Gln Tyr
    930                 935                 940

Glu Cys Glu Asn Thr Ile Val Trp Thr Glu Ser His Leu Pro Ser Glu
945                 950                 955                 960

Val Ile Ser Ser Ala Glu Leu Pro Ser Val Leu Pro Asp Ser Ala Gly
                965                 970                 975

Lys Gly Ser Glu Tyr Leu Leu Glu Gln Ser Ser Leu Ala Cys Asn Ala
            980                 985                 990

Glu Cys Val Met Leu Gln Asn Val  Ser Lys Glu Ser Phe  Glu Arg Thr
        995                 1000                 1005

Ile Asn  Ile Ala Lys Gly Asn  Ser Ser Leu Gly Met  Thr Val Ser
    1010                 1015                 1020

Ala Asn  Lys Asp Gly Leu Gly  Met Ile Val Arg Ser  Ile Ile His
    1025                 1030                 1035

Gly Gly  Ala Ile Ser Arg Asp  Gly Arg Ile Ala Ile  Gly Asp Cys
    1040                 1045                 1050

Ile Leu  Ser Ile Asn Glu Glu  Ser Thr Ile Ser Val  Thr Asn Ala
    1055                 1060                 1065

Gln Ala  Arg Ala Met Leu Arg  Arg His Ser Leu Ile  Gly Pro Asp
    1070                 1075                 1080

Ile Lys  Ile Thr Tyr Val Pro  Ala Glu His Leu Glu  Glu Phe Lys
    1085                 1090                 1095

Ile Ser  Leu Gly Gln Gln Ser  Gly Arg Val Met Ala  Leu Asp Ile
    1100                 1105                 1110

Phe Ser  Ser Tyr Thr Gly Arg  Asp Ile Pro Glu Leu  Pro Glu Arg
    1115                 1120                 1125

Glu Glu  Gly Glu Gly Glu Glu  Ser Glu Leu Gln Asn  Thr Ala Tyr
    1130                 1135                 1140

Ser Asn  Trp Asn Gln Pro Arg  Arg Val Glu Leu Trp  Arg Glu Pro
    1145                 1150                 1155

Ser Lys  Ser Leu Gly Ile Ser  Ile Val Gly Gly Arg  Gly Met Gly
    1160                 1165                 1170

Ser Arg  Leu Ser Asn Gly Glu  Val Met Arg Gly Ile  Phe Ile Lys
    1175                 1180                 1185

His Val  Leu Glu Asp Ser Pro  Ala Gly Lys Asn Gly  Thr Leu Lys
    1190                 1195                 1200

Pro Gly  Asp Arg Ile Val Glu  Val Asp Gly Met Asp  Leu Arg Asp
    1205                 1210                 1215

Ala Ser  His Glu Gln Ala Val  Glu Ala Ile Arg Lys  Ala Gly Asn
    1220                 1225                 1230

Pro Val  Val Phe Met Val Gln  Ser Ile Ile Asn Arg  Pro Arg Lys
    1235                 1240                 1245

Ser Pro  Leu Pro Ser Leu Leu  His Asn Leu Tyr Pro  Lys Tyr Asn
    1250                 1255                 1260

Phe Ser  Ser Thr Asn Pro Phe  Ala Asp Ser Leu Gln  Ile Asn Ala
    1265                 1270                 1275

Asp Lys  Ala Pro Ser Gln Ser  Glu Ser Glu Pro Glu  Lys Ala Pro
    1280                 1285                 1290
```

```
Leu Cys  Ser Val Pro Pro Pro  Pro Pro Ser Ala Phe  Ala Glu Met
    1295                 1300                 1305

Gly Ser  Asp His Thr Gln Ser  Ser Ala Ser Lys Ile  Ser Gln Asp
    1310                 1315                 1320

Val Asp  Lys Glu Asp Glu Phe  Gly Tyr Ser Trp Lys  Asn Ile Arg
    1325                 1330                 1335

Glu Arg  Tyr Gly Thr Leu Thr  Gly Glu Leu His Met  Ile Glu Leu
    1340                 1345                 1350

Glu Lys  Gly His Ser Gly Leu  Gly Leu Ser Leu Ala  Gly Asn Lys
    1355                 1360                 1365

Asp Arg  Ser Arg Met Ser Val  Phe Ile Val Gly Ile  Asp Pro Asn
    1370                 1375                 1380

Gly Ala  Ala Gly Lys Asp Gly  Arg Leu Gln Ile Ala  Asp Glu Leu
    1385                 1390                 1395

Leu Glu  Ile Asn Gly Gln Ile  Leu Tyr Gly Arg Ser  His Gln Asn
    1400                 1405                 1410

Ala Ser  Ser Ile Ile Lys Cys  Ala Pro Ser Lys Val  Lys Ile Ile
    1415                 1420                 1425

Phe Ile  Arg Asn Lys Asp Ala  Val Asn Gln Met Ala  Val Cys Pro
    1430                 1435                 1440

Gly Asn  Ala Val Glu Pro Leu  Pro Ser Asn Ser Glu  Asn Leu Gln
    1445                 1450                 1455

Asn Lys  Glu Thr Glu Pro Thr  Val Thr Thr Ser Asp  Ala Ala Val
    1460                 1465                 1470

Asp Leu  Ser Ser Phe Lys Asn  Val Gln His Leu Glu  Leu Pro Lys
    1475                 1480                 1485

Asp Gln  Gly Gly Leu Gly Ile  Ala Ile Ser Glu Glu  Asp Thr Leu
    1490                 1495                 1500

Ser Gly  Val Ile Ile Lys Ser  Leu Thr Glu His Gly  Val Ala Ala
    1505                 1510                 1515

Thr Asp  Gly Arg Leu Lys Val  Gly Asp Gln Ile Leu  Ala Val Asp
    1520                 1525                 1530

Asp Glu  Ile Val Val Gly Tyr  Pro Ile Glu Lys Phe  Ile Ser Leu
    1535                 1540                 1545

Leu Lys  Thr Ala Lys Met Thr  Val Lys Leu Thr Ile  His Ala Glu
    1550                 1555                 1560

Asn Pro  Asp Ser Gln Ala Val  Pro Ser Ala Ala Gly  Ala Ala Ser
    1565                 1570                 1575

Gly Glu  Lys Lys Asn Ser Ser  Gln Ser Leu Met Val  Pro Gln Ser
    1580                 1585                 1590

Gly Ser  Pro Glu Pro Glu Ser  Ile Arg Asn Thr Ser  Arg Ser Ser
    1595                 1600                 1605

Thr Pro  Ala Ile Phe Ala Ser  Asp Pro Ala Thr Cys  Pro Ile Ile
    1610                 1615                 1620

Pro Gly  Cys Glu Thr Thr Ile  Glu Ile Ser Lys Gly  Arg Thr Gly
    1625                 1630                 1635

Leu Gly  Leu Ser Ile Val Gly  Gly Ser Asp Thr Leu  Leu Gly Ala
    1640                 1645                 1650

Ile Ile  Ile His Glu Val Tyr  Glu Glu Gly Ala Ala  Cys Lys Asp
    1655                 1660                 1665

Gly Arg  Leu Trp Ala Gly Asp  Gln Ile Leu Glu Val  Asn Gly Ile
    1670                 1675                 1680

Asp Leu  Arg Lys Ala Thr His  Asp Glu Ala Ile Asn  Val Leu Arg
```

```
    1685                1690                1695

Gln Thr  Pro Gln Arg Val Arg  Leu Thr Leu Tyr Arg  Asp Glu Ala
    1700                1705                1710

Pro Tyr  Lys Glu Glu Glu Val  Cys Asp Thr Leu Thr  Ile Glu Leu
    1715                1720                1725

Gln Lys  Lys Pro Gly Lys Gly  Leu Gly Leu Ser Ile  Val Gly Lys
    1730                1735                1740

Arg Asn  Asp Thr Gly Val Phe  Val Ser Asp Ile Val  Lys Gly Gly
    1745                1750                1755

Ile Ala  Asp Ala Asp Gly Arg  Leu Met Gln Gly Asp  Gln Ile Leu
    1760                1765                1770

Met Val  Asn Gly Glu Asp Val  Arg Asn Ala Thr Gln  Glu Ala Val
    1775                1780                1785

Ala Ala  Leu Leu Lys Cys Ser  Leu Gly Thr Val Thr  Leu Glu Val
    1790                1795                1800

Gly Arg  Ile Lys Ala Gly Ser  Ser Thr Ser Glu Ser  Leu Glu Ser
    1805                1810                1815

Ser Ser  Lys Lys Asn Ala Leu  Ala Ser Glu Ile Gln  Gly Leu Arg
    1820                1825                1830

Thr Val  Glu Met Lys Lys Gly  Pro Thr Asp Ser Leu  Gly Ile Ser
    1835                1840                1845

Ile Ala  Gly Gly Val Gly Ser  Pro Leu Gly Asp Val  Pro Ile Phe
    1850                1855                1860

Ile Ala  Met Met His Pro Thr  Gly Val Ala Ala Gln  Thr Gln Lys
    1865                1870                1875

Leu Arg  Val Gly Asp Arg Ile  Val Thr Ile Cys Gly  Thr Ser Thr
    1880                1885                1890

Glu Gly  Met Thr His Thr Gln  Ala Val Asn Leu Leu  Lys Asn Ala
    1895                1900                1905

Ser Gly  Ser Ile Glu Met Gln  Val Val Ala Gly Gly  Asp Val Ser
    1910                1915                1920

Val Val  Thr Gly His Gln Gln  Glu Pro Ala Ser Ser  Ser Leu Ser
    1925                1930                1935

Phe Thr  Gly Leu Thr Ser Ser  Ser Ile Phe Gln Asp  Asp Leu Gly
    1940                1945                1950

Pro Pro  Gln Cys Lys Ser Ile  Thr Leu Glu Arg Gly  Pro Asp Gly
    1955                1960                1965

Leu Gly  Phe Ser Ile Val Gly  Gly Tyr Gly Ser Pro  His Gly Asp
    1970                1975                1980

Leu Pro  Ile Tyr Val Lys Thr  Val Phe Ala Lys Gly  Ala Ala Ser
    1985                1990                1995

Glu Asp  Gly Arg Leu Lys Arg  Gly Asp Gln Ile Ile  Ala Val Asn
    2000                2005                2010

Gly Gln  Ser Leu Glu Gly Val  Thr His Glu Glu Ala  Val Ala Ile
    2015                2020                2025

Leu Lys  Arg Thr Lys Gly Thr  Val Thr Leu Met Val  Leu Ser
    2030                2035                2040


<210> SEQ ID NO 21
<211> LENGTH: 7
<212> TYPE: PRT
<213> ORGANISM: Homo sapiens

<400> SEQUENCE: 21
```

-continued

```
Pro Lys Lys Lys Arg Lys Val
1               5


<210> SEQ ID NO 22
<211> LENGTH: 16
<212> TYPE: PRT
<213> ORGANISM: HOmo sapiens

<400> SEQUENCE: 22

Lys Arg Pro Ala Ala Thr Lys Lys Ala Gly Gln Ala Lys Lys Lys Lys
1               5                   10                  15
```

METHOD FOR TREATING HEART DISEASE BY INHIBITING THE COXSACKIEVIRUS-ADENOVIRUS RECEPTOR

CROSS-REFERENCE TO RELATED APPLICATIONS

This application claims priority to International Patent Application No. PCT/EP2013/066426 filed Aug. 5, 2013, which claims priority to European Application No. 13 164 109.4 filed Apr. 17, 2013 and European Patent Application No. 12 179 295.6 filed Aug. 3, 2012, the disclosures of which are each incorporated by reference herein in their entireties.

FIELD OF INVENTION

The invention pertains to means for downregulating or inhibiting the Coxsackievirus-Adenovirus Receptor (CAR) in the heart, in particular in a cardiac cell for treating and/or curing a patient who has suffered or is predisposed to suffering a myocardial infarction (MI).

REFERENCE TO SEQUENCE LISTING

The present application is being filed along with a Sequence Listing in ASCII electronic format via EFS-web. The Sequence listing file, entitled 5535-22_SEQ_ASCII.txt, was created on Feb. 3, 2015 and is 110,592 bytes in size. The Sequence Listing is incorporated herein by reference in its entirety.

BACKGROUND

Heart diseases are the main cause of death in the developed countries and a major cause of disability. Common treatments of heart failure patients have proven benefit, but mortality and morbidity remain substantial.

Myocardial infarction (MI) can cause contractile dysfunction, which often persists even after blood flow has been restored. MI is associated with loss of cardiac contractility, altered $Ca^+$ handling and myofilament protein phosphorylation that least to increased myofibrillar calcium sensitivity and lower cross-bridge cycling rates.

Myocardial infarction can cause reversible or irreversible damage to the myocardial tissues. Damage initially includes a necrotic core surrounded by a border zone that will either recover or become irreversibly damaged, thus failing to generate tension during systole.

Myocardial infarction encompasses conditions that are caused by a sudden inadequate perfusion of the heart. This can occur through decrease of blood flow or increased demand to the heart. Symptoms can vary from crushing chest pain that radiates down the left art to nondescript jaw or back sensations.

It was an object of the invention to provide a means for preventing or treating and/or curing a patient who has suffered or is predisposed to suffering a myocardial infarction.

BRIEF DESCRIPTION OF THE DRAWINGS

Exemplary embodiments of the present invention will be described below in more detail, with reference to the accompanying drawings, of which:

FIG. 3A shows a histogram of the effects on heart weight for the sham group and the MI group; FIG. 3B shows a histogram of ejection fraction for the sham group and the MI group; and FIG. 3C shows a histogram of left ventricular inner diameter for the sham group and the MI group.

FIG. 4A shows a schematic of the CXADR gene encoding CAR with boxes representing exons 1 to 8 and the black line indicating the introns; and FIG. 4B shows that RT PCR on mRNA from C2C12 cells treated with CAR Exon6 specific morpholino results in the appearance of a lower band that indicates the isoform lacking Exon 6.

FIG. 5A shows plasmid pFastBacDual with the Coxsackievirus B3 (CVB3) structural proteins VP4, 2, 3, 1 and the proteases 2a and 3c; FIG. 5B shows plasmid pFastBacDual with GFP, the CVB3 structural proteins VP4, 2, 3, 1 and the proteases 2a and 3c; FIG. 5C shows transfection of Sf21 cells with the recombinant GFP bacmid and validation of GFP expression; FIG. 5D shows purification of Coxsackievirus-like particles (CxVLPs) in a continuous sucrose gradient; FIG. 5E shows electron microscopy of Coxsackievirus-like particles; and FIG. 5F shows uptake of GPF tagged Coxsackievirus-like particles in endothelial rBCEC4 cells.

DETAILED DESCRIPTION OF THE EXEMPLARY EMBODIMENTS

Figure 1A:
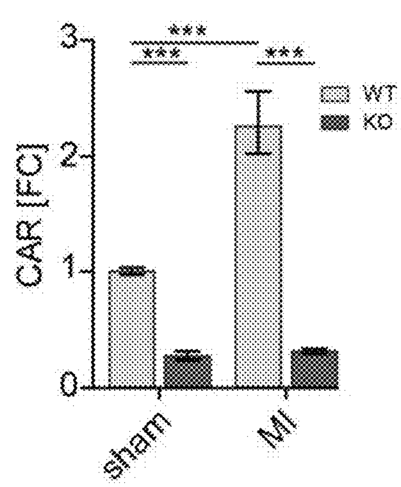
FIG. 1A shows a histogram of Coxsackievirus-Adenovirus Receptor (CAR) in myocardial infarction (MI) response of knockout (KO) animals and wildtype (WT) animals.

Exemplary embodiments of the invention will now be discussed in further detail. This invention may, however, be embodied in many different forms and should not be construed as limited to the embodiments set forth herein.

It should be understood that this invention is not limited to the particular methodology, protocols, and reagents, etc., described herein and as such may vary. The terminology used herein is for the purpose of describing particular embodiments only, and is not intended to limit the scope of the present invention.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Treatment or treating, as used herein, refers to limiting tissue damage, ameliorating or lessening symptoms, enhancing the effect of other modalities of treating tissue toxicity, preventing tissue damage or preventing permanent tissue damage, or otherwise affecting or controlling a clinical indication in a positive fashion. The term "treating" refers to therapeutic treatment and prophylactic or preventative measures.

The invention provides a way of treating the pathology associated with myocardial infarction (MI), in particular in vivo in a patient. The invention is based on the unexpected finding that the presence of the protein "Coxsackie- and Adenovirus Receptor" (CAR) in cardiomyocytes is associated with a worse outcome after myocardial infarction (MI). The decrease of CAR in cardiac cells greatly improves the prospects of patients with myocardial infarction.

Accordingly, the invention refers to the use of means that allow for a downregulation or inhibition (functional blockage) of CAR in the heart, in particular in a cardiac cell, for treating or possibly curing a patient who has suffered or is predisposed to suffering a myocardial infarction.

The term "myocardial infarction (MI)" refers to cardiac disease with evidence of myocardial necrosis in a clinical setting consistent with myocardial ischemia or elevated troponin levels in the blood (Thygesen et al., Eur Heart J. 2007 28(20): 2525-38). MI does not include a myocarditis. In a preferred embodiment, it does not include a myocarditis of viral origin.

The term "decrease of CAR" refers to the reduction of CAR activity. The term also refers to blocking CAR function through CAR-binding molecules, interfering with localization or expression of functional CAR protein, the reduction of the number of molecules encoding for a functional CAR protein, such as DNA or RNA molecules (like genomic DNA or mRNA) in a cell, in particular in a cardiac cell.

The term "downregulation" refers to a decrease or suppression of the transcription of the gene encoding for CAR reducing the expression of the CAR protein in cardiac cells. The term "downregulation" also refers to the reduction of the number of CAR molecules at the cell surface.

The term "mislocalizing" refers to CAR proteins that do not reach their final destination at the cell surface of cardiac cells or that are oriented on the cell surface differently than wildtype CAR proteins, thereby impeding their normal function.

The Coxsackie- and Adenovirus Receptor (CAR) is an important mediator in different diseases of the heart. In its role as a viral receptor, CAR mediates Coxsackievirus dependent myocarditis and in its physiological role as a cell-contact protein, CAR is important for cardiac development and remodeling.

CAR was initially identified as the receptor for Coxsackie- and Adenoviruses (He, Y. et al. Interaction of coxsackievirus B3 with the full-length coxsackievirus-adenovirus receptor. *Nat. Struct. Biol* 8, 874-878 (2001); Bewley, M. C., Springer, K., Zhang, Y. B., Freimuth, P. & Flanagan, J. M. Structural analysis of the mechanism of adenovirus binding to its human cellular receptor, CAR. *Science* 286, 1579-1583 (1999)). It is a type I transmembrane protein with two extracellular IG-domains that mediate cell adhesion to the extracellular matrix and adjacent cells as well as virus uptake. The cytoplasmic tail contains a motif that interacts with PDZ-domain proteins, which link to signal transduction and endocytosis. CAR is predominantly expressed in the developing heart and brain. It is re-induced upon cardiac remodeling such as in human dilated cardiomyopathy (Noutsias, M. et al. Human coxsackie-adenovirus receptor is colocalized with integrins alpha(v)beta(3) and alpha(v)beta (5) on the cardiomyocyte sarcolemma and upregulated in dilated cardiomyopathy: implications for cardiotropic viral infections. *Circulation* 104, 275-280 (2001)) and after myocardial infarction in the rat (Fechner, H. et al. Induction of coxsackievirus-adenovirus-receptor expression during myocardial tissue formation and remodeling: identification of a cell-to-cell contact-dependent regulatory mechanism. *Circulation* 107, 876-882 (2003)).

The CAR sequence is highly conserved between humans, mice, dogs, pigs, cattle and fish (Bergelson et al., (1997). Isolation of a common receptor for Coxsackie B viruses and adenoviruses 2 and 5. Science 275, 1320-1323; Tomko et al., 1997, HCAR and MCAR: the human and mouse cellular receptors for subgroup C adenoviruses and group B coxsackieviruses. Proc Natl Acad Sci USA 94, 3352-3356; Bergelson et al., 1998, The murine CAR homolog is a receptor for coxsackie B viruses and adenoviruses. J Virol 72, 415-419; Fechner et al., 1999, Expression of coxsackie adenovirus receptor and alphav-integrin does not correlate with adenovector targeting in vivo indicating anatomical vector barriers. Gene Ther 6, 1520-1535; Fechner et al., 1999, Expression of coxsackie adenovirus receptor and alphav-integrin does not correlate with adenovector targeting in vivo indicating anatomical vector barriers. Gene Ther 6, 1520-1535; Thoelen et al., 2001, Characterization of a cDNA encoding the bovine coxsackie and adenovirus receptor. Biochem. Biophys. Res. Commun 288, 805-808; Petrella et al., 2002, A zebrafish coxsackievirus and adenovirus receptor homologue interacts with coxsackie B virus and adenovirus. J Virol 76, 10503-10506).

SEQ ID NO 1 shows the mRNA sequence of human CAR, SEQ ID NO 2 shows the protein sequence of human CAR. The genomic sequence of CAR is also known and can be retrieved from appropriate databases.

In one aspect, the invention refers to a means for downregulating, inhibiting and/or mislocalizing CAR in a cardiac cell for treating or curing a patient who has suffered or is predisposed to suffering a myocardial infarction.

In order to achieve downregulation, inhibition or mislocalization of CAR, several approaches can be taken, such as at least one or more of the following:

1. One approach is the functional inhibition of the CAR protein, which can be achieved via the extracellular and/or via the intracellular part of CAR. The functional inhibition via the extracellular part of CAR is preferred.

For example, inhibition of the CAR protein can be achieved using an antibody (or a specifically binding fragment thereof) capable of binding specifically to the CAR protein, or using a CAR-Fc-fusion protein, or any other CAR ligand (or a specifically binding fragment thereof) such as a Coxsackievirus or Coxsackievirus-like particle or fragment thereof, an adenovirus, or andenovirus-like particle or fragment thereof (e.g. the adenovirus fiber protein) or an extracellular matrix protein or a cytoplasmatic CAR binding protein such as ZO-1 or Mupp1 (reviewed in Fischer et al., J Mol Med 87(9): 879-8 (2009)). Binding can also be blocked by a small molecule that acts as a ligand replacing the function of Adenovirus Fiber, CAR-Fc or the Coxsackievirus-like particle.

A virus-like particle is a structure that contains virus surface proteins alone or in combination with other viral and/or non-viral molecules. The Coxsackievirus-like particle is in one embodiment generated by the expression of the precursor protein of the Coxsackievirus that contains all surface proteins (VP1-4) and the virus protease (3C) that cleaves the precursor into functional proteins. Expression in an insect cell system, which leads to properly processed surface-proteins that self-assemble is preferred and is described, e.g., in the methods section below.

CAR-Fc is, in one embodiment, generated by fusion of the extracellular domain of human CAR with the carboxy terminus of the human IgG1 Fc coding region. Subsequently, CAR-Fc coding sequence is inserted into a vector, e.g. an adenoviral shuttle plasmid that may contain improved elements of the Tet-On gene expression system in different configurations (Pinkert et al., Circulation 2009; 120; 2358-2366). An example for a CAR-Fc sequence is provided as SEQ ID NO 3 (cDNA) and 4 (protein).

A suitable antibody is, e.g., for example, the mouse-anti-human CAR antibody RcmB1 (He, Y. et al. Interaction of coxsackievirus B3 with the full length coxsackievirus-adenovirus receptor. Nat. Struct. Biol 8, 874-878 (2001)). A suitable fiber protein is described in Wang et al., J Virol. 2011; 85(13): 6390-402.

Means for downregulating or inhibiting CAR in the heart are, e.g., antibodies, such as anti-CAR antibodies. Antibodies, as used herein means refers to immunoglobulin molecules as well as portions, fragments, peptides and derivatives thereof such as, for example, Fab, Fab', F(ab')2, Fv, CDR regions, paratopes, or any portion or peptide sequence of an antibody that is capable of binding an antigen or epitope, and includes polyclonal antibodies, monoclonal antibodies, chimeric antibodies, fully humanized antibodies, recombinant antibodies, and monoclonal antibodies produced by transgenic animals or portions fragments, peptides and derivatives thereof. An antibody is said to be "capable of binding" a molecule if it is capable of specifically reacting with the molecule to thereby bind the molecule to the antibody. Numerous antibodies have been approved for use in humans. See, e.g., Walden, 9 Nat. Med. 269 (2004).

2. Another approach is the removal or alteration of the genomic sequence encoding the CAR protein, such that CAR is not functionally expressed, e.g. through homologous recombination.

This can be done, for example, using the Cre/Lox system that is known in the art (Lisewski et al., J Ex Med 2008, 205(10): 2369-2379). In a preferred embodiment, a polynucleotide encoding CAR or a fragment thereof such as CAR exon 1, which contains the start-codon ATG, is introduced into the genome of cardiac cells of a subject to inhibit the transcription of the genomic DNA encoding for CAR fully or at least partially. This results in a loss of protein expression and/or in the loss of CAR function at the cell surface of cardiac cells.

3. Another approach is the inhibition of CAR synthesis from an mRNA that encodes the CAR protein. For this purpose, RNA or siRNA or their chemical derivatives can be used, such as antisense RNA or morpholinos (PMOs, phosphorodiamidate morpholino oligo). In a preferred embodiment, a morpholino is used that targets expression of the protein (see, e.g. Raschperger et al., Dev Biol. 2008; 313(1): 455-64).

4. Another approach is the inhibition of CAR function by interfering with alternative splicing of CAR. Targeting any CAR exon leads to a truncated protein. Preferred is the interference with the exon encoding the transmembrane region, where loss results in expression of a soluble CAR isoform (see, e.g. Dörner et al., J Biol Chem. 2004; 279(18): 18497-503).

In one embodiment, a morpholino is used in the invention that is targeted at the 5' region of Exon 6 of CAR (compare FIG. 4). The CAR-E6 morpholino sequence is 5'-GTCTAGTTTCACTGAATTACCTGAT-3' (SEQ ID NO. 7).

5. Another approach is the inhibition of CAR function by mislocalizing CAR within the cell, preferably by using inhibitor molecules or chemical substances that interrupt or suppress the intracellular transport of CAR. Mislocalization can, for example, be achieved by adding a localization signal to the CAR coding sequence (such as a nuclear localization signal, e.g. PKKKRKV (SEQ ID NO. 21) or KR[PAATKKAGQA]KKKK (SEQ ID NO. 22) that targets the protein to a part of the cell where it usually does not appear or by removing the secretion signal, which prevents synthesis into the ER.

6. Yet another approach is the inhibition of the function of the CAR protein using a small molecule or chemical compound. Small molecules can, for example, be used to interfere with splicing of the CAR mRNA transcript or with binding of CAR.

As mentioned above, binding of CAR can be blocked by a small molecule that acts as a ligand replacing the function of Adenovirus Fiber, CAR-Fc or the Coxsackievirus-like particle.

In another aspect, the invention refers to a method (in vitro or in vivo) for downregulating, inhibiting or mislocalizing CAR in a cardiac cell, in particular for treating or curing a patient who has suffered a myocardial infarction (MI). Any approach for targeting CAR as described above and herein can be used for this purpose.

In another aspect, the invention refers to the use of

- A polynucleotide encoding an antibody specifically binding to CAR or encoding a truncated or mutated form of CAR or CAR-Fc, a CAR ligand (e.g., a Coxsackie-like particle, Adenovirus-fiber, ZO-1 and/or Mupp1) or a functional fragment thereof, as described herein, and/or
- A truncated or mutated form of CAR or CAR-Fc polypeptide or a functional fragment thereof, as described herein, and/or
- A heterologous CAR binding protein or fragment thereof, as described herein.

In one embodiment, the substances given above are used for treating MI.

The invention also refers to the use (in vitro or in vivo) of a vector comprising a polynucleotide encoding an antibody specifically binding to CAR or encoding a truncated or mutated form of CAR or a CAR fusion protein (as described herein), and their use in treating MI. In another aspect, the invention refers to a vector encoding for a CAR ligand (e.g., a Coxsackievirus-like particle, Adenovirus-fiber, ZO-1 and/or Mupp1) or a functional fragment thereof.

In another embodiment of the invention, an antibody specifically binding to CAR, a CAR-Fc polypeptide, and/or CAR ligand (e.g., a Coxsackievirus-like particle, Adenovirus fiber, ZO-1 and/or Mupp1) or a functional fragment thereof is introduced into a human subject in need thereof (patient). The introduced antibody, CAR-Fc polypeptide, CAR ligand or a functional fragment thereof inhibits the CAR mediated cell-to-cell interaction and is therefore suitable for treating or curing a patient who has suffered a myocardial infarction or for the prevention of myocardial infarction in a patient who is susceptible to myocardial infarction.

Dosage levels preferably lie in the range of 0.001 to 100 mg/kg body weight, more preferably in the range of 0.1 to 50 mg/kg body weight of the patient to be treated. Appropriate dosage levels may be determined by any suitable method known to one skilled in the art. It will be understood, however, that the specific dose level for any particular patient will depend upon a variety of factors including the activity of the specific compound employed, the age, body weight, general health, sex, diet, time of administration, route of administration, rate of excretion, drug combination and the severity of the condition to be treated.

In another aspect, the invention also relates to a method for downregulating or functionally inhibiting the CAR protein that is expressed at the cell surface using inhibitory molecules. Such a method comprises, in one embodiment, the following:

First, an effective amount of the inhibitory molecule is administered to a subject in need thereof. The administration is preferably done into a blood vessel of the subject, but other routes of administration may also be appropriate.

The inhibitory molecule subsequently binds to the CAR protein. This binding may break up cell-to-cell interactions and may prevent the formation of new cell-to-cell interactions. Thereby, CAR mediated cell-to-cell interactions are impeded and/or prevented.

In a further aspect, the invention refers to a method (in vitro or in vivo) for mislocalizing CAR protein (i.e., preferably, making the protein intracellular) using chemical compounds or molecules that interrupt the intracellular transport of the CAR protein, preferably comprising the steps of incubating living cardiac cells with said chemical compounds or molecules and interrupting the intracellular CAR protein transport (e.g. protein folding, chaperone binding or intracellular membrane transport). An example for such a molecule is CAR Exon6 morpholino (CAR-E6) (see FIG. 4 and the description thereof).

In another aspect, the invention refers to a pharmaceutical composition comprising a means for downregulating or inhibiting or mislocalizing CAR in the heart, in particular in a cardiac cell, as described above and herein, in particular for treating or curing a patient who has suffered a myocardial infarction (MI). The pharmaceutical composition of the invention may additionally comprise a pharmaceutically acceptable carrier, diluent, and/or adjuvant.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Powders can contain, in addition to a compound of this invention, excipients such as lactose, talc, silicic acid, aluminum hydroxide, calcium silicates and polyimide powder, or mixtures of these substances.

These pharmaceutical compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

The present invention therefore includes, pharmaceutical formulations comprising the nucleic acids described herein, including pharmaceutically acceptable salts thereof, in pharmaceutically acceptable carriers for aerosol, oral and parenteral administration. Also, the present invention includes such compounds, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the present invention, a nucleic acid described herein, and pharmaceutically acceptable salts thereof, may be administered orally or through inhalation as a solid, or may be administered intramuscularly or intravenously as a solution, suspension or emulsion. Alternatively, the compounds or salts may also be administered by inhalation, intravenously or intramuscularly as a liposomal suspension.

Pharmaceutical formulations are also provided which are suitable for administration as an aerosol, by inhalation. These formulations comprise a solution or suspension of the desired nucleic acid herein, or a salt thereof, or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 μm. The solid particles can be obtained by processing the solid compound of any nucleic acid described herein, or a salt thereof, in any appropriate manner known in the, art, such as by micronization. Most preferably, the size of the solid particles or droplets will be from about 1 μm to about 2 μm. In this respect, commercial nebulizers are available to achieve this purpose.

Preferably, when the pharmaceutical formulation suitable for administration as an aerosol is in the form of a liquid, the formulation will comprise a water-soluble compound of any nucleic acid described herein, or a salt thereof, in a carrier that comprises water. A surfactant may be present that lowers the surface tension of the formulation sufficiently to result in the formation of droplets within the desired size range when subjected to nebulization.

Per-oral compositions also include liquid solutions, emulsions, suspensions, and the like. The pharmaceutically acceptable carriers suitable for preparation of such compositions are well known in the art. Typical components of carriers for syrups, elixirs, emulsions, and suspensions include ethanol, glycerol, propylene glycol, polyethylene glycol, liquid sucrose, sorbitol, and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Other compositions useful for attaining systemic delivery of the nucleic acids include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Means of oral delivery of short interfering RNAs have been described, e.g., in Aouadi et al., Nature 458, 1180-1184, 2009.

The invention also refers to a method for treating a subject suffering from MI, comprising decreasing the concentration of the CAR mRNA or of the CAR protein and mislocalizing CAR in a cardiac cell. The means to achieve this are the same as described above and herein. Specifically, the invention refers to a method for treating a subject suffering from MI, comprising decreasing the concentration of the CAR mRNA of SEQ ID NO 1 or of the CAR protein of SEQ ID NO 2 in a cardiac cell or comprising a CAR ligand, such as an antibody or a fragment thereof specifically binding to CAR or a CAR ligand, such as a Coxsackievirus-like particle or a fragment thereof, e.g., as described in the examples.

In a further aspect, the invention refers to the use of CAR (either as a CAR protein or parts thereof, or as a nucleic acid encoding for the CAR protein or parts thereof) as a target for treating or curing a patient who has suffered or is predisposed to suffering a myocardial infarction or for preventing myocardial infarction.

The invention is presented here with reference to human and mouse sequences. A person of skill in the art will be able to transfer the invention to other species based on the information known in the art and the information given herein.

To investigate the role of CAR in differentiation and remodeling of the heart, CAR KO animals (Lisewski, U. et al. The tight junction protein CAR regulates cardiac conduction and cell-cell communication. *J Exp Med* 205, 2369-79 (2008)) were generated. After myocardial infarction, CAR is upregulated in the wildtype heart. Survival after myocardial infarction is greatly improved in the CAR deficient mouse (FIG. 1). The survival is associated with improved remodeling as knockout hearts are not as enlarged, the fibrotic area is more contained and wall-thickness at the site of infarction is increased (FIG. 2). This is expected to result in fewer ruptures of the ventricular wall post infarction.

In CAR deficient animals, not only improved morphology is seen, but also improved function. The ejection fraction (EF), which reflects contractile function, is not depressed as much in the knockout heart after infarction and a pronounced compensatory hypertrophy is not seen (FIG. 3).

Using coronary artery ligation, the inventors found a negative effect of CAR in myocardial infarction and subsequent remodeling. The negative effects on heart weight and -function are significantly smaller in CAR KO animals. In a cell transplantation following myocardial infarction, CAR KO cells perform better, possibly due to differences in migration and adhesion.

Figure 1B:
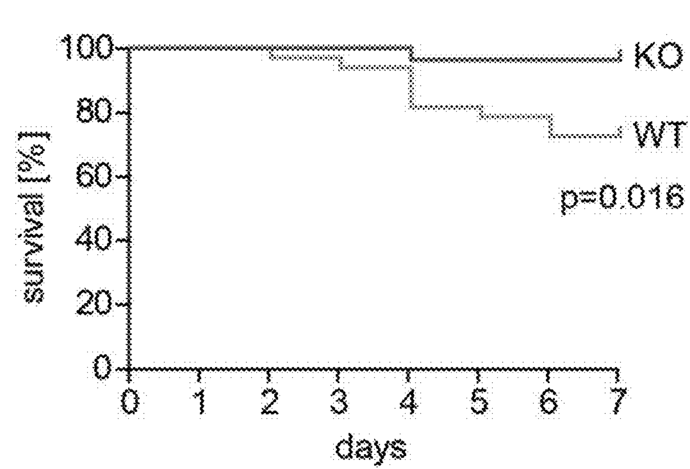
FIG. 1B shows a graph of survival in percentage vs. days for KO animals and WT animals after MI.

FIGS. 1A and 1B show that CAR is important in MI response. CAR is upregulated in the heart after myocardial infarction (MI) as compared to the control (sham) only in wildtype animals (light grey) and not in CAR deficient animals (dark grey), as shown in FIG. 1A. Survival of CAR KO animals after myocardial infarction was improved significantly, as shown in FIG. 1B.

Figure 2A:
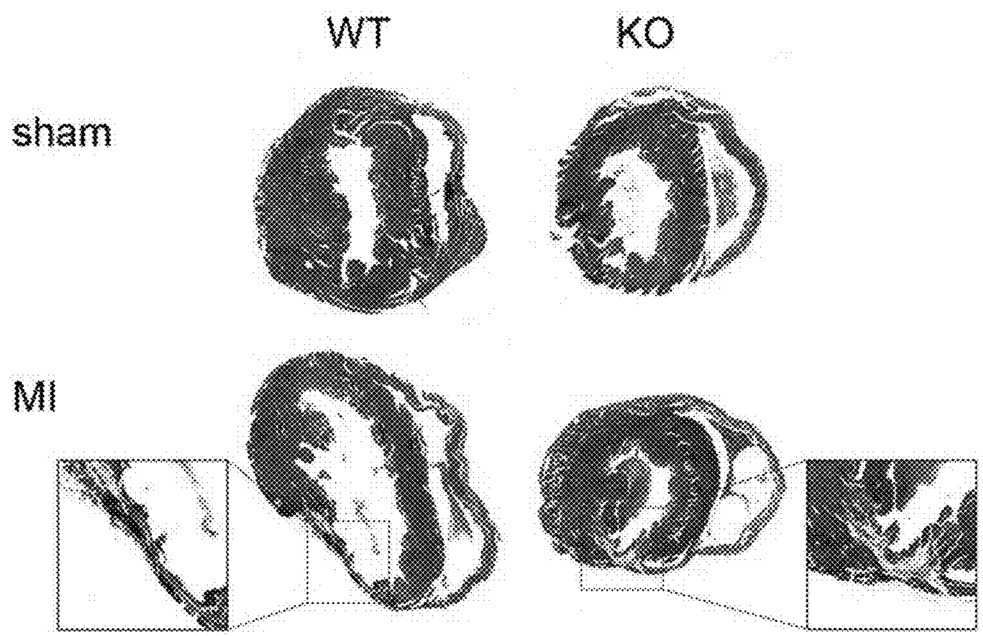
FIG. 2A shows histology of hearts 30 days after an infarction.
Figure 2B:
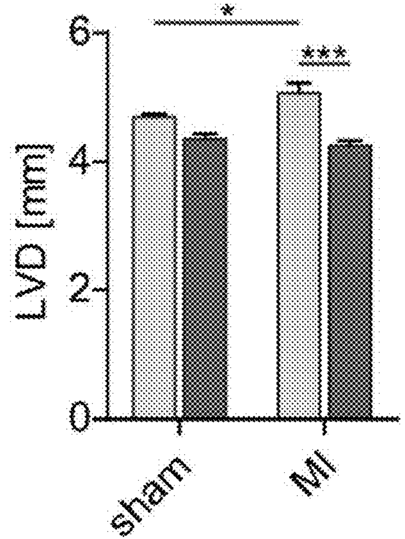
FIG. 2B shows a histogram of left ventricular diameter for the control (sham) group and the MI group.
Figure 2C:
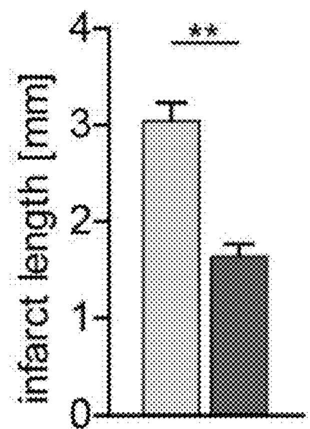
FIG. 2C shows a histogram of infarct length for the KO animals and the WT animals.
Figure 2D:
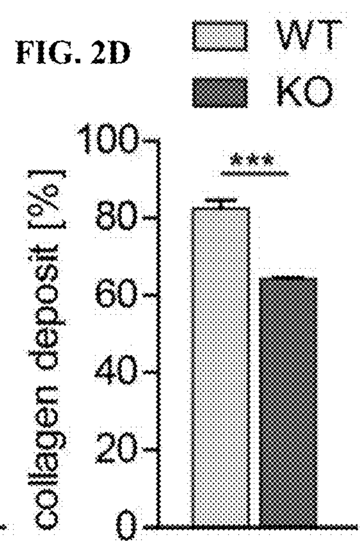
FIG. 2D shows a histogram of collagen deposit in the infarcted area for the KO animals and the WT animals.

FIGS. 2A-2D show that remodeling of the heart is regulated by CAR. Histology of the hearts 30 days after the infarction shows an increased left ventricular diameter only in the WT hearts, as shown in FIG. 2A. The left ventricular diameter was only increased in the wildtype after myocardial infarction, as shown in FIG. 2B. Infarct length, as shown in FIG. 2C, and collagen deposit in the infarcted area, as shown in FIG. 2D, as signs of pathology were reduced in the KO.

FIGS. 3A-3C show the functional analysis of the hearts. The negative effects on heart weight, as shown in FIG. 3A, ejection fraction, as shown in FIG. 3B, and left ventricular inner diameter, as shown in FIG. 3C, are more pronounced in WT animals.

FIGS. 4A and 4B show generation of soluble CAR with a morpholino directed against the transmembrane exon 6. FIG. 4A shows a schematic of the CXADR gene encoding CAR with boxes representing exons 1 to 8 and the black line indicating the introns. The binding site for the CAR Exon6 morpholino (CAR-E6) is indicated above the horizontal line representing the gene (lighter (red) bar). Normal splicing is represented by the lighter (blue) line, the splicing pattern generating soluble CAR by the lighter (red) line (connecting exons 5 and 7). FIG. 4B shows RT PCR on mRNA from C2C12 cells treated with CAR Exon6 specific morpholino results in the appearance of a lower band that indicates the isoform lacking Exon 6. Control (Ctrl) was a non-targeting morpholino. The morpholino is efficient at both 5 and 10 μmol/l. Primers are indicated as arrows (for=forward; rev=reverse). The CAR-E6 morpholino sequence is 5'-GTCTAGTTTCACTGAATTACCTGAT-3' (SEQ ID NO. 7); the standard control oligo sequence is 5'-CCTCTTACCTCAGTTACAATTTATA-3' (SEQ ID NO. 8).

FIGS. 5A-5F show that virus-like particles inhibit CAR function. FIG. 5A show plasmid pFastBacDual with the Coxsackievirus B3 (CVB3) structural proteins VP4, 2, 3, 1 and the proteases 2a and 3c (c.f. SEQ ID NOs 9-14). (B) Plasmid pFastBacDual with GFP, the CVB3 structural proteins VP4, 2, 3, 1 and the proteases 2a and 3c. FIG. 5C shows transfection of Sf21 cells with the recombinant GFP bacmid and validation of GFP expression (green). FIG. 5D shows purification of Coxsackievirus-like particles (CxVLPs) in a continuous sucrose gradient. FIG. 5E shows electron microscopy of Coxsackievirus-like particles. FIG. 5F shows uptake of GPF tagged Coxsackievirus-like particles in endothelial rBCEC4 cells. Cells expressing CAR (red) mediate internalization of Coxsackievirus-like particles (green).

EXAMPLES

Methods

Animal Model

The generation of heart specific inducible CAR knockout animals has been published previously (Lisewski, U. et al. The tight junction protein CAR regulates cardiac conduction and cell-cell communication. *J Exp Med* 205, 2369-79 (2008).). In brief, the inventors used the Cre-lox recombination system and flanked the ATG containing CAR exon 1 with lox sites. After homologous recombination blastocyst injection of targeted ES-cells was used to obtain knockout animals. The neomycin/flp resistance cassette was removed by germline expression of the FLP recombinase (Weinert et al, J Cell Biol. 2006 May 22; 173(4): 559-570). The resulting animals were verified by PCR and Southern blot. To generate the inducible heart specific CAR KO, the inventors used a transgenic mouse expressing the MerCreMer fusion protein. The inducible knockout mice (MerCreMer+ CAR-recf/recf) survive to term and depletion of CAR was induced with tamoxifen injections (30 mg/kg B.W.) as described previously (Lisewski, U. et al. The tight junction protein CAR regulates cardiac conduction and cell-cell communication. *J Exp Med* 205, 2369-79 (2008).).

Echocardiography (ECG)

For echocardiography, the inventors used the Vevo 770 system (Visual Sonics, Inc.) with a 45 MHz transducer mounted on an integrated rail system. Standard imaging planes, M-mode, Doppler and functional calculations were obtained according to American Society of Echocardiography guidelines. The LV parasternal long axis 4-chamber view was used to derive fractional shortening (% FS), ejection fraction (% EF), and ventricular dimensions and volumes. The subcostal long axis view from the left apex was used for Doppler imaging of mitral inflow and aortic ejection profiles.

Myocardial Infarction

After anesthesia with Xylazine/Ketamine (5 [mg/kg BW]/100 [mg/kg BW], i.m.), animals are intubated and respirated mechanically. For the surgery, the inventors followed the published procedure (Michael et al., Am J Physiol. 1995 Dec.; 269(6 Pt 2):H2147-54.). In brief, after left thoracotomy, the pericardium was removed. The left coronary artery was ligated 1 to 2 mm below its origin. Successful ligation was monitored by evaluating the macroscopic changes and recording of ECGs. For control treatment, the suture was not closed.

Histology

Samples of aseptically removed tissues were fixed for 12 hours in phosphate-buffered saline (pH 7.2) with 4% paraformaldehyde and embedded in paraffin. Histological analysis was performed on deparaffinized 5 μm-thick tissue sections that were stained with H&E for gross anatomy. Masson's Trichrome stain was used to visualize the degree of fibrosis. For quantification, the inventors used ImageJ software.

Morpholino Treatment and RT-PCR.

Cells at 80% confluence were seeded onto 12 well plates. The media was replaced with fresh complete DMEM and cells were treated with 5 μmol/l CAR-E6 Morpholino by endocytosis-mediated entry using 4 μmol/l Endo Porter delivery reagent for 48 hrs. Preparation of RNA and PCR has been described previously (Lisewski, U. et al. The tight junction protein CAR regulates cardiac conduction and cell-cell communication. *J Exp Med* 205, 2369-79 (2008)). The CAR-E6 morpholino sequence is 5'-GTCTAGTTTCACTGAATTACCTGAT-3' (SEQ ID NO. 7), the standard control oligo sequence is 5'-CCTCTTACCTCAGTTACAATTTATA-3' (SEQ ID NO. 8).

Statistical Analysis

For statistical analysis, GraphPad Prism software was used. Results are expressed as means±SEM. For hemodynamic data statistical significance between groups was determined using the Mann Whitney U test, for expression analysis, the inventors used an unpaired two-tailed t-test. The significance level was chosen as P=0.05.

Virus Like Particles

The viral capsid proteins VP4, VP2, VP3 VP1 and the viral protease 2a were cloned under control of the Pph promoter in the pFastBacDual plasmid. The viral protease 3c was cloned under control of the Pp10 promoter. A variant with GFP fused to VP4 was generated to follow expression and localization of the resulting particle. Plasmids were verified by PCR and sequencing. The expression construct flanked by Tn7 elements was transposed to the bacmid bMon 14272. Transfection of Sf21 cells with the bacmid resulted in recombinant Baculovirus expressing the viral capsid proteins and the proteases 2a and 3c. For Coxsackievirus-like particles (CxVLP) production Sf21 cells were infected with a multiplicity of infection (MOI) of 5 and harvested 72 h after infection. Coxsackievirus-like particles from lysed cells were purified in a continuous sucrose gradient and dissolved in PBS.

Sequences

1. Human CAR Longest transcript, CCDS ID: CCDS33519.1. (See Report for CCDS33519.1 on the National Center for Biotechnology Information (NCBI) Consensus Coding Sequence (CCDS) internet database.)

Nucleotide Sequence (1098 nt; Underlined highlighting indicates alternate exons.), SEQ ID NO. 1:

```
ATGGCGCTCCTGCTGTGCTTCGTGCTCCTGTGCGGAGTAGTGGATTTCGC
CAGAAGTTTGAGTATCACTACTCCTGAAGAGATGATTGAAAAAGCCAAAG
GGGAAACTGCCTATCTGCCATGCAAATTTACGCTTAGTCCCGAAGACCAG
GGACCGCTGGACATCGAGTGGCTGATATCACCAGCTGATAATCAGAAGGT
GGATCAAGTGATTATTTTATATTCTGGAGACAAAATTTATGATGACTACT
ATCCAGATCTGAAAGGCCGAGTACATTTTACGAGTAATGATCTCAAATCT
GGTGATGCATCAATAAATGTAACGAATTTACAACTGTCAGATATTGGCAC
ATATCAGTGCAAAGTGAAAAAAGCTCCTGGTGTTGCAAATAAGAAGATTC
ATCTGGTAGTTCTTGTTAAGCCTTCAGGTGCGAGATGTTACGTTGATGGA
TCTGAAGAAATTGGAAGTGACTTTAAGATAAAATGTGAACCAAAAGAAGG
TTCACTTCCATTACAGTATGAGTGGCAAAAATTGTCTGACTCACAGAAAA
TGCCCACTTCATGGTTAGCAGAAATGACTTCATCTGTTATATCTGTAAAA
AATGCCTCTTCTGAGTACTCTGGGACATACAGCTGTACAGTCAGAAACAG
AGTGGGCTCTGATCAGTGCCTGTTGCGTCTAAACGTTGTCCCTCCTTCAA
ATAAAGCTGGACTAATTGCAGGAGCCATTATAGGAACTTTGCTTGCTCTA
GCGCTCATTGGTCTTATCATCTTTTGCTGTCGTAAAAAGCGCAGAGAAGA
AAAATATGAAAAGGAAGTTCATCACGATATCAGGGAAGATGTGCCACCTC
CAAAGAGCCGTACGTCCACTGCCAGAAGCTACATCGGCAGTAATCATTCA
TCCCTGGGGTCCATGTCTCCTTCCAACATGGAAGGATATTCCAAGACTCA
```

-continued

GTATAACCAAGTACCAAGTGAAGACTTTGAACGCACTCCTCAGAGTCCGA

CTCTCCCACCTGCTAAGGTAGCTGCCCCTAATCTAAGTCGAATGGGTGCG

ATTCCTGTGATGATTCCAGCACAGAGCAAGGATGGGTCTATAGTATAG

Translation (protein, 365 aa; Underlined highlighting indicates alternate exons. Bold highlighting indicates amino acids encoded across a splice junction.), SEQ ID NO. 2:

MALLLCFVLLCGVVDFARSLSITTPEEMIEKAKGETAYLPCKFTLSPEDQ

GPLDIEWLISPADNQKVDQVIILYSGDKIYDDYYPDLKGRVHFTSNDLKS

GDASINVTNLQLSDIGTYQCKVKKAPGVANKKIHLVVLVKPSGARCYVDG

SEEIGSDFKIKCEPKEGSLPLQYEWQKLSDSQKMPTSWLAEMTSSVISVK

NASSEYSGTYSCTVRNRVGSDQCLLRLNVVPPSNKAGLIAGAIIGTLLAL

ALIGLIIFCCRKKRREEKYEKEVHHDIREDVPPPKSRTSTARSYIGSNHS

SLGSMSPSNMEGYSKTQYNQVPSEDFERTPQSPTLPPAKVAAPNLSRMGA

IPVMIPAQSKDGSIV

2. Human CAR-Fc:

Human CAR-Fc-cDNA (the sequence encoding CAR is underlined), SEQ ID NO. 3:

ATGGCGCTCCTGCTGTGCTTCGTGCTCCTGTGCGGAGTAGTGGATTTCGC

CAGAAGTTTGAGTATCACTACTCCTGAAGAGATGATTGAAAAAGCCAAAG

GGGAAACTGCCTATCTGCCATGCAAATTTACGCTTAGTCCCGAAGACCAG

GGACCGCTGGACATCGAGTGGCTGATATCACCAGCTGATAATCAGAAGGT

GGATCAAGTGATTATTTTATATTCTGGAGACAAAATTTATGATGACTACT

ATCCAGATCTGAAAGGCCGAGTACATTTTACGAGTAATGATCTCAAATCT

GGTGATGCATCAATAAATGTAACGAATTTACAACTGTCAGATATTGGCAC

ATATCAGTGCAAAGTGAAAAAAGCTCCTGGTGTTGCAAATAAGAAGATTC

ATCTGGTAGTTCTTGTTAAGCCTTCAGGTGCGAGATGTTACGTTGATGGA

TCTGAAGAAATTGGAAGTGACTTTAAGATAAAATGTGAACCAAAAGAAGG

TTCACTTCCATTACAGTATGAGTGGCAAAAATTGTCTGACTCACAGAAAA

TGCCCACTTCATGGTTAGCAGAAATGACTTCATCTGTTATATCTGTAAAA

AATGCCTCTTCTGAGTACTCTGGGACATACAGCTGTACAGTCAGAAACAG

AGTGGGCTCTGATCAGTGCCTGTTGCGTCTAAACGTTGTCCCTCCTTCAA

ATAAAGCTGCCACCGGTGACGTCGAGTCCAAATCTTGTGACAAAACTCAC

ACATGCCCACCGTGCCCAGCACCTGAACTCCTGGGGGGACCGTCAGTCTT

CCTCTTCCCCCCAAAACCCAAGGACACCCTCATGATCTCCCGGACCCCTG

AGGTCACATGCGTGGTGGTGGACGTGAGCCACGAAGACCCTGAGGTCAAG

TTCAACTGGTACGTGGACGGCGTGGAGGTGCATAATGCCAAGACAAAGCC

GCGGGAGGAGCAGTACAACAGCACGTACCGTGTGGTCAGCGTCCTCACCG

TCCTGCACCAGGACTGGCTGAATGGCAAGGAGTACAAGTGCAAGGTCTCC

AACAAAGCCCTCCCAGCCCCCATCGAGAAAACCATCTCCAAAGCCAAAGG

GCAGCCCCGAGAGCCACAGGTGTACACCCTGCCCCCATCCCGGGATGAGC

TGACCAAGAACCAGGTCAGCCTGACCTGCCTGGTCAAAGGCTTCTATCCC

-continued

AGCGACATCGCCGTGGAGTGGGAGAGCAATGGGCAGCCGGAGAACAACTA

CAAGACCACGCCTCCCGTGCTGGACTCCGACGGCTCCTTCTTCCTCTACA

GCAAGCTCACCGTGGACAAGAGCAGGTGGCAGCAGGGGAACGTCTTCTCA

TGCTCCGTGATGCATGAGGCTCTGCACAACCACTACACGCAGAAGAGCCT

CTCCCTGTCTCCGGGTAAATGA

Amino acid (the sequence encoding CAR is underlined), SEQ ID NO. 4:

MALLLCFVLLCGVVDFARSLSITTPEEMIEKAKGETAYLPCKFTLSPEDQ

GPLDIEWLISPADNQKVDQVIILYSGDKIYDDYYPDLKGRVHFTSNDLKS

GDASINVTNLQLSDIGTYQCKVKKAPGVANKKIHLVVLVKPSGARCYVDG

SEEIGSDFKIKCEPKEGSLPLQYEWQKLSDSQKMPTSWLAEMTSSVISVK

NASSEYSGTYSCTVRNRVGSDQCLLRLNVVPPSNKATGDVESKSCDKTHT

CPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK

3. Mouse FcCAR

Mouse CAR-Fc-cDNA (the sequence encoding CAR is underlined), SEQ ID NO. 5:

ATGGCGCGCCTACTGTGCTTCGTGCTCTTGTGCGGGATCGCGGATTTCAC

CAGTGGTTTGAGCATCACTACACCCGAACAGAGGATCGAAAAAGCCAAAG

GGGAAACTGCGTATCTACCATGCAAGTTTACTCTCAGTCCCGAAGACCAG

GGACCACTGGACATTGAATGGCTGATATCCCCGTCTGATAACCAGATAGT

GGATCAAGTGATCATTTTGTATTCTGGAGACAAAATTTATGATAACTACT

ATCCGGATCTGAAAGGACGGGTACATTTTACGAGTAACGATGTCAAGTCT

GGCGACGCATCTATAAATGTGACCAACCTGCAGCTGTCGGACATTGGCAC

TTACCAGTGCAAAGTGAAGAAAGCCCCTGGGGTTGCAAATAAGAAATTCC

TGCTGACCGTTCTTGTTAAGCCTTCAGGTACAAGATGCTTCGTGGATGGA

TCGGAAGAGATTGGAAATGACTTCAAGCTAAAATGTGAACCCAAGGAAGG

CTCCCTTCCACTACAGTTTGAATGGCAGAAACTGTCGGACTCCCAGACAA

TGCCTACGCCATGGCTGGCAGAAATGACGTCACCAGTTATATCTGTGAAG

AACGCCAGTTCTGAGTATTCTGGGACATACAGCTGCACGGTTCAAAACAG

AGTGGGCTCTGACCAGTGTATGCTGCGACTAGACGTTGTCCCACCCTCCA

ACCGAGCCACCGGTGACGTCGAGTCCAAATCTTGTGACAAAACTCACACA

TGCCCACCGTGCCCAGCACCTGAACTCCTGGGGGGACCGTCAGTCTTCCT

CTTCCCCCCAAAACCCAAGGACACCCTCATGATCTCCCGGACCCCTGAGG

TCACATGCGTGGTGGTGGACGTGAGCCACGAAGACCCTGAGGTCAAGTTC

AACTGGTACGTGGACGGCGTGGAGGTGCATAATGCCAAGACAAAGCCGCG

GGAGGAGCAGTACAACAGCACGTACCGTGTGGTCAGCGTCCTCACCGTCC

-continued

```
TGCACCAGGACTGGCTGAATGGCAAGGAGTACAAGTGCAAGGTCTCCAAC
AAAGCCCTCCCAGCCCCCATCGAGAAAACCATCTCCAAAGCCAAAGGGCA
GCCCCGAGAGCCACAGGTGTACACCCTGCCCCCATCCCGGGATGAGCTGA
CCAAGAACCAGGTCAGCCTGACCTGCCTGGTCAAAGGCTTCTATCCCAGC
GACATCGCCGTGGAGTGGGAGAGCAATGGGCAGCCGGAGAACAACTACAA
GACCACGCCTCCCGTGCTGGACTCCGACGGCTCCTTCTTCCTCTACAGCA
AGCTCACCGTGGACAAGAGCAGGTGGCAGCAGGGGAACGTCTTCTCATGC
TCCGTGATGCATGAGGCTCTGCACAACCACTACACGCAGAAGAGCCTCTC
CCTGTCTCCGGGTAAATGA
```

Amino acid (the sequence encoding CAR is underlined), SEQ ID NO. 6:

```
MARLLCFVLLCGIADFTSGLSITTPEQRIEKAKGETAYLPCKFTLSPEDQ
GPLDIEWLISPSDNQIVDQVIILYSGDKIYDNYYPDLKGRVHFTSNDVKS
GDASINVTNLQLSDIGTYQCKVKKAPGVANKKFLLTVLVKPSGTRCFVDG
SEEIGNDFKLKCEPKEGSLPLQFEWQKLSDSQTMPTPWLAEMTSPVISVK
NASSEYSGTYSCTVQNRVGSDQCMLRLDVVPPSNRATGDVESKSCDKTHT
CPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSC
SVMHEALHNHYTQKSLSLSPGK
```

4. Morpholinos

CAR-E6 morpholino sequence, SEQ ID NO. 7:

```
GTCTAGTTTCACTGAATTACCTGAT
```

Standard control morpholino sequence, SEQ ID NO. 8:

```
CCTCTTACCTCAGTTACAATTTATA
```

5. Coxsackievirus-Like Particles

CVB3 P1 (VP4, VP2, VP3, VP1), 2A cDNA sequence (3000 nt, Underlined highlighting indicates alternate proteins.), SEQ ID NO. 9:

```
ATGGGAGCTCAAGTATCAACGCAAAAGACTGGGGCACATGAGACCGGGCT
GAATGCTAGCGGCAATTCCATCATTCACTACACAAATATTAATTATTACA
AGGATGCCGCATCCAACTCAGCCAATCGGCAGGATTTCACTCAAGACCCG
GGCAAGTTCACAGAACCAGTAAAAGATATCATGATTAAATCACTACCAGC
TCTCAACTCCCCCACAGTAGAGGAGTGCGGATACAGTGACAGGGCGAGAT
CAATCACATTAGGTAACTCCACCATAACGACTCAGGAATGCGCCAACGTG
GTGGTGGGCTATGGAGTATGGCCAGATTATCTAAAGGATAGTGAGGCAAC
AGCAGAGGACCAACCGACCCAACCAGACGTTGCCACATGTAGGTTCTATA
CCCTTGACTCTGTGCAATGGCAGAAAACCTCACCAGGATGGTGGTGGAAG
```

-continued

```
CTGCCCGATGCTTTGTCGAACTTAGGACTGTTTGGGCAGAACATGCAGTA
CCACTACTTAGGCCGAACTGGGTATACCGATCATGTGCAGTGCAATGCAT
CTAAGTTCCACCAAGGATGCTTGCTAGTAGTGTGTGTACCGGAAGCTGAG
ATGGGTTGCGCAACGCTAGACAACACCCCATCCAGTGCAGAATTGCTGGG
GGGCGATACGGCAAAAGAGTTTGCGGACAAACCGGTCGCATCCGGGTCCA
ACAAGTTGGTACAGAGGGTGGTGTATAATGCAGGCATGGGGGTGGGTGTT
GGAAACCTCACCATTTTCCCCCACCAATGGATCAACCTACGCACCAATAA
TAGTGCTACAATTGTGATGCCATACACCAACAGTGTACCTATGGATAACA
TGTTTAGGCATAACAACGTCACCCTAATGGTTATCCCATTTGTACCGCTA
GATTACTGCCCTGGGTCCACCACGTACGTCCCAATTACGGTCACGATAGC
CCCAATGTGTGCCGAGTACAATGGGTTACGTTTAGCAGGGCACCAGGGCT
TACCAACCATGAATACTCCGGGGAGCTGTCAATTTCTGACATCAGACGAC
TTCCAATCACCATCCGCCATGCCGCAATATGACGTCACACCAGAGATGAG
GATACCTGGTGAGGTGAAAAACTTGATGGAAATAGCTGAGGTTGACTCAG
TTGTCCCAGTCCAAAATGTTGGAGAGAAGGTCAACTCTATGGAAGCATAC
CAGATACCTGTGAGATCCAATGAAGGATCTGGAACGCAAGTATTCGGCTT
TCCACTGCAACCAGGGTACTCGAGTGTTTTTAGTCGGACGCTCCTAGGAG
AGATCTTGAACTATTATACACATTGGTCAGGCAGCATAAAGCTTACGTTT
ATGTTCTGTGGTTCGGCCATGGCTACTGGAAAATTCCTTTTGGCATACTC
ACCACTAGGTGCTGGAGCTCCTACAAAAAGGGTTGATGCCATGCTTGGTA
CTCATGTAGTTTGGGACGTGGGGCTACAATCAAGTTGCGTGCTGTGTATA
CCCTGGATAAGCCAAACACACTACCGGTATGTTGCTTCAGATGAGTGTAC
CGCAGGGGGTTTATTACGTGCTGGTATCAAACAAACATAGTGGTCCCAG
CGGATGCCCAAAGCTCCTGTTACATCATGTGTTTCGTGTCAGCATGCAAT
GACTTCTCTGTCAGGCTATTGAAGGACACTCCTTTCATTTCGCAGGAAAA
CTTTTTCCAGGGCCCAGTGGAAGACGCGATAACAGCCGCTATAGGGAGAG
TTGCGGATACCGTGGGTACAGGGCCAAACAACTCAGAAGCTATACCAGCA
CTCACTGCTGCTGAGACAGGTCACACGTCACAAGTAGTGCCGGGTGACAC
CATGCAGACACGCCACGTTAAGAACTACCATTCAAGGTCCGAGTCAACCA
TAGAGAACTTCCTATGTAGGTCAGCATGCGTGTACTTTACGGAGTATGAA
AACTCAGGTGCCAAGCGGTATGCTGAATGGGTATTAACACCACGACAAGC
AGCACAACTTAGGAGAAAGCTAGAATTCTTTACCTACGTCCGGTTCGACC
TGGAGCTGACGTTTGTCATAACAAGTACTCAACAGCCCTCAACCACACAG
AACCAAGACGCACAGATCCTAACACACCAAATTATGTATGTACCACCAGG
TGGACCTGTACCAGATAAAGTTGATTCATACGTGTGGCAAACATCTACGA
ATCCCAGTGTGTTTTGGACCGAGGGAAACGCCCCGCCGCGCATGTCCATA
CCGTTTTTGAGCATTGGCAACGCCTATTCAAATTTCTATGACGGATGGTC
TGAATTTTCCAGGAACGGAGTTTACGGCATCAACACGCTAAACAACATGG
GCACGCTATATGCAAGACATGTCAACGCTGGAAGCACGGGTCCAATAAAA
AGCACCATTAGAATCTACTTCAAACCGAAGCATGTCAAAGCGTGGATACC
TAGACCACCTAGACTCTGCCAATACGAGAAGGCAAAGAACGTGAACTTCC
```

-continued

AACCCAGCGGAGTTACCACTACTAGGCAAAGCATCACTACAATGACAAAT

ACGGGCGCAATTTGGACAACAATCAGGGGCAGTGTATGTGGGGACTACAG

GGTAGTAAATAGACACTCAGCTACCAGTGCTGACTGGCAAAACTGTGTGT

GGGAAAGTTACAACAGAGACCTCTTAGTGAGCACGACCACAGCACATGGA

TGTGATATTATAGCCAGATGTCAGTGCACAACGGGAGTGTACTTTTGTGC

GTCCAAAAACAAGCACTACCCAATTTCGTTTGAAGGACCAGGTCTAGTAG

AGGTCCAAGAGAGTGAATACTACCCCAGGAGATACCAATCCCATGTGCTT

TTAGCAGCTGGATTTTCCGAACCAGGTGACTGTGGCGGTATCCTAAGGTG

TGAGCATGGTGTCATTGGCATTGTGACCATGGGGGGTGAAGGCGTGGTCG

GCTTTGCAGACATCCGTGATCTCCTGTGGCTGGAAGATGATGCAATGGAA

CVB3 P1 amino acid sequence (1001 aa), SEQ ID NO. 10:

MGAQVSTQKTGAHETRLNASGNSIIHYTNINYYKDAASNSANRQDFTQDP

GKFTEPVKDIMIKSLPALNSPTVEECGYSDRARSITLGNSTITTQECANV

VVGYGVWPDYLKDSEATAEDQPTQPDVATCRFYTLDSVQWQKTSPGWWWK

LPDALSNLGLFGQNMQYHYLGRTGYTVHVQCNASKFHQGCLLVVCVPEAE

MGCATLDNTPSSAELLGGDTAKEFADKPVASGSNKLVQRVVYNAGMGVGV

GNLTIFPHQWINLRTNNSATIVMPYTNSVPMDNMFRHNNVTLMVIPFVPL

DYCPGSTTYVPITVTIAPMCAEYNGLRLAGHQGLPTMNTPGSCQFLTSDD

FQSPSAMPQYDVTPEMRIPGEVKNLMEIAEVDSVVPVQNVGEKVNSMEAY

QIPVRSNEGSGTQVFGFPLQPGYSSVFSRTLLGEILNYYTHWSGSIKLTF

MFCGSAMATGKFLLAYSPPGAGAPTKRVDAMLGTHVIWDVGLQSSCVLCI

PWISQTHYRFVASDEYTAGGFITCWYQTNIVVPADAQSSCYIMCFVSACN

DFSVRLLKDTPFISQQNFFQQPVEDAITAAIGRVADTVGTGPTNSEAIPA

LTAAETGHTSQVVPGDTMQTRHVKNYHSRSESTIENFLCRSACVYFTEYK

NSGAKRYAEWVLTPRQAAQLRRKLEFFTYVRFDLELTFVITSTQQPSTTQ

NQDAQILTHQIMYVPPGGPVPDKVDSYVWQTSTNPSVFWTEGNAPPRMSI

PFLSIGNAYSNFYDGWSEFSRNGVYGINTLNNMGTLYARHVNAGSTGPIK

STIRIYFKPKHVKAWIPRPPRLCQYEKAKNVNFQPSGVTTTRQSITTMTN

TGAFGQQSGAVYVGNYRVVNRHLATSADWQNCVWESYNRDLLVSTTTAHG

CDIIARCQCTTGVYFCASKNKHYPISFEGPGLVEVQESEYYPRRYQSHVL

LAAGFSEPGDCGGILRCEHGVIGIVTMGGEGVVGFADIRDLLWLEDDAME

Q

CVB3 3c protease cDNA sequence (549 nt), SEQ ID NO. 11:

GGCCCTGCCTTTGAGTTCGCCGTCGCAATGATGAAAAGGAACTCAAGCAC

GGTGAAAACTGAATATGGCGAGTTTACCATGCTGGGCATCTATGACAGGT

GGGCCGTTTTGCCACGCCACGCCAAACCTGGGCCAACCATCTTGATGAAT

GATCAAGAGGTTGGTGTGCTAGATGCCAAGGAGCTAGTAGACAAGGATGG

-continued

CACCAACTTAGAACTGACACTACTCGAATTGAACCGGAATGAGAAGTTCG

GAGACATCGGAGGCTTCGTAGCCAAGGAGGAAGTGGAGGTTAATGAGGCA

GTGCTAGCAATTAACACCAGCAAGTTTCCCAACATGTACATTCCAGTAGG

ACAGGTCACAGAATACGGCTTCCTAAACCTAGGTGGCACACCCACCAAGA

GAATGCTTATGTACAACTTCCCCACAAGAGCAGGCCAGTGTGGTGGAGTG

CTCATGTCCACCGGCAAGGTACTGGGTATCCATGTTGGTGGAAATGGCCA

TCAGGGCTTCTCAGCAGCACTCCTCAAACACAACTTCAATGATGAGCAA

CVB3 3c protease amino acid sequence (protein, 180 aa), SEQ ID NO. 12:

GPAFEFAVAMMKRNSSTVKTEYGEFTMLGIYDRWAVLPRHAKPGPTILMN

DQEVGVLDAKELVDKDGTNLELTLLKLNRNEKFRDIRGFLAKEEVEVNEA

VLAINTSKFPNMYIPVGQVTEYGFLNLGGTPTKRMLMYNFPTRAGQCGGV

LMSTGKVLGIHVGGNGHQGFSAALLKHYFN

GFP, CVB3 P1, 2a fusion protein cDNA sequence (3717 nt; Underlined highlighting indicates alternate proteins.), SEQ ID NO. 13:

ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGATGGGAGCTCAAGTATCAACGCAAAAGACTGGG

GCACATGAGACCGGGCTGAATGCTAGCGGCAATTCCATCATTCACTACAC

AAATATTAATTATTACAAGGATGCCGCATCCAACTCAGCCAATCGGCAGG

ATTTCACTCAAGACCCGGGCAAGTTCACAGAACCAGTAAAAGATATCATG

ATTAAATCACTACCAGCTCTCAACTCCCCCACAGTAGAGGAGTGCGGATA

CAGTGACAGGGCGAGATCAATCACATTAGGTAACTCCACCATAACGACTC

AGGAATGCGCCAACGTGGTGGTGGGCTATGGAGTATGGCCAGATTATCTA

AAGGATAGTGAGGCAACAGCAGAGGACCAACCGACCCAACCAGACGTTGC

CACATGTAGGTTCTATACCCTTGACTCTGTGCAATGGCAGAAAACCTCAC

CAGGATGGTGGTGGAAGCTGCCCGATGCTTTGTCGAACTTAGGACTGTTT

-continued

GGGCAGAACATGCAGTACCACTACTTAGGCCGAACTGGGTATACCGATCA
TGTGCAGTGCAATGCATCTAAGTTCCACCAAGGATGCTTGCTAGTAGTGT
GTGTACCGGAAGCTGAGATGGGTTGCGCAACGCTAGACAACACCCCATCC
AGTGCAGAATTGCTGGGGGGCGATACGGCAAAAGAGTTTGCGGACAAACC
GGTCGCATCCGGGTCCAACAAGTTGGTACAGAGGGTGGTGTATAATGCAG
GCATGGGGGTGGGTGTTGGAAACCTCACCATTTTCCCCCACCAATGGATC
AACCTACGCACCAATAATAGTGCTACAATTGTGATGCCATACACCAACAG
TGTACCTATGGATAACATGTTTAGGCATAACAACGTCACCCTAATGGTTA
TCCCATTTGTACCGCTAGATTACTGCCCTGGGTCCACCACGTACGTCCCA
ATTACGGTCACGATAGCCCCAATGTGTGCCGAGTACAATGGGTTACGTTT
AGCAGGGCACCAGGGCTTACCAACCATGAATACTCCGGGGAGCTGTCAAT
TTCTGACATCAGACGACTTCCAATCACCATCCGCCATGCCGCAATATGAC
GTCACACCAGAGATGAGGATACCTGGTGAGGTGAAAAACTTGATGGAAAT
AGCTGAGGTTGACTCAGTTGTCCCAGTCCAAAATGTTGGAGAGAAGGTCA
ACTCTATGGAAGCATACCAGATACCTGTGAGATCCAATGAAGGATCTGGA
ACGCAAGTATTCGGCTTTCCACTGCAACCAGGGTACTCGAGTGTTTTTAG
TCGGACGCTCCTAGGAGAGATCTTGAACTATTATACACATTGGTCAGGCA
GCATAAAGCTTACGTTTATGTTCTGTGGTTCGGCCATGGCTACTGGAAAA
TTCCTTTTGGCATACTCACCACTAGGTGCTGGAGCTCCTACAAAAAGGGT
TGATGCCATGCTTGGTACTCATGTAGTTTGGGACGTGGGGCTACAATCAA
GTTGCGTGCTGTGTATACCCTGGATAAGCCAAACACACTACCGGTATGTT
GCTTCAGATGAGTGTACCGCAGGGGGTTTATTACGTGCTGGTATCAAAC
AAACATAGTGGTCCCAGCGGATGCCCAAAGCTCCTGTTACATCATGTGTT
TCGTGTCAGCATGCAATGACTTCTCTGTCAGGCTATTGAAGGACACTCCT
TTCATTTCGCAGGAAAACTTTTTCCAGGGCCCAGTGGAAGACGCGATAAC
AGCCGCTATAGGGAGAGTTGCGGATACCGTGGGTACAGGGCCAAACAACT
CAGAAGCTATACCAGCACTCACTGCTGCTGAGACAGGTCACACGTCACAA
GTAGTGCCGGGTGACACCATGCAGACACGCCACGTTAAGAACTACCATTC
AAGGTCCGAGTCAACCATAGAGAACTTCCTATGTAGGTCAGCATGCGTGT
ACTTTACGGAGTATGAAAACTCAGGTGCCAAGCGGTATGCTGAATGGGTA
TTAACACCACGACAAGCAGCACAACTTAGGAGAAAGCTAGAATTCTTTAC
CTACGTCCGGTTCGACCTGGAGCTGACGTTTGTCATAACAAGTACTCAAC
AGCCCTCAACCACACAGAACCAAGACGCACAGATCCTAACACACCAAATT
ATGTATGTACCACCAGGTGGACCTGTACCAGATAAAGTTGATTCATACGT
GTGGCAAACATCTACGAATCCCAGTGTGTTTTGGACCGAGGGAAACGCCC
CGCCGCGCATGTCCATACCGTTTTTGAGCATTGGCAACGCCTATTCAAAT
TTCTATGACGGATGGTCTGAATTTTCCAGGAACGGAGTTTACGGCATCAA
CACGCTAAACAACATGGGCACGCTATATGCAAGACATGTCAACGCTGGAA
GCACGGGTCCAATAAAAAGCACCATTAGAATCTACTTCAAACCGAAGCAT
GTCAAAGCGTGGATACCTAGACCACCTAGACTCTGCCAATACGAGAAGGC
AAAGAACGTGAACTTCCAACCCAGCGGAGTTACCACTACTAGGCAAAGCA
TCACTACAATGACAAATACGGGCGCAATTTGGACAACAATCAGGGGCAGT
GTATGTGGGGACTACAGGGTAGTAAATAGACACTCAGCTACCAGTGCTGA
CTGGCAAAACTGTGTGTGGGAAAGTTACAACAGAGACCTCTTAGTGAGCA
CGACCACAGCACATGGATGTGATATTATAGCCAGATGTCAGTGCACAACG
GGAGTGTACTTTTGTGCGTCCAAAAACAAGCACTACCCAATTTCGTTTGA
AGGACCAGGTCTAGTAGAGGTCCAAGAGAGTGAATACTACCCCAGGAGAT
ACCAATCCCATGTGCTTTTAGCAGCTGGATTTTCCGAACCAGGTGACTGT
GGCGGTATCCTAAGGTGTGAGCATGGTGTCATTGGCATTGTGACCATGGG
GGGTGAAGGCGTGGTCGGCTTTGCAGACATCCGTGATCTCCTGTGGCTGG
AAGATGATGCAATGGAA

GFP, CVB3 P1, 2a fusion protein, amino acid sequence (1240 aa), SEQ ID NO. 14:

MVSKGEELFTGVVPILVELDGDVNGHKFSVSGEGEGDATYGKLTLKFICT
TGKLPVPWPTLVTTLTYGVQCFSRYPDHMKQHDFFKSAMPEGYVQERTIF
FKDDGNYKTRAEVKFEGDTLVNRIELKGIDFKEDGNILGHKLEYNYNSHN
VYIMADKQKNGIKVNFKIRHNIEDGSVQLADHYQQNTPIGDGPVLLPDNH
YLSTQSALSKDPNEKRDHMVLLEFVTAAGITLGMDELYKMGAQVSTQKTG
AHETRLNASGNSIIHYTNINYYKDAASNSANRQDFTQDPGKFTEPVKDIM
IKSLPALNSPTVEECGYSDRARSITLGNSTITTQECANVVVGYGVWPDYL
KDSEATAEDQPTQPDVATCRFYTLDSVQWQKTSPGWWWKLPDALSNLGLF
GQNMQYHYLGRTGYTVHVQCNASKFHQGCLLVVCVPEAEMGCATLDNTPS
SAELLGGDTAKEFADKPVASGSNKLVQRVVYNAGMGVGVGNLTIFPHQWI
NLRTNNSATIVMPYTNSVPMDNMFRHNNVTLMVIPFVPLDYCPGSTTYVP
ITVTIAPMCAEYNGLRLAGHQGLPTMNTPGSCQFLTSDDFQSPSAMPQYD
VTPEMRIPGEVKNLMEIAEVDSVVPVQNVGEKVNSMEAYQIPVRSNEGSG
TQVFGFPLQPGYSSVFSRTLLGEILNYYTHWSGSIKLTFMFCGSAMATGK
FLLAYSPPGAGAPTKRVDAMLGTHVIWDVGLQSSCVLCIPWISQTHYRFV
ASDEYTAGGFITCWYQTNIVVPADAQSSCYIMCFVSACNDFSVRLLKDTP
FISQQNFFQGPVEDAITAAIGRVADTVGTGPTNSEAIPALTAAETGHTSQ
VVPGDTMQTRHVKNYHSRSESTIENFLCRSACVYFTEYKNSGAKRYAEWV
LTPRQAAQLRRKLEFFTYVRFDLELTFVITSTQQPSTTQNQDAQILTHQI
MYVPPGGPVPDKVDSYVWQTSTNPSVFWTEGNAPPRMSIPFLSIGNAYSN
FYDGWSEFSRNGVYGINTLNNMGTLYARHVNAGSTGPIKSTIRIYFKPKH
VKAWIPRPPRLCQYEKAKNVNFQPSGVTTTRQSITTMTNTGAFGQQSGAV
YVGNYRVVNRHLATSADWQNCVWESYNRDLLVSTTTAHGCDIIARCQCTT
GVYFCASKNKHYPISFEGPGLVEVQESEYYPRRYQSHVLLAAGFSEPGDC
GGILRCEHGVIGIVTMGGEGVVGFADIRDLLWLEDDAMEQ

6. Adenovirus-fiber

Human Adenovirus C L5 capsid protein IV, cDNA sequence (1799 nt), SEQ ID NO. 15:

ATTCCTCATGTTCTTGTCCCTCCGCACCCACTATCTTCATATTGTTGCAG

ATGAAACGCGCCAGACCGTCTGAAGACACCTTCAACCCCGTGTATCCATA

TGACACAGAAACCGGGCCTCCAACTGTGCCCTTTCTTACCCCTCCATTTG

TTTCACCCAATGGTTTCCAAGAAAGTCCCCCTGGAGTTCTCTCTCTACGC

GTCTCCGAACCTTTGGACACCTCCCACGGCATGCTTGCGCTTAAAATGGG

CAGCGGTCTTACCCTAGACAAGGCCGGAAACCTCACCTCCCAAAATGTAA

CCACTGTTACTCAGCCACTTAAAAAAACAAAGTCAAACATAAGTTTGGAC

ACCTCCGCACCACTTACAATTACCTCAGGCGCCCTAACAGTGGCAACCAC

CGCTCCTCTGATAGTTACTAGCGGCGCTCTTAGCGTACAGTCACAAGCCC

CACTGACCGTGCAAGACTCCAAACTAAGCATTGCTACTAAAGGGCCCATT

ACAGTGTCAGATGGAAAGCTAGCCCTGCAAACATCAGCCCCCCTCTCTGG

CAGTGACAGCGACACCCTTACTGTAACTGCATCACCCCCGCTAACTACTG

CCACGGGTAGCTTGGGCATTAACATGGAAGATCCTATTTATGTAAATAAT

GGAAAAATAGGAATTAAAATAAGCGGTCCTTTGCAAGTAGCACAAAACTC

CGATACACTAACAGTAGTTACTGGACCAGGTGTCACCGTTGAACAAAACT

CCCTTAGAACCAAAGTTGCAGGAGCTATTGGTTATGATTCATCAAACAAC

ATGGAAATTAAAACGGGCGGTGGCATGCGTATAAATAACAACTTGTTAAT

TCTAGATGTGGATTACCCATTTGATGCTCAAACAAAACTACGTCTTAAAC

TGGGGCAGGGACCCCTGTATATTAATGCATCTCATAACTTGGACATAAAC

TATAACAGAGGCCTATACCTTTTTAATGCATCAAACAATACTAAAAAACT

GGAAGTTAGCATAAAAAAATCCAGTGGACTAAACTTTGATAATACTGCCA

TAGCTATAAATGCAGGAAAGGGTCTGGAGTTTGATACAAACACATCTGAG

TCTCCAGATATCAACCCAATAAAAACTAAAATTGGCTCTGGCATTGATTA

CAATGAAAACGGTGCCATGATTACTAAACTTGGAGCGGGTTTAAGCTTTG

ACAACTCAGGGGCCATTACAATAGGAAACAAAAATGATGACAAACTTACC

CTGTGGACAACCCCAGACCCATCTCCTAACTGCAGAATTCATTCAGATAA

TGACTGCAAATTTACTTTGGTTCTTACAAAATGTGGGAGTCAAGTACTAG

CTACTGTAGCTGCTTTGGCTGTATCTGGAGATCTTTCATCCATGACAGGC

ACCGTTGCAAGTGTTAGTATATTCCTTAGATTTGACCAAAACGGTGTTCT

AATGGAGAACTCCTCACTTAAAAAACATTACTGGAACTTTAGAAATGGGA

ACTCAACTAATGCAAATCCATACACAAATGCAGTTGGATTTATGCCTAAC

CTTCTAGCCTATCCAAAAACCCAAAGTCAAACTGCTAAAAATAACATTGT

CAGTCAAGTTTACTTGCATGGTGATAAAACTAAACCTATGATACTTACCA

TTACACTTAATGGCACTAGTGAATCCACAGAAACTAGCGAGGTAAGCACT

TACTCTATGTCTTTTACATGGTCCTGGGAAAGTGGAAAATACACCACTGA

AACTTTTGCTACCAACTCTTACACCTTCTCCTACATTGCCCAGGAATAA

Human Adenovirus C L5 capsid protein IV, amino acid sequence (582 aa), SEQ ID NO. 16:

MKRARPSEDTFNPVYPYDTETGPPTVPFLTPPFVSPNGFQESPPGVLSLR

VSEPLDTSHGMLALKMGSGLTLDKAGNLTSQNVTTVTQPLKKTKSNISLD

-continued

TSAPLTITSGALTVATTAPLIVTSGALSVQSQAPLTVQDSKLSIATKGPI

TVSDGKLALQTSAPLSGSDSDTLTVTASPPLTTATGSLGINMEDPIYVNN

GKIGIKISGPLQVAQNSDTLTVVTGPGVTVEQNSLRTKVAGAIGYDSSNN

MEIKTGGGMRINNNLLILDVDYPFDAQTKLRLKLGQGPLYINASHNLDIN

YNRGLYLFNASNNTKKLEVSIKKSSGLNFDNTAIAINAGKGLEFDTNTSE

SPDINPIKTKIGSGIDYNENGAMITKLGAGLSFDNSGAITIGNKNDDKLT

LWTTPDPSPNCRIHSDNDCKFTLVLTKCGSQVLATVAALAVSGDLSSMTG

TVASVSIFLRFDQNGVLMENSSLKKHYWNFRNGNSTNANPYTNAVGFMPN

LLAYPKTQSQTAKNNIVSQVYLHGDKTKPMILTITLNGTSESTETSEVST

YSMSFTWSWESGKYTTETFATNSYTFSYIAQE

7. Zona Occludens 1

ZO1, nucleotide sequence (5247 nt), SEQ ID NO. 17:

ATGTCCGCCAGAGCTGCGGCCGCCAAGAGCACAGCAATGGAGGAAACAGC

TATATGGGAACAACATACAGTGACGCTTCACAGGGCTCCTGGATTTGGAT

TTGGAATTGCAATATCTGGTGGACGAGATAATCCTCATTTTCAGAGTGGG

GAAACGTCAATAGTGATTTCAGATGTGCTGAAAGGAGGACCAGCTGAAGG

ACAGCTACAGGAAAATGACCGAGTTGCAATGGTTAACGGAGTTTCAATGG

ATAATGTTGAACATGCTTTTGCTGTTCAGCAACTAAGGAAAAGTGGGAAA

AATGCAAAAATTACAATTAGAAGGAAGAAGAAAGTTCAAATACCAGTAAG

TCGTCCTGATCCTGAACCAGTATCTGATAATGAAGAAGATAGTTATGATG

AGGAAATACATGATCCAAGAAGTGGCCGGAGTGGTGTGGTTAACAGAAGG

AGTGAGAAGATTTGGCCGAGGGATAGAAGTGCAAGTAGAGAGAGGAGCTT

GTCCCCGCGGTCAGACAGGCGGTCAGTGGCTTCCAGCCAGCCTGCTAAAC

CTACTAAAGTCACACTGGTGAAATCCCGGAAAAATGAAGAATATGGTCTT

CGATTGGCAAGCCATATATTTGTTAAGGAAATTTCACAAGATAGTTTGGC

AGCAAGAGATGGCAATATTCAAGAAGGTGATGTTGTATTGAAGATAAATG

GTACTGTGACAGAAAATATGTCATTGACAGATGCAAAGACATTGATAGAA

AGGTCTAAAGGCAAATTAAAAATGGTAGTTCAAAGAGATGAACGGGCTAC

GCTATTGAATGTCCCTGATCTTTCTGACAGCATCCACTCTGCTAATGCCT

CTGAGAGAGACGACATTTCAGAAATTCAGTCACTGGCATCAGATCATTCT

GGTCGATCACACGATAGGCCTCCCCGCCGCAGCCGGTCACGATCTCCTGA

CCAGCGGTCAGAGCCTTCTGATCATTCCAGGCACTCGCCGCAGCAGCCAA

GCAATGGCAGTCTCCGGAGTAGAGATGAAGAGAGAATTTCTAAACCTGGG

GCTGTCTCAACTCCTGTAAAGCATGCTGATGATCACACACCTAAAACAGT

GGAAGAAGTTACAGTTGAAAGAAATGAGAAACAAACACCTTCTCTTCCAG

AACCAAAGCCTGTGTATGCCCAAGTTGGGCAACCAGATGTGGATTTACCT

GTCAGTCCATCTGATGGTGTCCTACCTAATTCAACTCATGAAGATGGGAT

TCTTCGGCCCAGCATGAAATTGGTAAAATTCAGAAAAGGAGATAGTGTGG

GTTTGCGGCTGGCTGGTGGAAATGATGTTGGAATATTTGTAGCTGGCGTT

CTAGAAGATAGCCCTGCAGCCAAGGAAGGCTTAGAGGAAGGTGATCAAAT

-continued

TCTCAGGGTAAACAACGTAGATTTTACAAATATCATAAGAGAAGAAGCCG

TCCTTTTCCTGCTTGACCTCCCTAAAGGAGAAGAAGTGACCATATTGGCT

CAGAAGAAGAAGGATGTTTATCGTCGCATTGTAGAATCAGATGTAGGAGA

TTCTTTCTATATTAGAACCCATTTTGAATATGAAAAGGAATCTCCCTATG

GACTTAGTTTTAACAAAGGAGAGGTGTTCCGTGTTGTGGATACCTTGTAC

AATGGAAAACTGGGCTCTTGGCTTGCTATTCGAATTGGTAAAAATCATAA

GGAGGTAGAACGAGGCATCATCCCTAATAAGAACAGAGCTGAGCAGCTAG

CCAGTGTACAGTATACACTTCCAAAAACAGCAGGCGGAGACCGTGCTGAC

TTCTGGAGATTCAGAGGTCTTCGCAGCTCCAAGAGAAATCTTCGAAAAAG

CAGAGAGGATTTGTCCGCTCAGCCTGTTCAAACAAAGTTTCCAGCTTATG

AAAGAGTGGTTCTTCGAGAAGCTGGATTTCTGAGGCCTGTAACCATTTTT

GGACCAATAGCTGATGTTGCCAGAGAAAAGCTGGCAAGAGAAGAACCAGA

TATTTATCAAATTGCAAAGAGTGAACCACGAGACGCTGGAACTGACCAAC

GTAGCTCTGGCATTATTCGCCTGCATACAATAAAGCAAATCATAGATCAA

GACAAACATGCTTTATTAGATGTAACACCAAATGCAGTTGATCGTCTTAA

CTATGCCCAGTGGTATCCAATTGTTGTATTTCTTAACCCTGATTCTAAGC

AAGGAGTAAAAACAATGAGAATGAGGTTATGTCCAGAATCTCGGAAAAGT

GCCAGGAAGTTATACGAGCGATCTCATAAACTTCGTAAAAATAATCACCA

TCTTTTTACAACTACAATTAACTTAAATTCAATGAATGATGGTTGGTATG

GTGCGCTGAAAGAAGCAATTCAACAACAGCAAAACCAGCTGGTATGGGTT

TCCGAGGGAAAGGCGGATGGTGCTACAAGTGATGACCTTGATTTGCATGA

TGATCGTCTGTCCTACCTGTCAGCTCCAGGTAGTGAATACTCAATGTATA

GCACGGACAGTAGACACACTTCTGACTATGAAGACACAGACACAGAAGGC

GGGGCCTACACTGATCAAGAACTAGATGAAACTCTTAATGATGAGGTTGG

GACTCCACCGGAGTCTGCCATTACACGGTCCTCTGAGCCTGTAAGAGAGG

ACTCCTCTGGAATGCATCATGAAAACCAAACATATCCTCCTTACTCACCA

CAAGCGCAGCCACAACCAATTCATAGAATAGACTCCCCTGGATTTAAGCC

AGCCTCTCAACAGAAAGCAGAAGCTTCATCTCCAGTCCCTTACCTTTCGC

CTGAAACAAACCCAGCATCATCAACCTCTGCTGTTAATCATAATGTAAAT

TTAACTAATGTCAGACTGGAGGAGCCCACCCCAGCTCCTTCCACCTCTTA

CTCACCACAAGCTGATTCTTTAAGAACACCAAGTACTGAGGCAGCTCACA

TAATGCTAAGAGATCAAGAACCATCATTGTCGTCGCATGTAGATCCAACA

AAGGTGTATAGAAAGGATCCATATCCCGAGGAAATGATGAGGCAGAACCA

TGTTTTGAAACAGCCAGCCGTTAGTCACCCAGGGCACAGGCCAGACAAAG

AGCCTAATCTGACCTATGAACCCCAACTCCCATACGTAGAGAAACAAGCC

AGCAGAGACCTCGAGCAGCCCACATACAGATACGAGTCCTCAAGCTATAC

GGACCAGTTTTCTCGAAACTATGAACATCGTCTGCGATACGAAGATCGCG

TCCCCATGTATGAAGAACAGTGGTCATATTATGATGACAAACAGCCCTAC

CCATCTCGGCCACCTTTTGATAATCAGCACTCTCAAGACCTTGACTCCAG

ACAGCATCCCGAAGAGTCCTCAGAACGAGGGTACTTTCCACGTTTTGAAG

AGCCAGCCCCTCTGTCTTACGACAGCAGACCACGTTACGAACAGGCACCT

-continued

AGAGCATCCGCCCTGCGGCACGAAGAGCAGCCAGCTCCTGGGTATGACAC

ACATGGTAGACTCAGACCGGAAGCCCAGCCCCACCCTTCAGCAGGGCCCA

AGCCTGCAGAGTCCAAGCAGTATTTTGAGCAATATTCACGCAGTTACGAG

CAAGTACCACCCCAAGGATTTACCTCTAGAGCAGGTCATTTTGAGCCTCT

CCATGGTGCTGCAGCTGTCCCTCCGCTGATACCTTCATCTCAGCATAAGC

CAGAAGCTCTGCCTTCAAACACCAAACCACTGCCTCCACCCCCAACTCAA

ACCGAAGAAGAGGAAGATCCAGCAATGAAGCCACAGTCTGTACTCACCAG

AGTTAAGATGTTTGAAAACAAAAGATCTGCATCCTTAGAGACCAAGAAGG

ATGTAAATGACACTGGCAGTTTTAAGCCTCCAGAAGTAGCATCTAAACCT

TCAGGTGCTCCCATCATTGGTCCCAAACCCACTTCTCAGAATCAATTCAG

TGAACATGACAAAACTCTGTACAGGATCCCAGAACCTCAAAAACCTCAAC

TGAAGCCACCTGAAGATATTGTTCGGTCCAATCATTATGACCCTGAAGAA

GATGAAGAATATTATCGAAAACAGCTGTCATACTTTGACCGAAGAAGTTT

TGAGAATAAGCCTCCTGCACACATTGCCGCCAGCCATCTCTCCGAGCCTG

CAAAGCCAGCGCATTCTCAGAATCAATCAAATTTTTCTAGTTATTCTTCA

AAGGGAAAGCCTCCTGAAGCTGATGGTGTGGATAGATCATTTGGCGAGAA

ACGCTATGAACCCATCCAGGCCACTCCCCCTCCTCCTCCATTGCCCTCGC

AGTATGCCCAGCCATCTCAGCCTGTCACCAGCGCGTCTCTCCACATACAT

TCTAAGGGAGCACATGGTGAAGGTAATTCAGTGTCATTGGATTTTCAGAA

TTCCTTAGTGTCCAAACCAGACCCACCTCCATCTCAGAATAAGCCAGCAA

CTTTCAGACCACCAAACCGAGAAGATACTGCTCAGGCAGCTTTCTATCCC

CAGAAAAGTTTTCCAGATAAAGCCCCAGTTAATGGAACTGAACAGACTCA

GAAAACAGTCACTCCAGCATACAATCGATTCACACCAAAACCATATACAA

GTTCTGCCCGACCATTTGAACGCAAGTTTGAAAGTCCTAAATTCAATCAC

AATCTTCTGCCAAGTGAAACTGCACATAAACCTGACTTGTCTTCAAAAAC

TCCCACTTCTCCAAAAACTCTTGTGAAATCGCACAGTTTGGCACAGCCTC

CTGAGTTTGACAGTGGAGTTGAAACTTTCTCTATCCATGCAGAGAAGCCT

AAATATCAAATAAATAATATCAGCACAGTGCCTAAAGCTATTCCTGTGAG

TCCTTCAGCTGTGGAAGAGGATGAAGATGAAGATGGTCATACTGTGGTGG

CCACAGCCCGAGGCATATTTAACAGCAATGGGGGCGTGCTGAGTTCCATA

GAAACTGGTGTTAGTATAATTATCCCTCAAGGAGCCATTCCCGAAGGAGT

TGAGCAGGAAATCTATTTCAAGGTCTGCCGGGACAACAGCATCCTTCCAC

CTTTAGATAAAGAGAAAGGTGAAACACTGCTGAGTCCTTTGGTGATGTGT

GGTCCCCATGGCCTCAAGTTCCTGAAGCCTGTGGAGCTGCGCTTACCACA

CTGTGATCCTAAAACCTGGCAAAACAAGTGTCTTCCCGGAGATCCAAATT

ATCTCGTTGGAGCAAACTGTGTTTCTGTCCTTATTGACCACTTTTAA

ZO1, amino acid sequence (1748 aa), SEQ ID NO. 18:

MSARAAAAKSTAMEETAIWEQHTVTLHRAPGFGFGIAISGGRDNPHFQSG

ETSIVISDVLKGGPAEGQLQENDRVAMVNGVSMDNVEHAFAVQQLRKSGK

-continued

```
NAKITIRRKKKVQIPVSRPDPEPVSDNEEDSYDEEIHDPRSGRSGVVNRR
SEKIWPRDRSASRERSLSPRSDRRSVASSQPAKPTKVTLVKSRKNEEYGL
RLASHIFVKEISQDSLAARDGNIQEGDVVLKINGTVTENMSLTDAKTLIE
RSKGKLKMVVQRDERATLLNVPDLSDSIHSANASERDDISEIQSLASDHS
GRSHDRPPRRSRSRSPDQRSEPSDHSRHSPQQPSNGSLRSRDEERISKPG
AVSTPVKHADDHTPKTVEEVTVERNEKQTPSLPEPKPVYAQVGQPDVDLP
VSPSDGVLPNSTHEDGILRPSMKLVKFRKGDSVGLRLAGGNDVGIFVAGV
LEDSPAAKEGLEEGDQILRVNNVDFTNIIREEAVLFLLDLPKGEEVTILA
QKKKDVYRRIVESDVGDSFYIRTHFEYEKESPYGLSFNKGEVFRVVDTLY
NGKLGSWLAIRIGKNHKEVERGIIPNKNRAEQLASVQYTLPKTAGGDRAD
FWRFRGLRSSKRNLRKSREDLSAQPVQTKFPAYERVVLREAGFLRPVTIF
GPIADVAREKLAREEPDIYQIAKSEPRDAGTDQRSSGIIRLHTIKQIIDQ
DKHALLDVTPNAVDRLNYAQWYPIVVFLNPDSKQGVKTMRMRLCPESRKS
ARKLYERSHKLRKNNHHLFTTTINLNSMNDGWYGALKEAIQQQQNQLVWV
SEGKADGATSDDLDLHDDRLSYLSAPGSEYSMYSTDSRHTSDYEDTDTEG
GAYTDQELDETLNDEVGTPPESAITRSSEPVREDSSGMHHENQTYPPYSP
QAQPQPIHRIDSPGFKPASQQKAEASSPVPYLSPETNPASSTSAVNHNVN
LTNVRLEEPTPAPSTSYSPQADSLRTPSTEAAHIMLRDQEPSLSSHVDPT
KVYRKDPYPEEMMRQNHVLKQPAVSHPGHRPDKEPNLTYEPQLPYVEKQA
SRDLEQPTYRYESSSYTDQFSRNYEHRLRYEDRVPMYEEQWSYYDDKQPY
PSRPPFDNQHSQDLDSRQHPEESSERGYFPRFEEPAPLSYDSRPRYEQAP
RASALRHEEQPAPGYDTHGRLRPEAQPHPSAGPKPAESKQYFEQYSRSYE
QVPPQGFTSRAGHFEPLHGAAAVPPLIPSSQHKPEALPSNTKPLPPPPTQ
TEEEEDPAMKPQSVLTRVKMFENKRSASLETKKDVNDTGSFKPPEVASKP
SGAPIIGPKPTSQNQFSEHDKTLYRIPEPQKPQLKPPEDIVRSNHYDPEE
DEEYYRKQLSYFDRRSFENKPPAHIAASHLSEPAKPAHSQNQSNFSSYSS
KGKPPEADGVDRSFGEKRYEPIQATPPPPPLPSQYAQPSQPVTSASLHIH
SKGAHGEGNSVSLDFQNSLVSKPDPPPSQNKPATFRPPNREDTAQAAFYP
QKSFPDKAPVNGTEQTQKTVTPAYNRFTPKPYTSSARPFERKFESPKFNH
NLLPSETAHKPDLSSKTPTSPKTLVKSHSLAQPPEFDSGVETFSIHAEKP
KYQINNISTVPKAIPVSPSAVEEDEDEDGHTVVATARGIFNSNGGVLSSI
ETGVSIIIPQGAIPEGVEQEIYFKVCRDNSILPPLDKEKGETLLSPLVMC
GPHGLKFLKPVELRLPHCDPKTWQNIKCLPGDPNYLVGANCVSVLIDHF
```

8. Multi PDZ Domain Protein 1

MUPP1, nucleotide sequence (6129 nt), SEQ ID NO. 19:

```
ATGTTGGAAGCCATTGACAAAAATCGGGCCCTGCATGCAGCAGAGCGCTT
GCAAACCAAGCTGCGAGAACGTGGGGATGTAGCAAATGAAGACAAACTGA
GCCTTCTGAAGTCAGTCCTGCAGAGCCCTCTCTTCAGTCAGATTCTGAGC
CTTCAGACTTCTGTACAGCAGCTGAAAGACCAGGTAAATATTGCAACTTC
AGCAACTTCAAATATTGAATATGCCCACGTTCCTCATCTCAGCCCAGCTG
```

-continued

```
TGATTCCTACTCTGCAAAATGAATCGTTTTTATTATCCCCAAACAATGGG
AATCTGGAAGCACTTACAGGACCTGGTATTCCACACATTAATGGGAAACC
TGCTTGTGATGAATTTGATCAGCTTATCAAAAATATGGCCCAGGGTCGCC
ATGTAGAAGTTTTTGAGCTCCTCAAACCTCCATCTGGAGGCCTTGGGTTT
AGTGTTGTGGGACTAAGAAGTGAAAACAGAGGAGAGCTGGGAATATTTGT
TCAAGAGATACAAGAGGGCAGTGTGGCCCATAGAGATGGAAGATTGAAAG
AAACTGATCAAATTCTTGCTATCAATGGACAGGCTCTTGATCAGACAATT
ACACATCAGCAGGCTATCAGCATCCTGCAGAAAGCCAAAGATACTGTCCA
GCTAGTTATTGCCAGAGGCTCATTGCCTCAGCTTGTCAGCCCCATAGTTT
CCCGTTCTCCATCTGCAGCCAGCACAATTTCAGCTCACTCTAATCCGGTT
CACTGGCAACACATGGAAACGATTGAATTGGTGAATGATGGATCTGGTTT
GGGATTTGGCATCATAGGAGGAAAAGCAACTGGTGTGATAGTAAAAACCA
TTCTGCCTGGAGGAGTAGCTGATCAGCATGGGCGTTTATGCAGTGGAGAC
CACATTCTAAAGATTGGTGACACAGATCTAGCAGGAATGAGCAGTGAGCA
AGTAGCACAAGTCCTTAGGCAATGTGGAAATAGAGTTAAGTTGATGATTG
CAAGAGGTGCCATAGAAGAACGTACAGCACCCACTGCTTTGGGCATCACC
CTCTCCTCATCCCCAACTTCAACACCAGAGTTGCGGGTTGATGCTTCTAC
TCAGAAAGGTGAAGAAAGTGAGACATTTGATGTAGAACTCACTAAAAATG
TCCAAGGATTAGGAATTACCATTGCTGGCTACATTGGAGATAAAAAATTG
GAACCTTCAGGAATCTTTGTAAAGAGCATTACAAAAAGCAGTGCCGTTGA
GCATGATGGAAGAATCCAAATTGGAGACCAAATTATAGCAGTAGATGGCA
CAAACCTTCAGGGTTTTACTAATCAGCAAGCAGTAGAGGTATTGCGACAT
ACAGGACAAACTGTGCTCCTGACACTAATGAGGAGAGGAATGAAGCAGGA
AGCCGAGCTCATGTCAAGGGAAGACGTCACAAAAGATGCAGATTTGTCTC
CTGTTAATGCCAGCATAATCAAAGAAAATTATGAAAAAGATGAAGATTTT
TTATCTTCGACGAGAAACACCAACATATTACCAACTGAAGAAGAAGGGTA
TCCATTACTGTCAGCTGAGATAGAAGAAATAGAAGATGCACAAAAACAAG
AAGCTGCTCTGCTGACAAAATGGCAAAGGATTATGGGAATTAACTATGAA
ATAGTGGTGGCCCATGTGAGCAAGTTTAGTGAGAACAGTGGATTGGGGAT
AAGCCTGGAAGCGACAGTGGGACATCATTTTATCCGATCTGTTCTACCAG
AGGGTCCTGTTGGACACAGCGGGAAGCTCTTCAGTGGAGACGAGCTATTG
GAAGTAAATGGCATAACTTTACTTGGGGAAAATCACCAAGATGTGGTGAA
TATCTTAAAAGAACTGCCTATAGAAGTGACAATGGTGTGCTGTCGTCGAA
CTGTGCCACCCACCACCCAATCAGAATTGGATAGCCTGGACTTATGTGAT
ATTGAGCTAACAGAAAAGCCTCACGTAGATCTAGGTGAGTTCATCGGGTC
ATCAGAGACAGAGGATCCAGTGCTGGCGATGACTGATGCGGGTCAGAGTA
CAGAAGAGGTTCAAGCACCTTTGGCCATGTGGGAGGCTGGCATTCAGCAC
ATAGAGCTGGAGAAAGGGAGCAAAGGACTTGGTTTTAGCATTTTAGATTA
TCAGGATCCAATTGATCCAGCAAGCACTGTGATTATAATTCGTTCTTTGG
TGCCTGGCGGCATTGCTGAAAAGGATGGACGACTTCTTCCTGGTGACCGA
CTCATGTTTGTAAACGATGTTAACTTGGAAAACAGCAGTCTTGAGGAAGC
```

-continued

```
TGTAGAAGCACTGAAGGGAGCACCGTCAGGGACTGTGAGAATAGGAGTTG
CTAAGCCTTTACCCCTTTCACCAGAAGAAGGTTATGTTTCTGCTAAGGAG
GATTCCTTTCTCTACCCACCACACTCCTGTGAGGAAGCAGGGCTGGCTGA
CAAACCCCTCTTCAGGGCTGACTTGGCTCTGGTGGGCACAAATGATGCTG
ACTTAGTAGATGAATCCACATTTGAGTCTCCATACTCTCCTGAAAATGAC
AGCATCTACTCTACTCAAGCCTCTATTTTATCTCTTCATGGCAGTTCTTG
TGGTGATGGCCTGAACTATGGTTCTTCCCTTCCATCATCTCCTCCTAAGG
ATGTTATTGAAAATTCTTGTGATCCAGTACTTGATCTGCATATGTCTCTG
GAGGAACTATATACCCAGAATCTCCTGCAAAGACAGGATGAGAATACACC
TTCGGTGGACATAAGTATGGGGCCTGCTTCTGGCTTTACTATAAATGACT
ACACACCTGCAAATGCTATTGAACAACAATATGAATGTGAAAACACAATA
GTGTGGACTGAATCTCATTTACCAAGTGAAGTTATATCAAGTGCAGAACT
TCCTTCTGTGCTACCCGATTCAGCTGGAAAGGGCTCTGAGTACCTGCTTG
AACAGAGCTCCCTGGCCTGTAATGCTGAGTGTGTCATGCTTCAAAATGTA
TCTAAAGAATCTTTTGAAAGGACTATTAATATAGCAAAAGGCAATTCTAG
CCTAGGAATGACAGTTAGTGCTAATAAAGATGGCTTGGGGATGATCGTTC
GAAGCATTATTCATGGAGGTGCCATTAGTCGAGATGGCCGGATTGCCATT
GGGGACTGCATCTTGTCCATTAATGAAGAGTCTACCATCAGTGTAACCAA
TGCCCAGGCACGAGCTATGTTGAGAAGACATTCTCTCATTGGCCCTGACA
TAAAAATTACTTATGTGCCTGCAGAACATTTGGAAGAGTTCAAAATAAGC
TTGGGACAACAATCTGGAAGAGTAATGGCACTGGATATTTTTTCTTCATA
CACTGGCAGAGACATTCCAGAATTACCAGAGCGAGAAGAGGGAGAGGGTG
AAGAAAGCGAACTTCAAAACACAGCATATAGCAATTGGAATCAGCCCAGG
CGGGTGGAACTCTGGAGAGAACCAAGCAAATCCTTAGGCATCAGCATTGT
TGGTGGACGAGGGATGGGGAGTCGGCTAAGCAATGGAGAAGTGATGAGGG
GCATTTTCATCAAACATGTTCTGGAAGATAGTCCAGCTGGCAAAAATGGA
ACCTTGAAACCTGGAGATAGAATCGTAGAGGTGGATGGAATGGACCTCAG
AGATGCAAGCCATGAACAAGCTGTGGAAGCCATTCGGAAAGCAGGCAACC
CTGTAGTCTTTATGGTACAGAGCATTATAAACAGACCAAGGAAATCCCCT
TTGCCTTCCTTGCTGCACAACCTTTACCCTAAGTACAACTTCAGCAGCAC
TAACCCATTTGCTGACTCTCTACAAATCAACGCCGACAAGGCACCCAGTC
AGTCAGAGTCAGAGCCAGAGAAGGCTCCATTGTGCAGTGTGCCCCCACCC
CCTCCTTCAGCCTTTGCCGAAATGGGTAGTGATCACACACAGTCATCTGC
AAGCAAAATCTCACAAGATGTGGACAAAGAGGATGAGTTTGGTTACAGCT
GGAAAAATATCAGAGAGCGTTATGGAACCCTAACAGGCGAGCTGCATATG
ATTGAACTGGAGAAAGGTCATAGTGGTTTGGGCCTAAGTCTTGCTGGGAA
CAAAGACCGATCCAGGATGAGTGTCTTCATAGTGGGGATTGATCCAAATG
GAGCTGCAGGAAAAGATGGTCGATTGCAAATTGCAGATGAGCTTCTAGAG
ATCAATGGTCAGATTTTATATGGAAGAAGTCATCAGAATGCCTCATCAAT
CATTAAATGTGCCCCTTCTAAAGTGAAAATAATTTTTATCAGAAATAAAG
```

-continued

```
ATGCAGTGAATCAGATGGCCGTATGTCCTGGAAATGCAGTAGAACCTTTG
CCTTCTAACTCAGAAAATCTTCAAAATAAGGAGACAGAGCCAACTGTTAC
TACTTCTGATGCAGCTGTGGACCTCAGTTCATTTAAAAATGTGCAACATC
TGGAGCTTCCCAAGGATCAGGGGGGTTTGGGTATTGCTATCAGCGAAGAA
GATACACTCAGTGGAGTCATCATAAAGAGCTTAACAGAGCATGGGGTAGC
AGCCACGGATGGACGACTCAAAGTCGGAGATCAGATACTGGCTGTAGATG
ATGAAATTGTTGTTGGTTACCCTATTGAAAAGTTTATTAGCCTTCTGAAG
ACAGCAAAGATGACAGTAAAACTTACCATCCATGCTGAGAATCCAGATTC
CCAGGCTGTTCCTTCAGCAGCTGGTGCAGCCAGTGGAGAAAAAAAGAACA
GCTCCCAGTCTCTGATGGTCCCACAGTCTGGCTCCCCAGAACCGGAGTCC
ATCCGAAATACAAGCAGATCATCAACACCAGCAATTTTTGCTTCTGATCC
TGCAACCTGCCCCATTATCCCTGGCTGCGAAACAACCATCGAGATTTCCA
AAGGGCGAACAGGGCTGGGCCTGAGCATCGTTGGGGGTTCAGACACGCTG
CTGGGTGCCATTATTATCCATGAAGTTTATGAAGAAGGAGCAGCATGTAA
AGATGGAAGACTCTGGGCTGGAGATCAGATCTTAGAGGTGAATGGAATTG
ACTTGAGAAAGGCCACACATGATGAAGCAATCAATGTCCTGAGACAGACG
CCACAGAGAGTGCGCCTGACACTCTACAGAGATGAGGCCCCATACAAAGA
GGAGGAAGTGTGTGACACCCTCACTATTGAGCTGCAGAAGAAGCCGGGAA
AAGGCCTAGGATTAAGTATTGTTGGTAAAAGAAACGATACTGGAGTATTT
GTGTCAGACATTGTCAAAGGAGGAATTGCAGATGCCGATGGAAGACTGAT
GCAGGGAGACCAGATATTAATGGTGAATGGGGAAGACGTTCGTAATGCCA
CCCAAGAAGCGGTTGCCGCTTTGCTAAAGTGTTCCCTAGGCACAGTAACC
TTGGAAGTTGGAAGAATCAAAGCTGGATCCAGTACATCTGAGTCACTGGA
AAGTAGCTCAAAGAAGAATGCATTGGCATCTGAAATACAGGGATTAAGAA
CAGTCGAAATGAAAAAGGGCCCTACTGACTCACTGGGAATCAGCATCGCT
GGAGGAGTAGGCAGCCCACTTGGTGATGTGCCTATATTTATTGCAATGAT
GCACCCAACTGGAGTTGCAGCACAGACCCAAAAACTCAGAGTTGGGGATA
GGATTGTCACCATCTGTGGCACATCCACTGAGGGCATGACTCACACCCAA
GCAGTTAACCTACTGAAAAATGCATCTGGCTCCATTGAAATGCAGGTGGT
TGCTGGAGGAGACGTGAGTGTGGTCACAGGTCATCAGCAGGAGCCTGCAA
GTTCCAGTCTTTCTTTCACTGGGCTGACGTCAAGCAGTATATTTCAGGAT
GATTTAGGACCTCCTCAATGTAAGTCTATTACACTAGAGCGAGGACCAGA
TGGCTTAGGCTTCAGTATAGTTGGAGGATATGGCAGCCCTCATGGAGACT
TACCCATTTATGTTAAAACAGTGTTTGCAAAGGGAGCAGCCTCTGAAGAC
GGACGTCTGAAAAGGGGCGATCAGATCATTGCTGTCAATGGGCAGAGTCT
AGAAGGAGTCACCCATGAAGAAGCTGTTGCCATCCTTAAACGGACAAAAG
GCACTGTCACTTTGATGGTTCTCTCTTGA
```

MUPP1, amino acid sequence (2042 aa), SEQ ID NO. 20:

```
MLEAIDKNRALHAAERLQTKLRERGDVANEDKLSLLKSVLQSPLFSQILS
LQTSVQQLKDQVNIATSATSNIEYAHVPHLSPAVIPTLQNESFLLSPNNG
```

-continued

NLEALTGPGIPHINGKPACDEFDQLIKNMAQGRHVEVFELLKPPSGGLGF

SVVGLRSENRGELGIFVQEIQEGSVAHRDGRLKETDQILAINGQALDQTI

THQQAISILQKAKDTVQLVIARGSLPQLVSPIVSRSPSAASTISAHSNPV

HWQHMETIELVNDGSGLGFGIIGGKATGVIVKTILPGGVADQHGRLCSGD

HILKIGDTDLAGMSSEQVAQVLRQCGNRVKLMIARGAIEERTAPTALGIT

LSSSPTSTPELRVDASTQKGEESETFDVELTKNVQGLGITIAGYIGDKKL

EPSGIFVKSITKSSAVEHDGRIQIGDQIIAVDGTNLQGFTNQQAVEVLRH

TGQTVLLTLMRRGMKQEAELMSREDVTKDADLSPVNASIIKENYEKDEDF

LSSTRNTNILPTEEEGYPLLSAEIEEIEDAQKQEAALLTKWQRIMGINYE

IVVAHVSKFSENSGLGISLEATVGHHFIRSVLPEGPVGHSGKLFSGDELL

EVNGITLLGENHQDVVNILKELPIEVTMVCCRRTVPPTTQSELDSLDLCD

IELTEKPHVDLGEFIGSSETEDPVLAMTDAGQSTEEVQAPLAMWEAGIQH

IELEKGSKGLGFSILDYQDPIDPASTVIIIRSLVPGGIAEKDGRLLPGDR

LMFVNDVNLENSSLEEAVEALKGAPSGTVRIGVAKPLPLSPEEGYVSAKE

DSFLYPPHSCEEAGLADKPLFRADLALVGTNDADLVDESTFESPYSPEND

SIYSTQASILSLHGSSCGDGLNYGSSLPSSPPKDVIENSCDPVLDLHMSL

EELYTQNLLQRQDENTPSVDISMGPASGFTINDYTPANAIEQQYECENTI

VWTESHLPSEVISSAELPSVLPDSAGKGSEYLLEQSSLACNAECVMLQNV

SKESFERTINIAKGNSSLGMTVSANKDGLGMIVRSIIHGGAISRDGRIAI

GDCILSINEESTISVTNAQARAMLRRHSLIGPDIKITYVPAEHLEEFKIS

LGQQSGRVMALDIFSSYTGRDIPELPEREEGEGEESELQNTAYSNWNQPR

-continued

RVELWREPSKSLGISIVGGRGMGSRLSNGEVMRGIFIKHVLEDSPAGKNG

TLKPGDRIVEVDGMDLRDASHEQAVEAIRKAGNPVVFMVQSIINRPRKSP

LPSLLHNLYPKYNFSSTNPFADSLQINADKAPSQSESEPEKAPLCSVPPP

PPSAFAEMGSDHTQSSASKISQDVDKEDEFGYSWKNIRERYGTLTGELHM

IELEKGHSGLGLSLAGNKDRSRMSVFIVGIDPNGAAGKDGRLQIADELLE

INGQILYGRSHQNASSIIKCAPSKVKIIFIRNKDAVNQMAVCPGNAVEPL

PSNSENLQNKETEPTVTTSDAAVDLSSFKNVQHLELPKDQGGLGIAISEE

DTLSGVIIKSLTEHGVAATDGRLKVGDQILAVDDEIVVGYPIEKFISLLK

TAKMTVKLTIHAENPDSQAVPSAAGAASGEKKNSSQSLMVPQSGSPEPES

IRNTSRSSTPAIFASDPATCPIIPGCETTIEISKGRTGLGLSIVGGSDTL

LGAIIIHEVYEEGAACKDGRLWAGDQILEVNGIDLRKATHDEAINVLRQT

PQRVRLTLYRDEAPYKEEEVCDTLTIELQKKPGKGLGLSIVGKRNDTGVF

VSDIVKGGIADADGRLMQGDQILMVNGEDVRNATQEAVAALLKCSLGTVT

LEVGRIKAGSSTSESLESSSKKNALASEIQGLRTVEMKKGPTDSLGISIA

GGVGSPLGDVPIFIAMMHPTGVAAQTQKLRVGDRIVTICGTSTEGMTHTQ

AVNLLKNASGSIEMQVVAGGDVSVVTGHQQEPASSSLSFTGLTSSSIFQD

DLGPPQCKSITLERGPDGLGFSIVGGYGSPHGDLPIYVKTVFAKGAASED

GRLKRGDQIIAVNGQSLEGVTHEEAVAILKRTKGTVTLMVLS

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. A method for down-regulating or inhibiting Coxsackievirus-Adenovirus Receptor (CAR) in a heart of a subject not suffering from myocarditis, comprising administering to the subject at least one of:

a CAR protein ligand or a CAR protein ligand fragment, wherein the heart is a heart subjected to inadequate perfusion.

2. The method of claim 1, wherein the down-regulating or inhibiting Coxsackievirus-Adenovirus Receptor (CAR) in the heart of a subject comprises administering to the subject at least one of an antibody specifically binding to the CAR, a specifically binding fragment of the antibody, a CAR-Fc-fusion protein, fibronectin, a CAR ligand fusion protein and a fusion protein of any of the before-mentioned proteins.

3. A method for down-regulating or inhibiting Coxsackievirus-Adenovirus Receptor (CAR) in a cardiac cell of a subject not suffering from myocarditis, comprising:

functionally inhibiting a CAR protein by administering to the subject a CAR protein ligand, wherein the cardiac cell is a cardiac cell subjected to inadequate perfusion.

4. The method of claim 3, wherein the functional inhibition of the CAR protein is achieved using at least one of an antibody specifically binding to the CAR, a specifically binding fragment of the antibody, a CAR-Fc-fusion protein, and fibronectin.

5. A method for down-regulating or inhibiting Coxsackievirus-Adenovirus Receptor (CAR) in a heart of a subject not suffering from myocarditis, comprising administering to the subject at least one of:

a CAR protein ligand or a CAR protein ligand fragment, wherein the heart is a heart subjected to ischemia.

* * * * *